United States Patent
Duesterhoft et al.

(10) Patent No.: US 10,265,219 B2
(45) Date of Patent: Apr. 23, 2019

(54) WOUND DRESSING MONITORING SYSTEMS INCLUDING APPURTENANCES FOR WOUND DRESSINGS

(71) Applicant: Elwha LLC, Bellevue, WA (US)

(72) Inventors: Paul Duesterhoft, Issaquah, WA (US); Nicholas Dykstra, Seattle, WA (US); Daniel Hawkins, Pleasanton, CA (US); Roderick A. Hyde, Redmond, WA (US); Jordin T. Kare, Seattle, WA (US); Eric C. Leuthardt, St. Louis, MO (US); Elizabeth L. Schubert, Bellevue, WA (US); Clarence T. Tegreene, Mercer Island, WA (US); Lowell L. Wood, Jr., Bellevue, WA (US)

(73) Assignee: ELWHA LLC, Bellevue, WA (US)

( * ) Notice: Subject to any disclaimer, the term of this patent is extended or adjusted under 35 U.S.C. 154(b) by 773 days.

(21) Appl. No.: 14/252,136

(22) Filed: Apr. 14, 2014

(65) Prior Publication Data
US 2014/0298928 A1 Oct. 9, 2014

Related U.S. Application Data

(63) Continuation-in-part of application No. 13/445,174, filed on Apr. 12, 2012, which is a continuation-in-part
(Continued)

(51) Int. Cl.
*G01N 33/00* (2006.01)
*A61F 13/00* (2006.01)
(Continued)

(52) U.S. Cl.
CPC ........ *A61F 13/00051* (2013.01); *A61B 5/002* (2013.01); *A61B 5/0022* (2013.01);
(Continued)

(58) Field of Classification Search
CPC .................................................. A61M 1/0088
(Continued)

(56) References Cited

U.S. PATENT DOCUMENTS 3,927,669 A * 12/1975 Glatt ................. A61F 13/00021
602/47
4,384,288 A 5/1983 Walton
(Continued)

FOREIGN PATENT DOCUMENTS

EP 0 430 608 A1 6/1991
WO WO 00/08203 2/2000
(Continued)

OTHER PUBLICATIONS

European Search Report; European App. No. EP 13 77 5331; dated Nov. 6, 2015 (received by our Agent on Nov. 12, 2015); pp. 1-3.
(Continued)

*Primary Examiner* — May A Abouelela
(74) *Attorney, Agent, or Firm* — Dorsey & Whitney LLP

(57) ABSTRACT

Appurtenances to a wound dressing and systems for monitoring wound dressings are described. In some embodiments, a system for monitoring a wound dressing includes: an appurtenance to a wound dressing, wherein the appurtenance includes a sensor unit, an electronic identifier, and a transmitter unit operably attached to the sensor unit and to the electronic identifier; and a local unit including a receiver for the transmitter unit, a processor operably attached to the receiver, and a communication unit operably attached to the processor.

28 Claims, 14 Drawing Sheets

Related U.S. Application Data of application No. 13/445,220, filed on Apr. 12, 2012, now Pat. No. 9,084,530.

(51) Int. Cl.
| | | |
|---|---|---|
| *A61B 5/00* | (2006.01) | |
| *A61M 1/00* | (2006.01) | |
| *G06F 19/00* | (2018.01) | |
| *G16H 40/67* | (2018.01) | |
| *A61B 5/145* | (2006.01) | |
| *G16H 40/63* | (2018.01) | |

(52) U.S. Cl.
CPC .......... *A61B 5/445* (2013.01); *A61M 1/0025* (2014.02); *G06F 19/00* (2013.01); *G16H 40/67* (2018.01); *A61B 5/14539* (2013.01); *A61M 1/0088* (2013.01); *A61M 2205/3344* (2013.01); *A61M 2205/3382* (2013.01); *A61M 2205/3553* (2013.01); *A61M 2205/3592* (2013.01); *A61M 2230/50* (2013.01); *G01N 33/00* (2013.01); *G16H 40/63* (2018.01)

(58) Field of Classification Search
USPC .................. 600/573, 583; 604/319; 602/42
See application file for complete search history.

(56) References Cited

U.S. PATENT DOCUMENTS

| | | | | |
|---|---|---|---|---|
| 4,430,998 | A * | 2/1984 | Harvey | A61B 17/085 606/216 |
| 4,753,232 | A * | 6/1988 | Ward | A61F 13/023 602/52 |
| 4,924,866 | A | 5/1990 | Yoon | |
| 5,047,047 | A * | 9/1991 | Yoon | A61B 17/083 606/213 |
| 5,507,775 | A * | 4/1996 | Ger | A61B 17/08 606/215 |
| 5,704,352 | A | 1/1998 | Tremblay et al. | |
| 5,876,365 | A | 3/1999 | Hart | |
| 5,904,671 | A * | 5/1999 | Navot | A61F 13/20 340/573.5 |
| 5,912,114 | A | 6/1999 | Hutchinson et al. | |
| 5,939,205 | A | 8/1999 | Yokoyama et al. | |
| 5,964,723 | A * | 10/1999 | Augustine | A61F 7/007 602/2 |
| 5,986,163 | A | 11/1999 | Augustine | |
| 6,037,879 | A | 3/2000 | Tuttle | |
| 6,248,084 | B1 | 6/2001 | Augustine et al. | |
| 6,270,455 | B1 | 8/2001 | Brown | |
| 6,283,938 | B1 | 9/2001 | McConnell | |
| 6,348,640 | B1 | 2/2002 | Navot et al. | |
| 6,420,622 | B1 | 7/2002 | Johnston et al. | |
| 6,569,189 | B1 * | 5/2003 | Augustine | A61F 7/007 602/14 |
| 6,693,513 | B2 * | 2/2004 | Tuttle | G06K 19/0716 340/10.1 |
| 6,863,220 | B2 | 3/2005 | Selker | |
| 6,889,165 | B2 | 5/2005 | Lind et al. | |
| 6,963,772 | B2 | 11/2005 | Bloom et al. | |
| 7,030,764 | B2 | 4/2006 | Smith et al. | |
| 7,055,754 | B2 * | 6/2006 | Forster | G06K 19/07749 235/492 |
| 7,215,976 | B2 | 5/2007 | Brideglall | |
| 7,297,112 | B2 | 11/2007 | Zhou et al. | |
| 7,361,184 | B2 * | 4/2008 | Joshi | A61M 1/0066 602/42 |
| 7,372,780 | B1 | 5/2008 | Braunberger | |
| 7,411,505 | B2 | 8/2008 | Smith et al. | |
| 7,446,660 | B2 | 11/2008 | Posamentier | |
| 7,479,886 | B2 | 1/2009 | Burr | |
| 7,507,675 | B2 | 3/2009 | Zuilhof et al. | |
| 7,520,872 | B2 * | 4/2009 | Biggie | A61M 1/0088 601/6 |
| 7,612,424 | B1 | 11/2009 | Espinosa et al. | |
| 7,666,151 | B2 | 2/2010 | Sullivan et al. | |
| 7,667,606 | B2 | 2/2010 | Packert et al. | |
| 7,703,334 | B2 | 4/2010 | Cochran | |
| 7,724,136 | B2 | 5/2010 | Posamentier | |
| 7,794,925 | B2 | 9/2010 | Cullen | |
| 7,813,226 | B2 | 10/2010 | Braunberger | |
| 7,825,776 | B2 | 11/2010 | Smith et al. | |
| 7,838,717 | B2 * | 11/2010 | Haggstrom | A61F 13/0203 128/888 |
| 7,883,494 | B2 | 2/2011 | Martin | |
| 7,896,856 | B2 | 3/2011 | Petrosenko et al. | |
| 7,914,867 | B2 | 3/2011 | Mori et al. | |
| 7,945,302 | B2 | 5/2011 | McAdams | |
| 7,951,605 | B2 | 5/2011 | Pitner et al. | |
| 7,964,390 | B2 | 6/2011 | Rozakis et al. | |
| 7,986,235 | B2 | 7/2011 | Posamentier | |
| 8,014,234 | B2 | 9/2011 | Braunberger | |
| 8,048,046 | B2 * | 11/2011 | Hudspeth | A61M 1/0088 604/119 |
| 8,057,446 | B2 * | 11/2011 | Kane | A61F 13/0203 604/304 |
| 8,257,328 | B2 * | 9/2012 | Augustine | A61M 1/0049 604/313 |
| 8,350,116 | B2 | 1/2013 | Lockwood et al. | |
| 8,376,972 | B2 * | 2/2013 | Fleischmann | A61F 13/00068 601/6 |
| 8,690,845 | B2 * | 4/2014 | Long | A61M 1/0088 604/317 |
| 8,760,295 | B2 * | 6/2014 | Forster | A61B 5/445 340/425.2 |
| 8,785,713 | B2 * | 7/2014 | Hong | A61L 15/425 602/41 |
| 8,795,257 | B2 * | 8/2014 | Coulthard | A61M 1/0031 604/313 |
| 8,808,274 | B2 * | 8/2014 | Hartwell | A61F 13/02 604/319 |
| 8,945,030 | B2 * | 2/2015 | Weston | A61M 1/0088 602/2 |
| 8,946,499 | B2 * | 2/2015 | Iyer | A61L 15/42 602/41 |
| 9,011,393 | B2 * | 4/2015 | Kazala, Jr. | A61M 1/0088 29/428 |
| 9,050,398 | B2 | 6/2015 | Armstrong et al. | |
| 9,168,180 | B2 * | 10/2015 | Ha | A61F 13/02 |
| 9,422,934 | B2 * | 8/2016 | Locke | F04B 53/00 |
| 2003/0199783 | A1 | 10/2003 | Bloom et al. | |
| 2003/0216663 | A1 | 11/2003 | Jersey-Willuhn et al. | |
| 2004/0073151 | A1 | 4/2004 | Weston | |
| 2004/0210280 | A1 | 10/2004 | Liedtke | |
| 2006/0036145 | A1 | 2/2006 | Brister et al. | |
| 2006/0047218 | A1 | 3/2006 | Bloom et al. | |
| 2007/0171076 | A1 | 7/2007 | Stevens et al. | |
| 2007/0203442 | A1 * | 8/2007 | Bechert | A61F 13/00063 602/52 |
| 2007/0204691 | A1 | 9/2007 | Bogner et al. | |
| 2007/0231380 | A1 | 10/2007 | Shah et al. | |
| 2007/0247316 | A1 | 10/2007 | Wildman et al. | |
| 2007/0252712 | A1 | 11/2007 | Allen et al. | |
| 2007/0269851 | A1 | 11/2007 | Sanders et al. | |
| 2008/0132821 | A1 * | 6/2008 | Propp | A61M 25/02 602/54 |
| 2008/0166397 | A1 | 7/2008 | Trotter et al. | |
| 2008/0171957 | A1 * | 7/2008 | Connolly | A61B 5/0531 602/42 |
| 2008/0234616 | A1 * | 9/2008 | Shives | A61F 13/00068 602/13 |
| 2009/0167495 | A1 | 7/2009 | Smith et al. | |
| 2009/0192369 | A1 | 7/2009 | Say et al. | |
| 2009/0209883 | A1 | 8/2009 | Higgins et al. | |
| 2009/0227969 | A1 | 9/2009 | Jaeb et al. | |
| 2009/0243813 | A1 | 10/2009 | Smith et al. | |
| 2009/0299161 | A1 | 12/2009 | Cullen et al. | |
| 2010/0010477 | A1 | 1/2010 | Augustine et al. | |
| 2010/0022990 | A1 | 1/2010 | Karpowicz et al. | |
| 2010/0030167 | A1 | 2/2010 | Thirstrup et al. | |
| 2010/0100061 | A1 | 4/2010 | Odland | |
| 2010/0125258 | A1 | 5/2010 | Coulthard et al. | |

(56) References Cited

U.S. PATENT DOCUMENTS

| | | | |
|---|---|---|---|
| 2010/0166694 A1 | 7/2010 | Stephens et al. | |
| 2010/0204606 A1 | 8/2010 | Kim et al. | |
| 2010/0228206 A1* | 9/2010 | Larsson | A61M 1/0084 604/319 |
| 2010/0249733 A9 | 9/2010 | Blott et al. | |
| 2010/0318052 A1* | 12/2010 | Ha | A61F 13/02 604/385.01 |
| 2010/0331634 A1 | 12/2010 | Müller et al. | |
| 2011/0015591 A1 | 1/2011 | Hanson et al. | |
| 2011/0034906 A1 | 2/2011 | Malhi | |
| 2011/0054340 A1 | 3/2011 | Russ et al. | |
| 2011/0082356 A1 | 4/2011 | Yang et al. | |
| 2011/0092927 A1* | 4/2011 | Wilkes | A61F 13/00059 604/304 |
| 2011/0105854 A1 | 5/2011 | Kiani et al. | |
| 2011/0140703 A1 | 6/2011 | Chiao et al. | |
| 2011/0160548 A1 | 6/2011 | Forster | |
| 2011/0172582 A1* | 7/2011 | Darian | A61F 15/004 602/79 |
| 2011/0178375 A1 | 7/2011 | Forster | |
| 2011/0213559 A1 | 9/2011 | Pollack et al. | |
| 2012/0010099 A1 | 1/2012 | Stephens et al. | |
| 2012/0016322 A1 | 1/2012 | Coulthard et al. | |
| 2012/0035560 A1* | 2/2012 | Eddy | A61F 13/0203 604/313 |
| 2012/0078157 A1 | 3/2012 | Ravikumar et al. | |
| 2012/0109034 A1* | 5/2012 | Locke | A61F 13/02 602/42 |
| 2012/0130325 A1 | 5/2012 | Blott et al. | |
| 2012/0238931 A1 | 9/2012 | Rastegar et al. | |
| 2012/0245540 A1 | 9/2012 | Zimnitsky et al. | |
| 2013/0053799 A1 | 2/2013 | Locke et al. | |
| 2013/0261409 A1 | 10/2013 | Pathak et al. | |
| 2013/0304006 A1 | 11/2013 | Toth | |
| 2013/0304007 A1* | 11/2013 | Toth | A61M 1/0031 604/321 |
| 2013/0317405 A1* | 11/2013 | Ha | A61F 13/0226 602/42 |
| 2013/0317406 A1 | 11/2013 | Locke et al. | |
| 2015/0208961 A1 | 7/2015 | Duesterhoft et al. | |
| 2015/0290045 A1 | 10/2015 | Fan et al. | |

FOREIGN PATENT DOCUMENTS

| | | |
|---|---|---|
| WO | WO 03/040406 A2 | 5/2003 |
| WO | WO 2005/009328 A1 | 2/2005 |
| WO | WO 2007/130239 A1 | 11/2007 |

OTHER PUBLICATIONS

European Search Report; European App. No. EP 13 77 5973; dated Nov. 4, 2015 (received by our Agent on Nov. 12, 2015); pp. 1-3.
U.S. Appl. No. 14/719,639, Duesterhoft et al.
U.S. Appl. No. 14/252,049, Allin et al.
U.S. Appl. No. 13/795,667, Duesterhoft et al.
U.S. Appl. No. 13/491,677, Duesterhoft et al.
U.S. Appl. No. 13/445,220, Duesterhoft et al.
U.S. Appl. No. 13/445,174, Duesterhoft et al.
Abhisam; "RFID systems for pharmaceutical distributors to meet the new FDA regulations on drugs"; Discover the power of e-learning!; bearing a date of 2006; pp. 1-7; Abhisam Software.
Alien Technology; "Battery Assisted Passive Tags"; Alien Technology brochure; downloaded from the web Oct. 17, 2011; pp. 1-2; located at: http://www.alientechnology.com/docs/AT_DS_BAP.pdf;Alien Technology Corp.
Berggren et al.; "Capacitive Biosensors"; Electroanalysis; bearing a date of 2001; pp. 173-180; vol. 13, No. 3; Wiley-VCH Verlag GmbH.
Bluestein et al.; "Pressure Ulcers: Prevention, Evaluation, and Management"; American Family Physician; Nov. 15, 2008; pp. 1186-1194; vol. 78, No. 10; American Academy of Family Physicians.
"Body-fluid battery"; Science News; Sep. 10, 2005; pp. 1-2; located at http://findarticles.com/p/articles/mi_ml200/is_11_168/aj_nl5674798/;Science Service, Inc. and Gale Group.
Chawla et al.; "An Overview of Passive RFID"; IEEE Applications & Practice; Sep. 2007; pp. 11-17; IEEE.
Chen et al.; "A 2G-RFID-Based E-Healthcare System"; IEEE Wireless Communications; Feb. 2010; pp. 37-43; IEEE.
Chen et al.; "Ultrasonic Measurement System with Infrared Communication Technology"; Journal of Computers; Nov. 2011; pp. 2468-2475; vol. 6, No. 11; Academy Publisher.
Clay, Karen S.; "Preventing pressure ulcers in your facility: Karen S. Clay, RN, BSN, CWCN, presents a primer on how to protect frail residents—and avoid costly reprimands"; 2004; 14 pages; HCPro, Inc.
Collier, Mark; "Recognition and management of wound infections"; World Wide Wounds; Jan. 2004; pp. 1-9.
Cui et al.; "Nanowire Nanosensors for Highly Sensitive and Selective Detection of Biological and Chemical Species"; Science; Aug. 17, 2001; pp. 1289-1292, and 1 cover page; vol. 293; American Association for the Advancement of Science.
Cutting et al.; "Criteria for identifying wound infection"; Journal of Wound Care; Jun. 1994; pp. 198-201; vol. 3, No. 4.
Dehennis et al.; "A Wireless Microsystem for the Remote Sensing of Pressure, Temperature, and Relative Humidity"; Journal of Microelectromechanical Systems; Feb. 2005; pp. 12-22; vol. 14, No. 1; IEEE.
Dowd et al.; "Survey of bacterial diversity in chronic wounds using Pyrosequencing, DGGE, and full ribosome shotgun sequencing"; BMC Microbiology; 2008; pp. 1-15; vol. 8, No. 43; BioMed Central Ltd.
Fadlullah et al; "Indoor High-Bandwidth Optical Wireless Links for Sensor Networks"; Journal of Lightwave Technology; Nov. 1, 2010; pp. 3086-3094; vol. 28, No. 21; IEEE.
Finkenzeller, Klaus; "Fundamental Operating Principles" Chapter 3 of the RFID Handbook: Fundamentals and Applications in Contactless Smart Cards and Identification; bearing a date of 2003; pp. 29-59; John Wiley & Sons, Ltd.
Fisher et al.; "Tracking the social dimensions of RFID systems in hospitals"; International Journal of Medical Informatics; bearing a date of 2008; pp. 176-183; vol. 77; Elsevier Ireland Ltd.
Fisher, Jill A.; "Indoor Positioning and Digital Management: Emerging Surveillance Regimes in Hospitals"; Chapter 5 in T. Monahan (Ed), Surveillance and Security: Technological Politics and Power in Everyday Life; May 23, 2006; pp. 77-88; Routledge.
Frost & Sullivan; "Advances in Wound Healing Techniques"; Technical Insights; Publication D11A; bearing a date of 2008; pp. 1-118; Frost & Sullivan.
Frost & Sullivan; "An Overview of Ulceration Wounds"; Publication M4BB-54; Dec. 2009; pp. 1-77; Frost & Sullivan.
Frost & Sullivan; "U.S. Advanced Wound Care Market"; Publication N71A-54; Aug. 2010; pp. 1- 90; Frost & Sullivan.
Goodisman, Jerry; "Observations on Lemon Cells"; Journal of Chemical Education; Apr. 2001; pp. 516-518; vol. 78, No. 4.
Gray, David; "Assessment, Diagnosis and Treatment of Infection"; Wounds UK; bearing a date of 2011; pp. 4-9; vol. 7, No. 2, supplement.
Grist et al.; "Optical Oxygen Sensors for Applications in Microfluidic Cell Culture"; Sensors; 2010; pp. 9286-9316; vol. 10; MDPI; Basel, Switzerland.
Huang et al.; "Development of an $IrO_x$ Micro pH Sensor Array on Flexible Polymer Substrate"; Nanosensors and Microsensors for Bio-Systems 2008, edited by Vijay K. Varadan, Proc. of SPIE, vol. 6931, 693104; 2008; pp. 1-9.
Huang et al.; "Investigation of Repeatability of Sol-Gel Iridium Oxide pH Sensor on Flexible Substrate"; Micro- and Nanotechnology: Materials, Processes, Packaging, and Systems IV, edited by Jung-Chih Chiao et al., Proc. of SPIE, vol. 7269, 726916; 2008; pp. 1-9.
Ibridge Network; "pH Sensor Array on Flexible Substrate For Wound Care (UTA Ref. No. 08-21)"; Nov. 28, 2011; pp. 1-2; Kauffman Innovation Network, Inc.

(56) References Cited

OTHER PUBLICATIONS

Intel; "WISP: Wireless Identification and Sensing Platform"; Intel Labs Seattle; printed on Oct. 8, 2011; pp. 1-4; located at http://www.seattle.intel-research.net/WISP/.
Intelleflex; "Worldwide RFID UHF Map"; printed on Oct. 17, 2011; p. 1; located at: http://www.intelleflex.com/pdf/Worldwide_UHF_Chart.pdf ; Intelleflex Corporation.
Karthik MNS; "Could blood be used to power batteries?"; Feb. 2009; pp. 1-4; located at: http://hoowstuffworks.blogspot.com/2009/02/could-blood-be-used-to-power-batteries.html.
Kavehrad, Mohsen; "Sustainable Energy-Efficient Wireless Applications Using Light"; IEEE Communications Magazine; Dec. 2010; pp. 66-73; IEEE.
Kelly-Quintos et al.; "Characterization of the Opsonic and Protective Activity Against *Staphylococcus aureus* of Fully Human Monoclonal Antibodies Specific for the Bacterial Surface Polysaccharide Poly-N-Acetylglucosamine"; Infection and Immunity; May 2006; pp. 2742-2750; vol. 74, No. 5; American Society for Microbiology.
Lee et al.; "Water Activated Disposable and Long Shelf Life Microbatteries"; 2003; pp. 387-390; IEEE.
Lim et al.; "A Micromechanical Biosensor with Interdigitated Capacitor Readout"; Proceedings of the 2011 IEEE/ICME International Conference on Complex Medical Engineering; May 22-25, 2011; pp. 42-46; IEEE.
Löfgren et al.; "Low-power humidity sensor for RFID applications"; Multi-Material Micro Manufacture; 2008; 4 pages; Cardiff University.
McColl et al.; "Monitoring moisture without disturbing the wound dressing"; Wounds UK; bearing a date of 2009; pp. 94-96, and 98-99; vol. 5, No. 3.
Mehmood et al.; "Applications of modern sensors and wireless technology in effective wound management"; Journal of Biomedical Materials Research B: Applied Biomaterials; 2013; pp. 1-11; Wiley Peridicals Inc.
Murata Manufacturing Co., Ltd.; "Piezoelectric Sound Components"; Cat. No. P37E-23; Nov. 2009; pp. 1-33, and two cover pages.
Murata Manufacturing Co., Ltd.; "Ultrasonic Sensor Application Manual"; Cat. No. 515E-5; Aug. 2009; pp. 1-3, and 2-14, and one supplemental page.
Nature News; "A miniature biofuel cell operating in a physiological buffer"; Nature; Nov. 12, 2002; pp. 1-2; located at: http://www.nature.com/news/2002/021112/full/news021111-1.html.
Ohno et al.; "Graphene Field-Effect Transistors for Label-Free Biological Sensors"; IEEE Sensors 2010 Conference Proceedings; Nov. 1-4, 2010; pp. 903-906; IEEE.
Pacific Northwest National Laboratory; "Juvenile Salmon Acoustic Telemetry System (JSATS) Acoustic Transmitters"; Mar. 2010; pp. 1-2.
Pan et al.; "Development of the real-time pH sensing system for array sensors"; Sensors and Actuators B 108; 2005; pp. 870-876; Elsevier B.V.
Patauner et al.; "High Speed RFID/NFC at the Frequency of 13.56 MHz"; presented at the First International EURASIP Workshop on RFID Technology; Sep. 24-25, 2007; pp. 1-4.
PCT International Search Report; International App. No. PCT/US2013/035993; dated Jun. 25, 2013; pp. 1-2.
PCT International Search Report; International App. No. PCT/US13/36000; dated Jul. 5, 2013; pp. 1-3.
Pushparaj et al.; "Flexible energy storage devices based on nanocomposite paper"; PNAS; Aug. 21, 2007; pp. 13574-13577; vol. 104, No. 34; The National Academy of Sciences of the USA.
Ruhanen et al.; "Sensor-enabled RFID tag handbook"; Building Radio Frequency Identification for the Global Environment; Jan. 2008; pp. 1-47; IST-2005-033546; European Commission.
Sammoura et al.; "Water-activated disposable and long shelf life microbatteries"; Sensors and Actuators A 111; 2004; pp. 79-86; Elsevier B.V.
Sample et al.; "A Capacitive Touch Interface for Passive RFID Tags"; IEEE International Conference on RFID; Apr. 27-28, 2009; pp. 103-109; IEEE.
Sample et al.; "Design of an RFID-Based Battery-Free Programmable Sensing Platform"; IEEE Transactions on Instrumentation and Measurement; Nov. 2008; pp. 2608-2615; vol. 57, No. 11; IEEE.
Sample et al.; "Photovoltaic Enhanced UHF RFID Tag Antennas for Dual Purpose Energy Harvesting"; 2011 International Conference on RFID; Apr. 12-14, 2011; pp. 146-153; IEEE.
Sidén et al.; "The 'Smart' Diaper Moisture Detection System"; IEEE MTT-S Digest, WE4B-3; 2004; pp. 659-662; IEEE.
Stevens et al.; "RuBee (IEEE 1902.1)—The Physics Behind, Real-Time, High Security Wireless Asset Visibility Networks in Harsh Environments"; Sep. 2010; retrieved from web Nov. 17, 2011; pp. 1-6; located at: http://wwx.rubee.com/White-SEC/RuBee-Security-080610.pdf.
Tehrani et al.; "Detection of Monoclonal Antibodies using Chemically Modified Graphite Substrates"; IEEE Sensors 2010 Conference Proceedings; Nov. 1-4, 2010; pp. 428-431; IEEE.
University of Texas Arlington, Office of Technology Management; "Smart Wound Condition Monitoring pH Sensor Array on Flexible Substrate"; Technology Summary; printed on Apr. 12, 2012; pp. 1-2.
Visible Assets; "RuBee Technology, Real-Time Asset Visibility"; printed from web Nov. 17, 2011; pp. 1-3; located at: http://www.rubee.com/Techno/index.html; Visible Assets.
Wang, Wencheng; "A Design Method of Ultrasonic Ranging System with High Accuracy"; Journal of Computational Information Systems; Jul. 2011; pp. 2444-2451; vol. 7, No. 7; Binary Information Press.
Yeager et al.; "Wirelessly-Charged UHF Tags for Sensor Data Collection"; 2008 IEEE International Conference on RFID; Apr. 16-17, 2008; pp. 320-327; IEEE.

\* cited by examiner

WOUND DRESSING MONITORING SYSTEMS INCLUDING APPURTENANCES FOR WOUND DRESSINGS

If an Application Data Sheet (ADS) has been filed on the filing date of this application, it is incorporated by reference herein. Any applications claimed on the ADS for priority under 35 U.S.C. §§ 119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application claims the benefit of the earliest available effective filing date(s) from the following listed application(s) (the "Priority Applications"), if any, listed below (e.g., claims earliest available priority dates for other than provisional patent applications or claims benefits under 35 USC § 119(e) for provisional patent applications, for any and all parent, grandparent, great-grandparent, etc. applications of the Priority Application(s)).

PRIORITY APPLICATIONS

The present application constitutes a continuation-in-part of U.S. patent application Ser. No. 13/445,174, entitled APPURTENANCES FOR REPORTING INFORMATION REGARDING WOUND DRESSINGS, naming Paul Duesterhoft, Nicholas Dykstra, Daniel Hawkins, Roderick A. Hyde, Jordin T. Kare, Eric C. Leuthardt, Elizabeth L. Schubert, Clarence T. Tegreene, and Lowell L. Wood, Jr. as inventors, filed 12 Apr. 2012, which is currently co-pending or is an application of which a currently co-pending application is entitled to the benefit of the filing date, and which is a continuation-in-part of U.S. patent application Ser. No. 13/445,220, entitled COMPUTATIONAL METHODS AND SYSTEMS FOR REPORTING INFORMATION REGARDING APPURTENANCES TO WOUND DRESSINGS, naming Paul Duesterhoft, Nicholas Dykstra, Daniel Hawkins, Roderick A. Hyde, Jordin T. Kare, Eric C. Leuthardt, Elizabeth L. Schubert, Clarence T. Tegreene, and Lowell L. Wood, Jr. as inventors, filed 12 Apr. 2012.

If the listings of applications provided above are inconsistent with the listings provided via an ADS, it is the intent of the Applicant to claim priority to each application that appears in the Domestic Benefit/National Stage Information section of the ADS and to each application that appears in the Priority Applications section of this application.

All subject matter of the Priority Applications and of any and all applications related to the Priority Applications by priority claims (directly or indirectly), including any priority claims made and subject matter incorporated by reference therein as of the filing date of the instant application, is incorporated herein by reference to the extent such subject matter is not inconsistent herewith.

SUMMARY

In some embodiments, an appurtenance to a wound dressing includes: a substrate including a surface of a size and shape to mate with a surface of a wound dressing; a sensor unit affixed to the substrate; an electronic identifier affixed to the substrate; and a transmitter unit operably attached to the sensor unit and to the electronic identifier, the transmission unit including circuitry configured to transmit information associated with the sensor unit and the transmitter unit. In some embodiments, an appurtenance to a wound dressing includes: an enclosure including at least one external surface of a size and shape to mate with a surface of a wound dressing; a sensor unit affixed to the enclosure, the sensor unit configured to sense a condition of the wound dressing; an electronic identifier affixed to the enclosure; and a transmitter unit operably attached to the sensor unit and to the electronic identifier, the transmission unit including circuitry configured to transmit information associated with the sensor unit and the electronic identifier.

In some embodiments, a wound dressing monitoring system includes: an appurtenance to a wound dressing, wherein the appurtenance includes a sensor unit, an electronic identifier, and a transmitter unit operably attached to the sensor unit and to the electronic identifier; and a local unit including a receiver for the transmitter unit, a processor operably attached to the receiver, and a communication unit operably attached to the processor. In some embodiments, a wound dressing monitoring system includes: an appurtenance to a wound dressing, wherein the appurtenance includes a sensor unit including a resonance sensor, an electronic identifier, and a transmitter unit operably attached to the sensor unit and to the electronic identifier; and a local unit including a receiver for the transmitter unit, a processor operably attached to the receiver, and a communication unit operably attached to the processor.

In some embodiments, a method of monitoring a wound dressing includes: accepting a signal by a receiver of a local unit from a transmitter unit of an appurtenance to a wound dressing; processing the received signal into data; classifying a subset of the received data as originating from an electronic identifier of the appurtenance; classifying a subset of the received data as originating from a sensor unit of the appurtenance; comparing the subset of the received data classified as originating from the sensor unit of the appurtenance with data in memory; and initiating a signal to a system user in response to the comparison.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
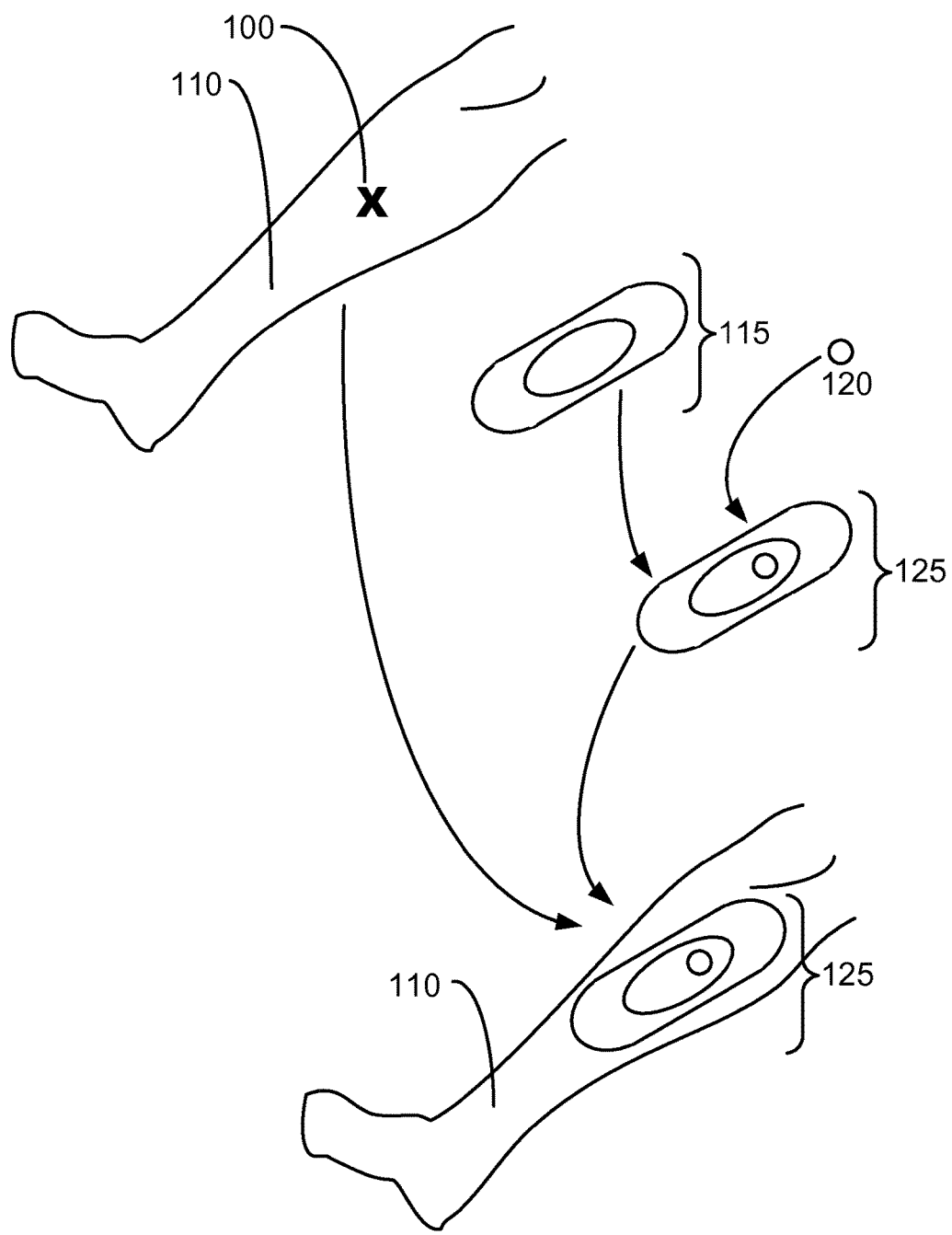
FIG. 1 is an illustration of an appurtenance to a wound dressing in use with a wound.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

The use of the same symbols in different drawings typically indicates similar or identical items unless context dictates otherwise.

With reference now to FIG. 1, shown is an illustration of an appurtenance to a wound dressing in use with a wound that may serve as a context for introducing one or more processes and/or devices described herein. As shown in FIG. 1, a body part 110, such as a leg, includes a wound 100. A wound dressing 115, selected by a medical caregiver as appropriate in size, shape and type for the wound 100, has an appurtenance 120 attached to generate an appurtenance affixed to a wound dressing combination unit, 125. The appurtenance 120 can be attached to the wound dressing 115 with a mechanical attachment. For example, a mechanical attachment can include attachments shaped like prongs, barbs, bristles, spikes, or spurs. The appurtenance 120 can be attached to the wound dressing 115 with a chemical attachment, such as a pressure-sensitive adhesive, a contact adhesive, or a quick-drying adhesive. The appurtenance 120 is a separate and distinct element that can be attached to the wound dressing 115 in a manner sufficient for operation during the use of a specific wound dressing 115. The appurtenance 120 is a separate and distinct element that can be attached to the wound dressing 115 in an irreversible manner. For example, the appurtenance-wound dressing combination unit, 125, can be disposed of after use. Immediate disposal after use can be desirable to minimize biosafety, contamination and biohazard issues. The appurtenance 120 is a separate and distinct element that can be attached to the wound dressing 115 in a reversible manner. For example, the appurtenance-wound dressing combination unit, 125, can be taken apart into its component wound dressing 115 and appurtenance 120 after use. For example, the appurtenance 120 can be configured for reuse with a new wound dressing 115. In some embodiments, an appurtenance includes modular elements suitable for reuse, for example one or more modular sensor units. The appurtenance 120 can be configured for reuse after treatment, such as after disinfection, cleaning, or sterilization. In some embodiments, an appurtenance 120 to a wound dressing 115 can be reused in whole or in part, for example, on a succession of wound dressings 115 used by the same patient.

The appurtenance 120 is configured for functional use only when attached to the wound dressing 115. The appurtenance 120 is designed to function only when attached to a wound dressing 115. The appurtenance 120 is of a size, shape and material for functional use only when attached to the wound dressing 115. The appurtenance 120 is configured to operate in conjunction with the wound dressing 115. The appurtenance 120 is appended to the wound dressing 115 to generate an appurtenance-wound dressing combination unit 125, as illustrated in the lower right region of FIG. 1. In some embodiments, the appurtenance 120 includes at least one region that projects into the structure of the wound dressing 115. In some embodiments, the region that projects into the structure of the wound dressing 115 is of a size and shape to be entirely enclosed within the structure of the wound dressing 115. In some embodiments, the region that projects into the structure of the wound dressing 115 is of a size and shape to project through the wound dressing 115, for example to a region adjacent to a wound. In some embodiments, the region that projects into the structure of the wound dressing 115 is of a size and shape to project through the wound dressing 115, for example to a wound bed region. In some embodiments, the region that projects into the structure of the wound dressing 115 is of a size and shape to project through a portion of the wound dressing 115, for example to a sinus or cavity of the wound bed. In some embodiments, the region that projects into the structure of the wound dressing 115 is of a size and shape to project through a portion of the wound dressing 115, for example to a dressing placed within a sinus or cavity of the wound bed. In some embodiments, the region that projects into the structure of the wound dressing 115 is of a size and shape to project through a portion of the wound dressing 115, for example to a layer placed adjacent to the wound surface. The appurtenance 120 affixed to the wound dressing 115 forms an integrated unit of the appurtenance and the wound dressing as a combination unit 125. In some embodiments, the wound dressing-appurtenance combination unit 125 is not readily separable, and the individual wound dressing 115 and appurtenance 120 are not suitable for separation and individual use after they have been joined together. As illustrated in the lower portion of FIG. 1, once the appurtenance 120 is affixed to the wound dressing 115, the appurtenance and the wound dressing together as a combination unit 125 are used to cover and monitor the wound 100. See also: U.S. patent application Ser. No. 13/445,174, "Appurtenances for Reporting Information Regarding Wound Dressings"; U.S. patent application Ser. No. 13/445,220, "Computational Methods and Systems for Reporting Information Regarding Appurtenances to Wound Dressings"; U.S. patent application Ser. No. 13/491,677, "Dormant to Active Appurtenances for Reporting Information Regarding Wound Dressings"; U.S. patent application Ser. No. 13/795,667, "Appurtenances to Cavity Wound Dressings"; and U.S. patent application Ser. No. 14/252,049, titled "Appurtenances Including Sensors for Reporting Information Regarding Wound Dressings," filed on the same day as the instant application, which are all incorporated herein by reference.

In some aspects, an appurtenance 120 to a wound dressing 115 is configured to monitor one or more aspects of a wound 100. An appurtenance 120 to a wound dressing 115 can be used by a caregiver or a patient to monitor a wound 100. In some aspects, an appurtenance 120 to a wound dressing 115 is configured to monitor one or more aspects of a wound dressing 115. For example, in some embodiments an appurtenance is configured to monitor conditions within a wound dressing, such as from fluid interstitial to the fibers of the wound dressing. In some aspects, an appurtenance to a wound dressing is configured to monitor one or more aspects of a wound dressing environment. For example, in some embodiments an appurtenance to a wound dressing is configured to monitor one or more conditions directly adjacent to the wound dressing, for example at the surface of a wound dressing, and/or at a wound dressing-wound interface. For example, in some embodiments an appurtenance to a wound dressing is configured to monitor one or more conditions in a periwound region. For example, in some embodiments an appurtenance to a wound dressing includes a pressure sensor positioned to detect physical pressure at an interface between a wound dressing and a wound and/or adjacent skin region. For example, in some embodiments an appurtenance to a wound dressing includes a wetness sensor positioned to detect wetness at an interface between a wound dressing and a wound and/or adjacent skin region. For example, in some embodiments an appurtenance to a wound dressing is configured to monitor the interior conditions of a wound dressing, for example fluid saturation, temperature, physical pressure, and/or the presence of one or more specific biological molecules, such as one or more proteins or carbohydrates. In some embodiments an appurtenance to a wound dressing is configured to monitor the interior conditions of a wound dressing with one or more sensors and at least one transmission unit including circuitry configured to transmit information associated with the one or more sensor units. For example, fluid saturation within the fibers of some wound dressings can indicate that the dressing needs to be changed. For example, an excess temperature within a wound dressing can indicate inflammation and/or infection of the adjacent wound tissue in some circumstances. For example, physical pressure on or within the wound dressing can indicate swelling of the adjacent tissue, excess fluid within the wound dressing, and/or a constriction to the wound dressing that should be addressed. For example, the presence of one or more biological molecules specific to a bacterial species may indicate the presence of the bacteria species in the wound dressing propagated from an infection in the wound.

An appurtenance 120 to a wound dressing 115 can be used by a caregiver, including a patient, to monitor a wound dressing 115. An appurtenance 120 to a wound dressing 115 is configured to allow a user, such as a caregiver or patient, to monitor a wound dressing and the adjacent wound without disturbing the wound dressing 115 such as through removing the dressing 115 from the patient's wound 100. This approach, inter alia, improves comfort to the patient, reduces the chance of accidental infection in or contamination from uncovered wounds, and minimizes time requirements in wound care. In some aspects, an appurtenance 120 to a wound dressing 115 includes a transmitter that sends a signal to a device used by a caregiver or patient to monitor the wound dressing from the same room as the patient. In some aspects, an appurtenance 120 to a wound dressing 115 includes a transmitter that sends a signal to a device used by a caregiver remotely, such as through a pager, remote computing device, cell phone, or dedicated remote signaling device. The signal transmitter sends a signal containing information associated a wound and/or adjacent wound dressing such that a caregiver is able to receive, directly or indirectly, information relating to monitoring a wound and adjacent wound dressing at a distance from the patient, without disturbing the patient and with minimal time spent analyzing the wound 100 or wound dressing 115.

In some aspects, an appurtenance to a wound dressing is part of a system configured to automatically process and save information relating to an appurtenance and the related wound dressing to a medical record system, such as a medical records database. In some aspects, an appurtenance to a wound dressing is part of a system configured to automatically process and save information relating to an appurtenance and the related wound dressing to an electronic health record. An automatic process reduces the potential for accidental loss or error in data entry regarding wound care, and reduces the time required by a caregiver in data entry into a record.

As shown in FIG. 1, the wound dressing with the affixed appurtenance combination unit 125 is used to cover the wound 100 on the body part 110. The wound dressing with the affixed appurtenance combination unit 125 can be secured to the body part 110 in a routine manner for the type of wound dressing 115 generally, such as through adhesive integral to the wound dressing 115 or with additional adhesive, wrappings, tapes or glues as generally applicable to the type of wound dressing 115 utilized in a given medical situation. Although not illustrated in FIG. 1, the wound dressing with the affixed appurtenance combination unit 125 can similarly be removed using standard removal procedures, such as with gentle pressure, gentle pulling, unwrapping, allowing it to loosen over time, or bio-compatible solvents. The appurtenances 120 described herein can be single-use and disposable along with the affixed wound dressing 115. In some embodiments, the appurtenances 120 described herein can be removed from a first wound dressing and then reconditioned in whole or in part, such as through cleaning or sterilization, and reused with a second wound dressing. In some embodiments, an appurtenance 120 can be reused for multiple wound dressings used on a single wound from a patient. The appurtenances 120 described herein are generally intended to be operable for the period of time a given wound dressing 115 is in use under standard conditions and time periods. After the wound dressing with the irreversibly affixed appurtenance combination unit, 125 is removed from the body part 110, it can be disposed of as a unit with routine disposal methods.

It is envisioned that the appurtenances described herein will be utilized while affixed to wound dressings over wounds of a variety of types, and operable to assist in the monitoring of wounds of a variety of types. For example, appurtenances can be used in conjunction with wound dressings to assist in monitoring acute wounds, such as those resulting from accidental injury or surgery. For example, appurtenances can be used in conjunction with wound dressings to assist in monitoring wounds closed by primary intention. For example, the appurtenances can be used to assist in monitoring wound dressings over surgical wounds, such as incisions and surgical stitches. For example, the appurtenances can be used to assist in monitoring wound dressings over acute wounds from injury, such as burn injuries, lacerations, or penetrating wounds. For example, appurtenances can be used in conjunction with wound dressings to assist in monitoring wounds closed by secondary intention. The appurtenances can also be used to assist in monitoring wound dressings over chronic wounds, such as those arising from chronic medical conditions and situations. For example, the appurtenances can be used to monitor the status of wound dressings covering venous leg ulcers, diabetic foot ulcers, pressure ulcers or arterial ulcers. See: "Advances in Wound Healing Techniques," publication D11A, Frost and Sullivan, 2008; "An Overview of Ulceration Wounds," Publication M4BB-54, Frost and Sullivan 2009; and "US Advanced Wound Care Market," Publication N71A-54, Frost and Sullivan 2010, which are each incorporated herein by reference. In some embodiments, appurtenances can be used in conjunction with wound dressings for oral wounds.

The appurtenances described herein can be useful in conjunction with an affixed wound dressing as a combination unit to monitor potential problems with a wound, such as excessive bleeding or other fluid formation that would be present in the wound dressing, or the presence of conditions in the dressing that indicate infection in an adjacent wound. See: Collier, "Recognition and Management of Wound Infections," *World Wide Wounds*, pages 1-9, (January 2004); Gray, "Assessment, Diagnosis and Treatment of Infection," *Wounds UK*, vol. 7, no. 2, supplement, (2011); and Mehmood et al., "Review Article: Applications of Modern Sensors and Wireless Technology in Effective Wound Management," *J Biomed Mater Res part B*, published online DOI: 10.1002/jbm.b.33063 (2013) which are each incorporated herein by reference. For example, some types of wound discharge can indicate infection. See, for example, Cutting and Harding, "Criteria for Identifying Wound Infection," *Journal of Wound Care*, vol. 3, no. 4, 198-201 (1994), which is incorporated herein by reference. The appurtenances as part of combination units 125 and related systems described herein can be used in conjunction with readily available types of wound dressings to monitor aspects of the affixed wound dressing, including parameters that indicate that a person should physically examine the wound dressing, such as excessive wetness, dryness, an elapsed period of time, or the presence of specific factors detected by one or more sensors of the appurtenance. The appurtenances as well as related systems described herein can be used in conjunction with readily available types of wound dressings to monitor aspects of the affixed wound dressing, including indications that the wound dressing should be changed (i.e. excessively wet, dry, or soiled).

The appurtenances described herein include transmission units configured to transmit signals, and thereby report information regarding the status of the affixed wound dressing or wound, to associated systems. The resulting information reporting can be used, in some embodiments, to supplement the medical record for a patient in an automated system and automatic process. The resulting information reporting can be used, in some embodiments, to automatically notify a caregiver that the status of the wound dressing has altered, indicating that a person should physically inspect the wound dressing.

As used herein, a caregiver includes at least one of a patient, a caregiver, and medical personnel. A caregiver can utilize some embodiments of the appurtenances and related systems described herein in relation with multiple types of wound dressings. Appurtenances can be fabricated in shapes and sizes to conform to a variety of standard wound dressing sizes, shapes and types. Appurtenances can be fabricated with, for example, transmission units, antennas and sensors appropriate for use with a variety of wound dressings. Appurtenances can be fabricated with, for example, transmission units, antennas and sensors appropriate for different medical situations and monitoring requirements. Appurtenances can be fabricated with, for example, one or more projections of a size, shape and material appropriate for use with a variety of wound dressings. While it is envisioned that every appurtenance will not be appropriate for use with every wound dressing (for example due to size, shape or material compatibility), a given appurtenance is expected to be suitable for use with a range of potential wound dressings. For example, a given appurtenance of a specific size, shape and fabrication, including type of transmission unit, sensors, and projection(s), should be suitable for use with a variety of wound dressings of conforming sizes, shapes and types. Generally, any specific appurtenance embodiment is not expected to only conform to use with a unique wound dressing of a specific size, shape and type. Instead, it is expected that a specific appurtenance embodiment will be suitable for use with a range of wound dressings. Similarly, it is expected that a specific appurtenance embodiment will be suitable for use with a range of wound and wound dressing monitoring requirements.

In the attached drawings, an appurtenance 120 is often illustrated as affixed to an outer surface of a wound dressing 115, for example an outer surface distal to a surface of the body part 110 adjacent to the wound 100. However, in some embodiments, an appurtenance 120 can be configured to attach to one or more surfaces of a wound dressing 115 adjacent to a surface of the body part 110 adjacent to the wound 100. For example, in embodiments wherein an appurtenance 120 is configured to be attached to a wound dressing 115 of a substantially rectangular, ovoid, or raised conformation, an appurtenance 120 can be configured to be attached to a side surface of the wound dressing 115. For example, in embodiments wherein an appurtenance 120 is configured to be attached to a wound dressing 115 with an unusually strong or thick outer cover layer, the appurtenance 120 can be configured to attach to an underside of the wound dressing 115. In some embodiments, an appurtenance is configured to attach to a surface of a wound dressing 115 in contact with the surface of the body part 110.

For example, the appurtenances described herein can be configured to be affixed to a dry gauze dressing, which may or may not include an outer cover layer. For example, the appurtenances described herein can be configured to be attached to a dry silicone or other solid foam dressing, which may or may not include an outer cover layer. For example, the appurtenances described herein can be configured to be affixed to a wound dressing used to close a small or thin wound or surgical incision, such as a butterfly dressing (e.g. SteriStrip™ adhesive strips, available from Nexcare™, part of 3M Corporation). For example, appurtenances such as those described herein can be configured to be affixed to a dressing configured to maintain moisture or other materials adjacent to the wound surface. For example, appurtenances such as those described herein can be configured to be used with hydrogel wound dressings, for example Aquaflo™ Hydrogel Wound Dressing by Kendall Corporation, or Elasto-Gel™ Hydrogel Occlusive Dressing by Southwest Technologies. For example, appurtenances such as those described herein can be affixed to wound dressings including hydrocolloids, for example DuoDERM CGF Sterile Hydrocolloid Dressing manufactured by DuoDERM Corporation. For example, appurtenances such as those described herein can be configured to be used with wound dressings containing one or more medicinal agents, such as antibiotics. For example, appurtenances such as those described herein can be used with wound dressings impregnated with PHMB (Polyhexamethylene Biguanide), such as Telfa™ A.M.D. antimicrobial wound dressings, manufactured by Kendall Corporation. For example, appurtenances such as those described herein can be configured to be used with wound dressings including ionic silver, such as Maxorb™ Extra Ag wound dressings manufactured by Medline Corporation. Appurtenances such as those described herein can be configured to be affixed to wound dressings over wounds wherein the tissue of the wound is being directly monitored using other devices, for example as described in U.S. Pat. No. 6,963,772 to Bloom et al., titled "User-retainable Temperature and Impedance Monitoring Methods and Devices," which is incorporated herein by reference. Appurtenances such as those described herein can be configured to be affixed to wound dressings over wounds wherein the patient is being directly monitored using other devices, for example as described in U.S. Pat. No. 7,030,764 to Smith and Cooper, titled "Apparatus and Method for Reducing the Risk of Decubitus Ulcers;" U.S. Pat. No. 7,297,112 to Zhou et al., titled "Embedded Bio-Sensor System;" U.S. Pat. Nos. 7,372,780, 8,014,234 and 7,813,226 to Braunberger, titled "Timing System and Device and Method for Making the Same;" U.S. Pat. No. 7,666,151 to Sullivan et al., titled "Devices and Methods for Passive Patient Monitoring;" U.S. Pat. No. 7,703,334 to Cochran, titled "Bandage Type Sensor Arrangement and Carrier Assembly Therefore, and Method of Manufacture;" and International Patent Publication No. WO 2005/009328 to Nikolic, titled "ABT-Anti-Bedsore Timer," which are each incorporated herein by reference. Appurtenances such as those described herein can also be used in conjunction with a system to monitor assets within a health care facility, for example as described in US Patent Application No. 2007/0247316 to Wildman et al., titled "Article Locating and Tracking Apparatus and Method," which is incorporated herein by reference.

Wound dressings such as those described herein are generally used for a relatively short period of time, on the order of hours or days, and then removed for disposal. Similarly, a wound dressing with an affixed appurtenance combination unit should be configured for use over the course of hours or days and then removed and disposed of using standard methods. A wound dressing with an affixed appurtenance is single use and disposable after use. For example, a caregiver can require a new wound dressing every 24 hours (1 day) for an acute wound. Any wound dressing utilized in this type of situation would, consequently, be of a size and shape to remain affixed to the wound region over the course of at least a 24 hour period and then removed for disposal. An appurtenance to a wound dressing intended for use over the course of a 24 hour time period, similarly should be of a size, shape, material fabrication, and capabilities to function while affixed to the wound dressing over the 24 hour period that the dressing is in use. As an additional example, a caregiver can decide that for another type of wound, such as a chronic wound, the wound dressing needs to be removed and replaced once every 3 days, or every 4 days, or every 5 days, or every 6 days, or every 7 days. Correspondingly, an appurtenance affixed to a wound dressing intended for use over the course of at least 3 to 7 days should be of a size, shape, material fabrication, and capabilities to function while affixed to the wound dressing over at least the 3 to 7 day period that the dressing is in use. In embodiments wherein an appurtenance is intended for reuse, such as reuse on a second or subsequent wound dressing used over a wound, the appurtenance should be of a size, shape, material fabrication and capabilities to function during the entire intended use, including the time period of removal from a first wound dressing and application to a second wound dressing, as well as any intermediate refurbishment or cleaning process.

In some embodiments, an appurtenance to a wound dressing includes: a substrate including a surface of a size and shape to mate with a surface of a wound dressing; a sensor unit affixed to the substrate; an electronic identifier affixed to the substrate; and a transmitter unit operably attached to the sensor unit and to the electronic identifier, the transmission unit including circuitry configured to transmit information associated with the sensor unit and the transmitter unit. Some embodiments of an appurtenance include a battery unit. For example, a battery unit can be affixed to a substrate and connected to a transmitter unit. In some embodiments, a battery unit is modular, and configured for removal and replacement. For example, a battery unit can be affixed to a substrate with one or more reversible fasteners. In some embodiments, a battery unit is integral to another unit. For example, a battery unit can be integral to a transmitter unit. For example, a battery unit can be integral to a sensor unit. For example, a battery unit can be integral to an electronic identifier.

Figure 2:
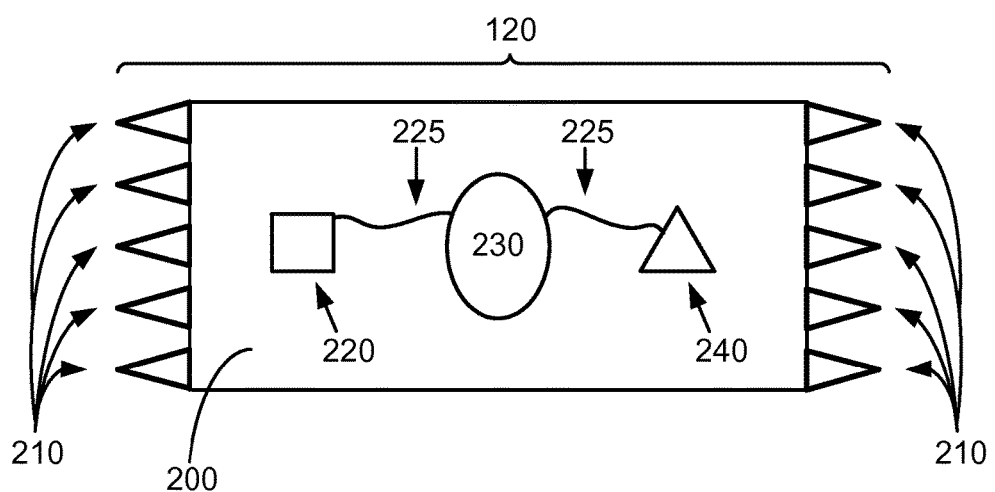
FIG. 2 is a schematic of an appurtenance to a wound dressing.

FIG. 2 depicts aspects of an embodiment of an appurtenance 120. The embodiment of an appurtenance 120 shown in FIG. 2 includes a substrate 200 that is a substantially planar structure. The appurtenance 120 in FIG. 2 is depicted to illustrate aspects of one of the largest faces of the appurtenance, or an approximately "top-down" view of the appurtenance as it might be used in conjunction with a wound dressing. The embodiment illustrated in FIG. 2 includes a sensor unit 220 attached to the substrate. Some embodiments include one sensor unit. Some embodiments include two, three, four, five or more than five sensor units. In some embodiments, the one or more sensor units attached to the substrate are directly attached to the substrate. In some embodiments, the one or more sensor units attached to the substrate are indirectly attached to the substrate, such as within a frame or similar structure with reversible fasteners for sensor units that are modular. In some embodiments, the one or more sensor units are attached to the substrate within an interior region of the substrate. For example, the substrate can include two or more walls and one or more sensor units can be affixed within a region between the walls. For example, the substrate can include two or more planar sheets and one or more sensor units can be affixed within a region between the planar sheets. Some embodiments include at least one wire connector positioned between each of the one or more sensor units and the transmission unit. Some embodiments include: at least one wire connector positioned between a sensor unit and a transmission unit; and at least one wire connector positioned between an electronic identifier and a transmission unit. The sensor unit 220 illustrated in FIG. 2 is connected to a transmission unit 230 with a wire connector 225. Aspects of the appurtenance that are illustrated in FIG. 2 may be covered up or obscured in some embodiments. For example, in some embodiments an appurtenance includes a cover that would obscure sensor unit 220 and transmission unit 230 as well as associated wire connectors 225.

Some embodiments include a plurality of projections affixed to the substrate. The appurtenance 120 shown in FIG. 2 includes a first end with a first set of the plurality of projections 210 attached to the first end of the substrate 200, and a second end, with a second set of the plurality of projections 210 attached to the second end of the substrate 200. In the view shown in FIG. 2, the left side of the appurtenance 120 can be considered as a "first end" and the right side of the appurtenance 120 can be considered as a "second end" for purposes of illustration. The plurality of projections 120 are collectively referred to as "projections 210" with reference to the figures herein. The projections 210 are each substantially conical structures, with a wide end affixed to the end of the substrate 200 and a narrow end positioned distal to the substrate 200. In some embodiments, each of the projections 210 include a proximal end and a distal end, with the projections 210 tapering in size from the proximal end to the distal end. In some embodiments, the plurality of projections extend outward along a largest linear dimension of the substrate. For example, in the embodiment shown in FIG. 2, the projections extend outward in substantially the same plane as the largest plane of the substrate.

Depending on the embodiment, the projections can project in one or more directions substantially away from the surface of the appurtenance configured to conform with an outer surface of the wound dressing, or angle in a direction substantially perpendicular to the surface configured to conform with an outer surface of the wound dressing of the appurtenance. Some embodiments include a projection affixed to the substrate, the projection positioned to affix the surface of the substrate to the surface of the wound dressing. Some embodiments include at least one projection which is curvilinear. Some embodiments include at least one projection which is a composite shape. In embodiments including one or more projections that are not substantially straight, an angle (e.g. θ) of the projection can be determined by the angle formed at the base of the projection immediately adjacent to the surface of the appurtenance configured to conform with an outer surface of the wound dressing.

A projection can be a substantially hollow tubular structure. A substantially hollow tubular structure of a projection can include an opening on the distal end of the projection. In some embodiments projections can be of different shapes and conformations. For example, a projection can be solid, tubular, conical, cylindrical, tapered, curved, angular or other shape or combination of shapes as appropriate to the specific embodiment. Embodiments including a plurality of projections can include projections of different sizes and shapes. A projection can be substantially straight and form a substantially linear internal channel, or it can be curved and form a substantially curvilinear internal channel. The drawings illustrated herein are not to scale. The drawings illustrated herein represent relationships and shapes of the items described. Although not expressly illustrated herein, a projection can be relatively large relative to the total size of the appurtenance. For example, the volume of a projection or a group of projections attached to an appurtenance can be 51%, 55%, 60%, 65%, 70%, 75%, 80%, 85%, 90%, 95% or 100% of the volume of the portion of the appurtenance configured to conform with an outer surface of a wound dressing. Similarly, a projection can be relatively small relative to the total size of the appurtenance. For example, the volume of a projection or a group of projections attached to an appurtenance can be 49%, 45%, 40%, 35%, 30%, 25%, 20%, 15%, 10%, or 5% of the volume of the portion of the appurtenance configured to conform with an outer surface of a wound dressing. In some embodiments, a projection is located at an edge region of the substantially planar region of the appurtenance, and in some embodiments a projection is located substantially centrally to the planar surface of the appurtenance configured to conform with an outer surface of the wound dressing. In some embodiments, a substantially planar appurtenance includes at least one projection wherein the entire appurtenance is of a size and shape to be secured against an external surface of a wound dressing with force, for example from a human thumb or finger.

FIG. 2 depicts a transmission unit 230 attached to the approximate center of the plane of the substrate 200. The transmission unit 230 is affixed to the substrate 200. A wire connector 225 operably connects the sensor unit 220 to the transmission unit 230. The appurtenance 120 includes an electronic identifier 240 attached to the substrate 200. A wire connector 225 operably connects the electronic identifier 240 to the transmission unit 230.

An "electronic identifier," as used herein, refers to a unit that includes a specific electronic code or similar identifier. In some embodiments, an electronic identifier is a RFID identifier code. In some embodiments, an electronic identifier includes an RFID unit. In some embodiments, an electronic identifier is an alphanumeric identifier code. In some embodiments, an electronic identifier is a computer code. For example, in some embodiments an electronic identifier is a self-contained unit that attaches to a surface of the substrate and sends signals to the transmission unit that includes one or more electronic codes that identify a specific appurtenance. An electronic identifier of an appurtenance can include an identifier code specific for an individual appurtenance. For example, an electronic identifier can include a code that includes a unique identifier code that is associated with a specific and unique appurtenance. The electronic identifiers can be associated, for example, with information in a look-up table that connects information about an appurtenance with a unique identifier code. The electronic identifiers can be associated, for example, with information in a database that connects information about an appurtenance with a unique identifier code. For example, an electronic identifier can be associated with information such as a particular patient, a date, a time, a user, and/or a location. An electronic identifier of an appurtenance can include an identifier code that includes subparts identifying aspects of the appurtenance. For example, an electronic identifier can include a code that includes subparts denoting the make, model, place of manufacture, date of manufacture, and manufacture line of a specific appurtenance. In some embodiments, an electronic identifier includes an electronic code.

In some embodiments, an appurtenance can be fabricated with one or more regions configured for the attachment of different modules. In some embodiments, an appurtenance includes modules that are configured for removal and replacement. For example, some embodiments include appurtenances with removable and replaceable sensor units. During fabrication, a basic appurtenance structure can be utilized and different specific modules added as desired in a particular embodiment. For example, an appurtenance can be fabricated with at least one region configured to attach a projection. For example, a region configured to attach a projection can include a region with a surface conforming to an outer surface of the projection. For example, a region configured to attach a projection can include a conduit configured to align with the hollow interior of the projection. The region of the appurtenance configured to attach a projection can be configured for attachment of different projection types, depending on the embodiment. For example, the region of the appurtenance configured to attach a projection can be configured for attachment of projections of different lengths or different materials as desired in the construction of a particular embodiment. In some embodiments, an appurtenance can have multiple regions configured for attachment of multiple projections of different types. In some embodiments, an appurtenance can have one or more removable antenna modules. In some embodiments, an appurtenance can have one or more removable sensor unit modules. For example, an appurtenance can have one or more removable power source modules, such as batteries or solar cells. In some embodiments, a module can include a spacer element, or a component configured to assist in physically positioning one or more other modules.

In some embodiments, an appurtenance includes a barrier layer, such as a thin film, positioned between the substrate of the appurtenance and one or more modules of the appurtenance. See: U.S. Pat. No. 7,914,867, "Medical Gas Barrier Film and Medical Bag Using the Same" to Mori et al.; and U.S. Pat. No. 5,939,205 "Gas Barrier Resin Film" to Yokoyama et al., which are each incorporated by reference. In some embodiments, an appurtenance includes a barrier layer, such as a thin film, positioned between the enclosure of the appurtenance and one or more modules of the appurtenance. The barrier layer can be positioned, for example, between the substrate of an appurtenance and one or more removable and replaceable modules, such as sensor units. The barrier layer can, for example, reduce the possibility of biological contamination spread within an appurtenance, or between components of an appurtenance, such as between sensor units. In some embodiments, a barrier layer is positioned within an interior region of an enclosure of an appurtenance, for example adjacent to an interior surface of the enclosure. In some embodiments, a barrier layer is positioned within an interior region of an enclosure of an appurtenance, for example affixed to an interior surface of the enclosure. A barrier layer can be positioned to reduce the potential for contamination of a modular component of an appurtenance, for example partially or entirely surrounding a removable sensor unit.

In some embodiments, an appurtenance includes a fluid control material, such as a fluid control film, positioned to permit directional flow of a liquid from a position external to the appurtenance to an internal region of the appurtenance, such as a position adjacent to a sensor unit. See U.S. Pat. No. 6,420,622 to Johnston et al. "Medical Article Having Fluid Control Film," which is incorporated herein by reference. For example, some embodiments include a fluid control film within a conduit or aperture in a substrate of an appurtenance, the fluid control film positioned to direct fluid flow from a wound dressing into an interior region of the substrate, such as through an internal conduit and/or to a sensor unit. For example, some embodiments include a fluid control film within a conduit or aperture in an enclosure of an appurtenance, the fluid control film positioned to direct fluid flow from a wound dressing into an interior region of the enclosure, such as to a sensor unit. For example, some embodiments include a fluid control film within a conduit or aperture in a projection of an appurtenance, the fluid control film positioned to direct fluid flow from a wound dressing through an interior region of the projection and to a connected sensor unit. For example, some embodiments include a fluid control film within a conduit or aperture in a projection of an appurtenance, the fluid control film positioned to direct fluid flow from a wound dressing through an interior region of the projection and to a connected transmission unit. In some embodiments, an appurtenance includes a fluid control film positioned to permit directional flow of a liquid from a position external to the appurtenance to an internal region of the appurtenance, such as a position adjacent to a sensor unit.

An appurtenance can be fabricated from a variety of materials, as appropriate to an embodiment. An appurtenance can be fabricated, for example, substantially from a plastic material. For example, a structural portion, such as a substrate, enclosure, shell or base can be fabricated from a plastic material. For example, one or more projections can be fabricated from a plastic material. An appurtenance can be fabricated, for example, from one or more acrylics, polyesters, silicones, polyurethanes and/or halogenated plastics. An appurtenance can include one or more projections fabricated, for example, from one or more plastic materials. An appurtenance can include one or more projections fabricated, for example, from one or more acrylics, polyesters, silicones, polyurethanes and/or halogenated plastics. An appurtenance can be fabricated from one or more bio-compatible materials, for example bio-compatible plastics, resins, epoxies and metals. An appurtenance can be fabricated from one or more materials to achieve a level of flexibility of the appurtenance relevant to a specific use, for example an appurtenance can be fabricated from substantially rigid materials or substantially flexible materials, or a combination thereof to achieve a particular flexibility of an appurtenance as required for a specific embodiment. An appurtenance can be fabricated from one or more composite materials, such as plastic with an overlay of epoxy or plastic with an overlay of one or more metals. An appurtenance including a transmission unit can include, for example, one or more metal components, for example as circuitry or as one or more antennas. An appurtenance including a transmission unit can include, for example, stainless steel, copper or zinc alloy. An appurtenance can be fabricated from one or more ceramic materials, such as within a transmission unit. Generally, it is envisioned that materials with low weight will be suitable for a variety of appurtenance embodiments, so as to reduce weight and associated physical stress on a wound dressing. Similarly, it is envisioned that materials with sufficient strength and toughness to be fabricated into small and thin components will be desirable for fabrication of appurtenance embodiments. As the appurtenances are to be affixed to wound dressings, bio-compatible materials can be preferred. As the appurtenances are to be affixed to wound dressings and, in some embodiments, disposed of with the wound dressings, materials that do not require special handling or disposal are preferable in most embodiments.

In some embodiments, the appurtenance includes a substrate or enclosure that is configured to attach to the wound dressing. For example, the substrate or enclosure can be configured as a support for other features of the appurtenance. In some embodiments, the substrate includes a substantially planar structure wherein the area of surface is less than the area of the wound dressing. In some embodiments, the substrate or enclosure is configured to irreversibly attach directly to an external surface of the wound dressing. For example, some embodiments include: a substantially planar structure; and a fastener of a size and shape to affix the surface of the substrate to the surface of the wound dressing. In some embodiments, the substrate or enclosure includes an adhesive on a surface conforming to an external surface of the wound dressing. For example, the surface conforming to an external surface of a wound dressing can include a glue, epoxy, sealant, mucilage, paste or other binder material. In some embodiments, the substrate or enclosure includes at least one chemical adherent positioned to affix the substrate or enclosure to a wound dressing. For example, some embodiments include: a medically-compatible adhesive positioned on the surface of the substrate in an orientation to adhere the surface of the substrate to the surface of the wound dressing. In some embodiments, the surface of the substrate or enclosure conforming to an external surface of a wound dressing can include an adhesive covered by a removable protective sheet configured for detachment and exposure of the adhesive when the appurtenance is attached to the wound dressing. In some embodiments, the surface of the substrate or enclosure of the appurtenance configured to conform with an outer surface of the wound dressing can include barbs, hooks, pins, prongs or other extensions configured to adhere or fix into the outer surface of the wound dressing. In some embodiments, the surface of the substrate or enclosure of the appurtenance configured to conform with an outer surface of the wound dressing can include a mixture or combination of any of the above.

In some embodiments, the substrate or enclosure of an appurtenance includes a flexible material. For example, the substrate or enclosure of an appurtenance can include a pliable plastic, a woven fabric material, soft mesh or other flexible material. In some embodiments, the substrate or enclosure of an appurtenance includes a rigid material. For example, the substrate or enclosure of an appurtenance can include at least one rigid plastic material in a location configured to provide support for a portion of the appurtenance. For example, the substrate can include at least one rigid plastic material at a location configured to attach a projection, the rigid plastic configured to provide physical support for the attached projection. In some embodiments, the substrate or enclosure of an appurtenance includes at least one bio-compatible material. For example, the substrate or enclosure of an appurtenance can include one or more bio-compatible plastic materials, one or more bio-compatible fabric materials, or one or more bio-compatible metals.

In some embodiments, an appurtenance to a wound dressing is substantially sterilized prior to use and the appurtenance is fabricated from materials that are known to be stable under the expected sterilizing conditions. For example, the appurtenance can be treated with one or more chemical disinfectants or UV surface radiation for a period of time sufficient to substantially sterilize the appurtenance prior to use. For example, the appurtenance can be treated with one or more antimicrobial gasses, for example ethylene oxide (ETO), prior to use. For example, the appurtenance can be treated with a chemical sterilizing agent, such as hydrogen peroxide in liquid or vapor form, prior to use. For example, the appurtenance can be treated with steam as an anti-infective prior to use. For example, the appurtenance can be treated with heat prior to use. For example, the appurtenance can be treated with gamma irradiation prior to use. For example, the appurtenance can be treated with electron irradiation prior to use. In some embodiments, one or more components of an appurtenance, for example a sensor unit, a substrate, or an enclosure, are fabricated from one or more materials known to be physically stable after multiple sterilizing treatments. In some embodiments, an appurtenance to a wound dressing includes a sterile wrapper. For example, an appurtenance to a wound dressing can be stored and/or transported within a sterile wrapper, such as a firm paper wrapper or a plastic film. A sterile wrapper configured for storage and/or transport of an appurtenance can be treated to minimize contamination, for example coated with one or more anti-microbial agents. In some embodiments a wound dressing monitoring system includes a wrapper sealed to protect the cleanliness and/or sterility of the wound monitoring system.

Appurtenances include one or more sensor units. Each sensor unit includes at least one sensor. In some embodiments, a sensor unit includes more than one sensor, for example, two sensors, three sensors or four sensors in a single sensor unit. A sensor unit can include, for example, two or more sensors of a specific type. Some embodiments include a sensor unit including at least two sensors of different types. A sensor unit can include, for example, two or more sensors wherein each of the sensors is configured to sense a different parameter, for example including different antibodies or aptimers configured to bind with distinct target proteins. Sensor units can include sensors specific for detection of specific proteins, or related protein families (e.g. MMPs). A sensor unit can be configured to detect one or more conditions of a wound dressing, such as temperature, pressure, fluid saturation, and/or fluid level within the interior of the wound dressing. A sensor unit can be configured to detect one or more biological molecules present in a wound dressing, such as biological molecules arising from one or more bacteria, biological molecules arising from one or more viruses, biological molecules arising from the wound, and/or biological molecules arising from tissue adjacent to the wound.

A variety of sensors can be utilized in different embodiments of the appurtenances, depending on factors such as the intended use of the appurtenance, size, weight, cost, biocompatibility, safety and ease of disposal. "Sensors," as used herein, can be of a variety of types depending on the embodiment. One or more sensors can include a chemical sensor. For example, one or more sensors can include a sensor that relies on a chemical change, such as a chemical reaction, as part of the detection process. One or more sensors can include at least one sensor responsive to changes in capacitance, or a measure of the ability of a configuration of materials to store electric charge. A general review of biosensors that detect changes in the dielectric properties of an electrode surface can be found in Berggren et al., "Capacitive Biosensors," *Electroanalysis* vol. 13, no. 3, 173-180, (2001), which is incorporated herein by reference. For example, one or more sensors can include a micromechanical biosensor with a fixed-fixed beam attached to an interdigitated capacitor (see, for example, Lim et al., "A Micromechanical Biosensor with Interdigitated Capacitor Readout," *Proceedings of the* 2011 *IEEE/ICME International Conference on Complex Medical Engineering*, May 22-25, Harbin, China, which is incorporated herein by reference). Sensors can also include nanowire nanosensors, for example as described in Cui et al., "Nanowire Nanosensors for Highly Sensitive and Selective Detection of Biological and Chemical Species," *Science*, vol. 293, 1289-1292 (2001), which is incorporated herein by reference. Sensors can include those utilizing antibodies secured to a graphene substrate. See Tehrani et al., "Detection of Monoclonal Antibodies using Chemically Modified Graphite Substances," *IEEE Sensors* 2010 *Conference Proceedings,* 428-431, (2010), which is incorporated herein by reference. In some embodiments, sensors include aptamer-modified graphene field-effect transistors, see Ohno et al., "Graphene Field-Effect Transistors for Label-Free Biological Sensors," *IEEE Sensors* 2010 *Conference Proceedings,* 903-906, (2010), which is incorporated herein by reference. A sensor in an appurtenance can interact with a sensor present in a wound dressing, for example as described in U.S. Pat. No. 6,283,938 to McConnell, titled "Medicating Bandage and Controllable Permeable Membrane," which is incorporated herein by reference. A sensor can include a field effect transistor (FET), such as described in U.S. Pat. No. 7,507,675 to Zuilhof et al., titled "Device Manufacturing Method and Device," which is incorporated herein by reference. A sensor can include a nano-cantilever device, such as described in U.S. Pat. No. 7,612,424 to Espinosa and Ke, titled "Nanoelectromechanical Bistable Cantilever Device," which is incorporated herein by reference. In some embodiments, sensors include temperature sensors, which can be included in the sensor units along with a different type of sensor (e.g. a micromechanical biosensor). In some embodiments, sensors include moisture sensors, positioned to detect the level of moisture present in a wound dressing. A moisture sensor can include, for example, a capacitance-based moisture sensor. In some embodiments, sensors include resonance sensors, positioned to detect changes in resonance of a sensor unit in proximity to a wound dressing relative to the amount of fluid in the wound dressing (i.e. the "wetness" of the dressing). In some embodiments, sensors include resonance sensors, positioned to have altered internal resonance, such as within a cavity resonator of the sensor, relative to the fluid saturation of the wound dressing.

In some embodiments, a sensor unit includes a pressure sensor. For example, a pressure sensor can be positioned to detect the physical pressure on a wound dressing, such as from swelling of the dressing or against the surface of the dressing. In some embodiments, sensors include pressure sensors, positioned to detect physical pressure on the wound dressing from an external source, such as a bandage wrap or cover. In some embodiments, sensors include pressure sensors, positioned to detect physical pressure in the interface between a surface of the wound dressing and the wound and/or adjacent skin of the patient. In some embodiments, a sensor unit includes a temperature sensor. In some embodiments, a sensor unit includes both a pressure sensor and a temperature sensor. See, for example, DeHennis and Wise, "A Wireless Microsystem for the Remote Sensing of Pressure, Temperature, and Relative Humidity," *Journal of Microelectromechanical Systems*, 14(1): 12-22 (2005), which is incorporated by reference herein. In some embodiments, a sensor unit includes a sensor configured to detect one or more aspects of a fluid within the wound dressing and/or positioned adjacent to the wound dressing. In some embodiments, a sensor unit includes a sensor configured to detect one or more aspects of a gas within the wound dressing or positioned adjacent to the wound dressing. In some embodiments, a sensor unit includes a pH sensor. In some embodiments, a sensor unit includes a detector of a specific chemical, such as nitric oxide. In some embodiments, a sensor unit includes a detector of a specific biological agent, such as a bacterial protein. In some embodiments, a sensor unit includes a sensor including at least one aptimer. In some embodiments, a sensor unit includes a sensor including at least one antibody. In some embodiments, a sensor unit includes a plurality of sensors within the sensor unit. Some embodiments include a sensor unit including: a sensor; circuitry for accepting data from the sensor; circuitry for processing the accepted data; and circuitry for sending the processed data to the transmission unit. Some embodiments include a sensor unit with reversible fasteners of a size and shape for attachment to the substrate. For example, an appurtenance can be configured to attach one or more modular sensor units.

Some sensors within sensor units such as those described herein can be configured to sense fluids. Some sensors within sensor units such as those described herein can be configured to sense one or more components of a fluid. Some sensors within sensor units such as those described herein can be configured to sense one or more analytes within a fluid. As used herein, fluid includes both gasses and liquids individually or as mixtures. Some sensors within sensor units described herein can detect fluids, whether in gaseous state or liquid state. If the fluid is a liquid, it can be drawn into an appurtenance through capillary action. If the fluid is a gas, it can be drawn into the appurtenance through gravity (i.e. where the appurtenance is oriented on the top of a wound dressing over a wound). In some embodiments, the appurtenance includes a micropump positioned to move fluids through a projection and into the appurtenance in a position adjacent to a sensor within a sensor unit. In some embodiments, the appurtenance includes a desiccant material. In some embodiments, the appurtenance includes a desiccant material positioned to draw fluid from a wound dressing into an interior of the appurtenance and to a sensor of a sensor unit. For example, a desiccant material can be positioned, in some embodiments, within a conduit or channel within an appurtenance. For example, a desiccant material can be positioned, in some embodiments, within a dedicated chamber attached to a sensor unit. In some embodiments, the appurtenance includes a sealed chamber that is under vacuum and connected to a projection or aperture. When the seal is broken, it sucks up the fluid into the tube in response to the low (or negative) air pressure in the tube.

A "transmission unit," as used herein, can be one or more of a variety of units that are configured to send and/or receive signals, such as signals carried as electromagnetic waves. In embodiments where the appurtenance includes a substrate, the transmission unit can be attached to a surface of the substrate, the transmission unit including circuitry and at least one antenna operably attached to the circuitry, the transmission unit configured to transmit a signal. In embodiments where the appurtenance includes an enclosure, the transmission unit can be attached to a surface of the enclosure, the transmission unit including circuitry and at least one antenna operably attached to the circuitry, the transmission unit configured to transmit a signal. A transmission unit generally includes at least one antenna and associated circuitry. A transmission unit can include a transmitter and a receiver. A transmission unit can include volatile or non-volatile memory. A transmission unit can include a processor. A transmission unit can be operably connected to an energy source, such as a battery. In some embodiments of an appurtenance, it is desirable to include a self-compensating antenna, such as described in U.S. Pat. No. 7,055,754 to Forester, titled "Self-Compensating Antennas for Substrates having Differing Dielectric Constant Values," which is incorporated herein by reference. A transmission unit can be operably connected to a processor. A transmission unit can be operably connected to a sensor. A transmission unit can be a passive device. A transmission unit can be an active device. A transmission unit can be a passive to active device. A transmission unit can be configured to transmit a signal in response to an interrogation signal. A transmission unit can include an energy harvesting unit, such as a unit configured to obtain energy from electromagnetic waves. A transmission unit can include a transponder utilizing electromagnetic waves, for example as described in "Fundamental Operating Principles," in Chapter 3 of the *RFID Handbook: Fundamentals and Applications in Contactless Smart Cards and Identification*, Klaus Finkenzeller, John Wiley & Sons, (2003), which is incorporated herein by reference. A transmission unit can include an oscillator and encoder configured to generate a programmable pulse position-modulated signal in the radio frequency range. See, for example, U.S. Pat. No. 4,384,288 to Walton, titled "Portable Radio Frequency Emitting Identifier," which is incorporated herein by reference. A transmission unit can include a radio frequency identification device (RFID). A transmission unit can be configured to be a transmitter of signals in the UHF range. A transmission unit including an RFID device can be configured to transmit signals in the UHF standard range utilized in a global region, as illustrated in the "Worldwide RFID UHF Map" by Intelleflex Corporation (©2009), which is incorporated herein by reference. A transmission unit can include a radio frequency identification device (RFID), which can be a passive RFID device, a semi-passive RFID device, or an active RFID device, depending on the embodiment. See, for example, Chawla and Ha, "An Overview of Passive RFID," *IEEE Applications and Practice,* 11-17 (September 2007), which is incorporated herein by reference. A transmission unit can include a battery-assisted passive RFID device, such as sold by Alien Technology®, Morgan Hill, Calif., such as described in the brochure from Alien Technology® titled "Battery Assisted Passive Tags" and incorporated herein by reference. A transmission unit can include an optical transmission unit. A transmission unit can be configured to transmit at approximately 13.56 megahertz (MHz), or within the ISO 14443 standard parameters. See Patauner et al., "High Speed RFID/NFC at the Frequency of 13.56 MHz," presented at the *First International EURASIP Workshop on RFID Technology*, pages 1-4, 24-25 Sep. 2007, Vienna Austria, which is incorporated herein by reference. A transmission unit can include at least two antennas. A transmission unit can include a self-compensating antenna system. An antenna can include dielectric material configured to electrically interact with one or more antennas. See, for example, U.S. Pat. No. 7,055,754 to Forster, titled "Self-Compensating Antennas for Substrates Having Differing Dielectric Constant Values," which is incorporated herein by reference. A transmission unit can include a hybrid backscatter system configured to function in an RFID, IEEE 802.11x standard and Bluetooth system. See, for example, U.S. Pat. No. 7,215,976 to Brideglall, titled "RFID Device, System and Method of Operation Including a Hybrid backscatter-based RFID Protocol Compatible with RFID, Bluetooth and/or IEEE 802.11x Infrastructure," which is incorporated herein by reference. A transmission unit can be configured to transmit at approximately 131 kilohertz (KHz), for example as part of a RuBee™ (IEEE standard 1902.1) system (sold, for example, by Visible Assets™, Inc.). See for example: the description of RuBee™ systems from the Visible Assets™ webpage; Stevens et al., "RuBee (IEEE 1902.1)—The Physics Behind, Real-Time, High Security Wireless Asset Visibility Networks in Harsh Environments," a white paper from Visible Assets™; and in US Patent Application No. 2007/0171076 to Stevens and Waterhouse, titled "Low-frequency Radio Tag Encapsulating System," each of which are incorporated herein by reference. A transmission unit can include a near field communication (NFC) device. A transmission unit can include a Wireless Identification and Sensing Platform (WISP) device, manufactured by Intel Corporation, such as described in the "WISP: Wireless Identification and Sensing Platform" webpage (downloaded on Oct. 28, 2011) incorporated herein by reference. A transmission unit can be operably coupled to a sensor, such as a sensor that detects changes in capacitance (see, e.g. Sample et al., "A Capacitive Touch Interface for Passive RFID Tags," 2009 *IEEE International Conference on RFID,* 103-109 (2009), which is incorporated herein by reference). A transmission unit can be operably coupled to a sensor, such as described in: Ruhanen et al., "Sensor-enabled RFID Tag and Handbook," from *Building Radio Frequency Identification for the Global Environment* (2008); Sample et al., "Design of an RFID-Based Battery-Free Programmable Sensing Platform," *IEEE Transactions on Instrumentation and Measurement*, vol. 57, no. 11, 2608-2615 (2008); Yeager et al., "Wirelessly-Charged UHF Tags for Sensor Data Collection," 2008 IEEE International Conference on RFID, Apr. 16-17, 2008, pages 320-327; U.S. Pat. Nos. 5,904,671 and 6,348,640 to Navot and Botton, each titled "Tampon Wetness Detection System;" U.S. Pat. No. 7,446,660 to Posamentier titled "Passive Environmental RFID Transceiver;" and U.S. Pat. No. 5,704,352 to Tremblay and Buckles, titled "Implantable Passive Bio-Sensor," which are each incorporated herein by reference. A transmission unit can be operably coupled to a data storage unit, for example as described in U.S. Pat. No. 7,825,776 to Smith and Haehnel, titled "Device Configuration with RFID," and US Patent Application No. 2009/0243813 to Smith at al., titled "Wireless Programming of Non-Volatile Memory with Near-Field UHF Coupling," which are each incorporated herein by reference.

In some embodiments, the transmission unit can include an acoustic transmitter. For example, a transmission unit can include a piezoelectric speaker. A variety of suitable piezoelectric speakers are available, including from Murata Manufacturing Co., Ltd., with North American corporate headquarters in Smyrna, Ga. (see, e.g. the Murata catalog titled "Piezoelectric Sounds Components" labeled P37E and dated Jan. 28, 2010, which is incorporated herein by reference). Some embodiments can include acoustic transmission units such as those manufactured by Advanced Telemetry Systems (headquartered in Isanti, Minn.) for the Pacific Northwest National Laboratory (see, e.g. JSATS Acoustic Transmitter information sheet from the Pacific Northwest National Laboratory, updated March 2010, which is incorporated herein by reference). In some embodiments, an appurtenance can include a piezoelectric speaker configured as part of an acoustic transmitter and also to act as a signaling device (e.g. to generate a beeping noise in response to a signal from the processor).

In some embodiments, the transmission unit can include an ultrasonic transmitter. In some embodiments, the transmission unit can include an ultrasonic transducer. Multiple examples of ultrasonic transmitters and transducers are commercially available, often marketed under the term "ultrasonic sensors" as it is used in the industry (see, e.g. the Murata catalog titled "Ultrasonic Sensor" labeled 515E and dated Oct. 31, 2008, which is incorporated herein by reference). The transmission unit can be configured as part of an ultrasonic ranging system. See: Wang, "A Design Method of Ultrasonic Ranging System with High Accuracy," *Journal of Computational Information Systems*, 7:7 pages 2444-2451 (2011), which is incorporated herein by reference. The transmission unit can be configured to communicate with an ultrasonic communication system. See: Chen and Wu, "Ultrasonic System with Infrared Communication Technology," *Journal of Computers*, vol. 6, no. 11, pages 2468-2475 (2011), which is incorporated herein by reference.

In some embodiments, the transmission unit can include an optical transmitter. For example, an optical transmission unit can include one or more white light emitting diodes (LEDs). For example, an optical transmission unit can include an infrared laser. In some embodiments, optical transmission units can be desirable to minimize interference from nearby electrical equipment, such as medical equipment. See: Kavehrad, "Sustainable Energy-Efficient Wireless Applications Using Light," *IEEE Communications Magazine*, vol. 48, no. 12, pages 66-73, (2010); and Fadlullah and Kavehrad, "Indoor High-Bandwidth Optical Wireless Links for Sensor Networks" *Journal of Lightwave Technology*, vol. 28, no. 21, pages 3086-3094 (2010), which are incorporated herein by reference.

Figure 3:
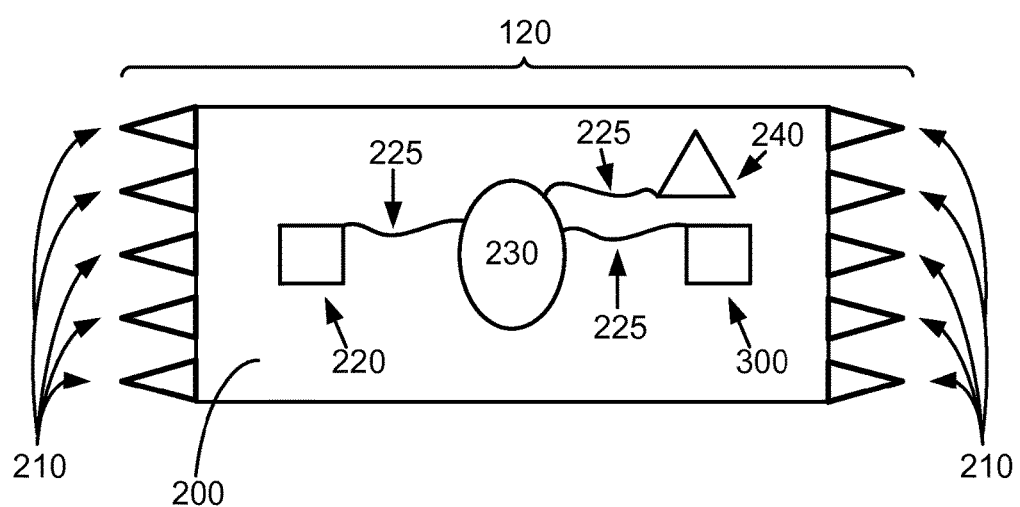
FIG. 3 is a schematic of an appurtenance to a wound dressing.

FIG. 3 illustrates aspects of an embodiment of an appurtenance to a wound dressing. The appurtenance 120 shown in FIG. 3 includes a substantially planar structure with a first set of a plurality of projections 210 attached to a first end of a substrate 200 (e.g. the left side as shown in FIG. 3) and a second set of a plurality of projections 210 attached to a second end of the substrate 200 (e.g. the right side as shown in FIG. 3). In the embodiment illustrated, each set of projections includes five projections.

Some embodiments include one or more sensor units positioned on opposing ends of a substrate. The embodiment of an appurtenance 120 to a wound dressing shown in FIG. 3 includes a first sensor unit 220 affixed to the substrate 200. In the embodiment shown, the first sensor unit 220 is affixed to the substrate 200 at a position adjacent to the first end of the substrate 200. The appurtenance 120 includes a transmission unit 230 affixed to an approximate center point on the planar surface of the substrate 200. The first sensor unit 220 is operably attached to the transmission unit 230 with a wire connector 225. The appurtenance 120 includes an electronic identifier 240 affixed to the substrate 200. The electronic identifier 240 is operably attached to the transmission unit 230 with a wire connector 225. The embodiment of an appurtenance 120 illustrated in FIG. 3 also includes a second sensor unit 300 affixed to the surface of the substrate 200. In the embodiment shown, the second sensor unit 300 is affixed to the substrate 200 at a position adjacent to the second end of the substrate 200. The second sensor unit 300 is operably attached to the transmission unit 230 with a wire connector 225.

Some embodiments include sensor units positioned on a substrate over regions of a wound dressing that are of particular interest. For example, in some situations a region of a wound may be at an increased risk for infection due to contamination or other conditions. In some embodiments, a wound dressing includes one or more appurtenances including sensor units with temperature sensors and/or sensors configured to detect proteins indicative of infection (e.g. bacterial proteins) affixed to one or more locations on a wound dressing intended to be positioned adjacent to a region of a wound at increased risk of infection. For example, the regions of skin adjacent to a wound can be at risk for maceration due to fluids of the wound. In some embodiments, a wound dressing includes one or more appurtenances including sensor units with wetness sensors and/or resonance sensors positioned at one or more positions on a substrate that are intended to be positioned on a wound dressing over a region of skin adjacent to a wound. Some embodiments include sensor units positioned on a substrate affixed to a wound dressing over regions of a wound that are of particular interest in monitoring through the wound dressing.

In some embodiments, all or a subset of the plurality of projections include substantially hollow structures including a proximal end affixed to an edge of the substrate, and a distal end including an aperture. In some embodiments, an aperture of a substantially hollow projection is positioned adjacent to a sensor unit. Some embodiments include at least one substantially hollow projection affixed to the substrate, the projection including a distal end with an aperture and a proximal end with an aperture, the proximal end positioned adjacent to the sensor unit. In some embodiments, some of the plurality of projections of the appurtenance include a channel internal to at least one of the plurality of projections, the channel attached to a first aperture at a distal end of the projection, the channel attached to a second aperture positioned adjacent to the substrate, and an enclosed tubular structure attached to the substrate, the enclosed tubular structure affixed to the second aperture at a first end, the tubular structure affixed to a sensor unit at a second end. Some embodiments further include: one or more walls forming a gas-sealed chamber attached to the enclosed tubular structure, the gas-sealed chamber including an internal gas pressure below atmospheric pressure; and a breakable seal between the gas-sealed chamber and the enclosed tubular structure. Some embodiments include projections with an internal channel as well as projections without an internal channel. In some embodiments, all of the projections include internal channels.

Figure 4:
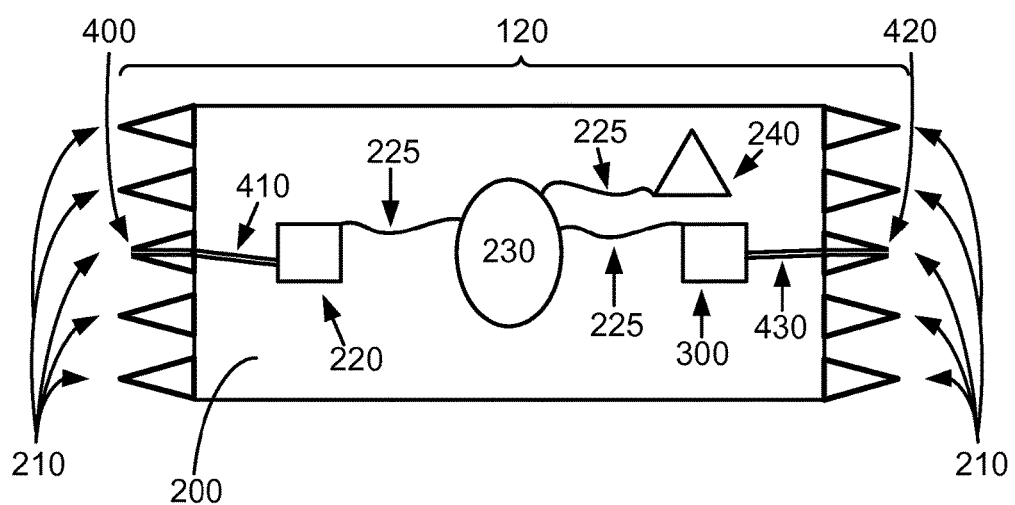
FIG. 4 is a schematic of an appurtenance to a wound dressing.

For example, FIG. 4 illustrates a projection at the center left of the substrate 200 including an interior hollow channel 400 positioned along the main axis of the projection 210. The interior hollow channel 400 has a distal end terminating at an aperture in the projection at a location substantially corresponding to the tip of the conical projection. The interior hollow channel 400 has a proximal end affixed to the edge of the substrate 200. The proximal end of the hollow channel 400 of the projection 210 is affixed to an enclosed tubular structure 410 attached to the substrate 200. The enclosed tubular structure 410 has a first end affixed to the hollow channel 400 of the projection 210, and a second end attached to a first sensor unit 220. Similarly, the appurtenance 120 illustrated in FIG. 4 includes a projection at the center right of the substrate 200 including an interior hollow channel 420 positioned along the main axis of the projection 210. The interior hollow channel 420 has a distal end terminating at an aperture in the projection at a location substantially corresponding to the tip of the conical projection. The interior hollow channel 420 has a proximal end affixed to the edge of the substrate 200. The proximal end of the hollow channel 420 of the projection 210 is affixed to an enclosed tubular structure 430 attached to the substrate 200. The enclosed tubular structure 430 has a first end affixed to the hollow channel 420 of the projection 210, and a second end attached to a second sensor unit 300. An electronic identifier 240 is also attached to the substrate 200. A wire connector 225 operably connects the electronic identifier 240 to the transmission unit 230.

In some embodiments, an appurtenance to a wound dressing includes: a channel internal to at least one of the plurality of projections, the channel attached to a first aperture at a distal end of the projection, the channel attached to a second aperture positioned adjacent to the substrate; and an enclosed tubular structure attached to the substrate, the enclosed tubular structure affixed to the second aperture at a first end, the tubular structure affixed to a sensor unit at a second end. Some embodiments further include: one or more walls forming a gas-sealed chamber attached to the enclosed tubular structure, the gas-sealed chamber including an internal gas pressure below atmospheric pressure; and a breakable seal between the gas-sealed chamber and the enclosed tubular structure.

Some embodiments include desiccant material within one or more of the channels internal to at least one of the plurality of projections. Some embodiments include desiccant material within an enclosed tubular structure attached to the substrate. For example, a desiccant material can be selected and positioned to encourage fluid flow along the channel of a projection 210 or along an enclosed tubular structure attached to the substrate 200. A desiccant material can be selected as suitable for a particular embodiment based on its cost, mass, or efficiency. For example, in some embodiments a desiccant material includes one or more of: activated charcoal, calcium sulfate, calcium chloride, or a zeolite. Some embodiments include sorbent material within one or more of the channels internal to at least one of the plurality of projections. Some embodiments include sorbent material within an enclosed tubular structure attached to the substrate. For example, a sorbent material can be selected and positioned to encourage fluid flow along the channel of a projection or along an enclosed tubular structure attached to the substrate. A sorbent material can be selected as suitable for a particular embodiment based on its cost, mass, or efficiency of sorption of wound fluid. For example, in some embodiments a sorbent includes one or more of: a cellulose fiber, a polypropylene fiber, or a hydrophilic gel material.

Figure 5A:
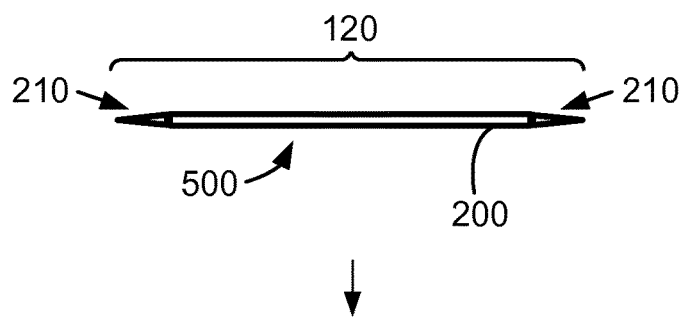
FIG. 5A is a schematic of an appurtenance to a wound dressing.

FIG. 5A illustrates an appurtenance 120 including a substrate 200 that is a substantially planar structure. The view of FIG. 5A shows the appurtenance in a side view (i.e. substantially at right angles to the view of FIGS. 3 and 4). The substrate includes a surface 500 of a size and shape to reversibly mate with a surface of a wound dressing. Some embodiments include an appurtenance including at least one substantially planar surface of a size and shape to reversibly mate with a substantially planar surface of a wound dressing. Some embodiments include an appurtenance including at least one surface of a size and shape to reversibly mate with a surface of a wound dressing, wherein the surface of the wound dressing is a substantially non-planar surface. For example, the surface of a wound dressing may include one or more regularly spaced ridges, grooves, bumps or indentations and the surface of an appurtenance can include corresponding ridges, grooves, bumps or indentations as required to reversibly mate with the wound dressing surface. Some embodiments include a plurality of projections extending outward along a largest linear dimension of the substrate. For example FIG. 5A illustrates a substrate 200 at a side view along the longest axis (e.g. right to left in the illustration) and projections 210 with their longest axes substantially positioned along the same plane as the longest axis of the substrate 200.

Figure 5B:
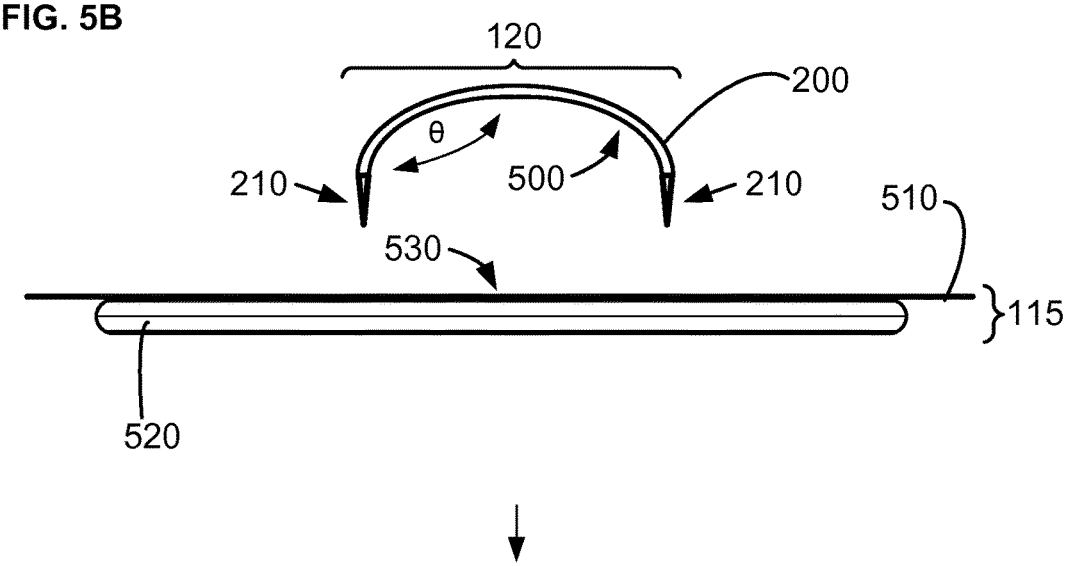
FIG. 5B is a schematic of an appurtenance and a wound dressing.
Figure 5C:
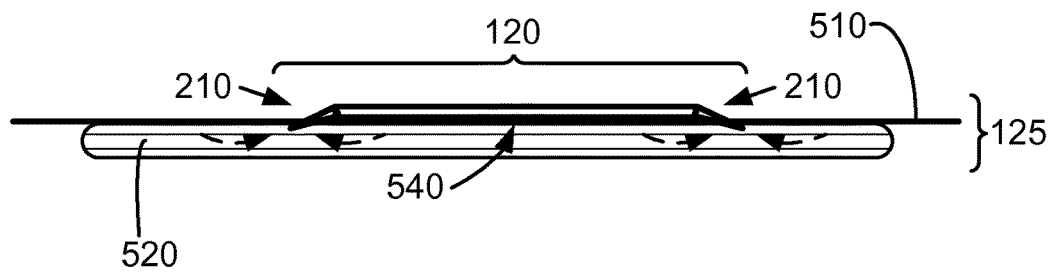
FIG. 5C is a schematic of an appurtenance affixed to a wound dressing.

FIG. 5B depicts an appurtenance 120 including a substrate 200 and a wound dressing 115. The view of FIG. 5B is a side view, similar to the view of FIG. 5A. The wound dressing 115 illustrated includes dressing layer 520 and an outer layer 510. Not all wound dressings 115 should be expected to include multiple layers, and it is to be expected that some wound dressings 115 substantially include only a wound dressing material and not additional layers, structures or coverings. However, as illustrated in FIGS. 5B and 5C, in some embodiments wound dressings 115 include a plurality of layers. For example, a wound dressing 115 can include one or more outer layers configured to protect and isolate the wound dressing layer(s) from microbes, external dirt and debris, dryness, wetness or other external factors. An outer layer can be fabricated from materials such as firm plastics or mesh materials. An outer layer can include a surface larger than the surface of the wound dressing layer, and can include adhesives on that surface configured to adhere the entire wound dressing to a body surface. A wound dressing can include one or more layers of wound dressing materials, such as gauze, films, foams, or sponges. A wound dressing can include one or more layers of hydrogels, colloid gels, and medicinal agents impregnated within one or more layers of the wound dressing or on a surface of the wound dressing configured to face a wound.

The appurtenance 120 illustrated in FIG. 5B is a flexible structure along a long axis of the substrate 200. Although the illustrated embodiment is expected to generally be a flat or substantially planar structure in the absence of external force, in the view of FIG. 5B the appurtenance 120 has been flexed or bent in response to an external force (e.g. pressure from a person's fingers) so that each side of the appurtenance is bent by angle θ relative to a midline of the appurtenance. In some embodiments, an angle θ can be a range of degrees. For example, in some embodiments, an angle θ can be between approximately 20 and approximately 50 degrees. For example, in some embodiments, an angle θ can be approximately 20 degrees, approximately 25 degrees, approximately 30 degrees, approximately 35 degrees, approximately 40 degrees, approximately 45 degrees, or approximately 50 degrees. The appurtenance 120 is bent with surface 500 facing the interior angle to reversibly mate with a surface 530 of the wound dressing 115. In some embodiments, during application of an appurtenance to a wound dressing, a flexible appurtenance is bent by a user, after which time the sets of projections affixed to opposing ends of the substrate are placed adjacent to the exterior surface of the wound dressing. When the user releases the appurtenance, it then flexes back to a substantially planar structure, with the sets of projections extending into the interior of the wound dressing (see, e.g. FIG. 5C). In some embodiments, the substrate is flexible and each of the plurality of projections include a proximal end and a distal end, with the projections tapering in size from the proximal end to the distal end. The distal end of the projections are positioned at the surface of the wound dressing while the appurtenance is bent, such that when the appurtenance is released it flexes back to a planar shape and the projections are forced into the surface of the wound dressing.

FIG. 5C illustrates an appurtenance 120 similar to those shown in FIGS. 5A and 5B, with the appurtenance affixed to a wound dressing to create an appurtenance affixed to a wound dressing combination unit, 125. Surfaces of the appurtenance 120 and the outer layer 510 are mated at a junction 540 interior to the appurtenance affixed to a wound dressing combination unit, 125. The sets of projections 210 affixed to the ends of the appurtenance 120 include distal ends that are embedded in the wound dressing. The ends of the projections 210 traverse the outer layer 510 of the wound dressing into the dressing layer 520. During use, fluid in the dressing can flow into the ends of the projections 210 that include an internal channel, as shown by the dotted lines in FIG. 5C.

Figure 6A:
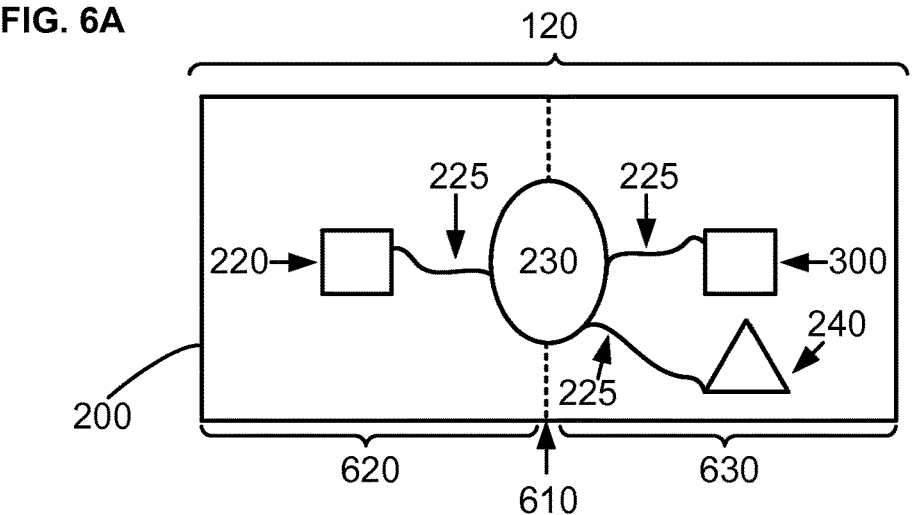
FIG. 6A is a schematic of an appurtenance to a wound dressing.

FIG. 6A shows aspects of an embodiment of an appurtenance 120 to a wound dressing. The appurtenance 120 includes a substrate 200 that is a substantially planar structure shown in a "top-down" viewpoint. The substrate is bisected along its short diameter by a divider 610, positioned to separate the substrate 200 into a first section 620 and a second section 630. A transmission unit 230 is positioned within the line of the divider 610. In some embodiments, a divider is positioned within the substrate structure in a location that separates the interior of the substrate into a series of regularly-sized compartments. In some embodiments, a divider is positioned within the substrate structure in a location that separates the interior of the substrate into a series of compartments of approximately similar sizes. In some embodiments, a divider is positioned within the substrate structure in a location that separates the interior of the substrate into a series of compartments of differing sizes. In some embodiments, there is at least one flexible divider internal to the substrate, the flexible divider positioned between a first sensor unit and a second sensor unit. A flexible divider, for example, can be fabricated with sufficient strength to maintain its position and integrity even when the entire substrate structure is bent or flexed (e.g. see FIG. 5B). A first sensor unit 220 is affixed to the substrate in approximately the center of the first section 620. A second sensor unit 300 is affixed to the substrate in approximately the center of the second section 620. Some embodiments include at least two sensor units, the sensor units positioned on opposing ends of the substrate. Some embodiments further include a divider positioned between each of the sensor units. Wire connectors 225 connect each of the sensor units 220, 300 to the transmission unit 230. An electronic identifier 240 is also attached to the substrate 200 in the second section 620. A wire connector 225 operably connects the electronic identifier 240 to the transmission unit 230.

A "divider" to an appurtenance, as discussed herein, is an internal structure positioned within the substrate. For example, in embodiments including a substrate with at least two walls, a divider can be positioned between the walls, with a first edge of the divider affixed to a first wall and a second edge of the divider attached to a second wall of the substrate. In embodiments including a substrate with at least two walls and sorbent or desiccant material positioned between the walls, a divider is positioned to separate a first section of sorbent or desiccant material and a second section of sorbent or desiccant material. In embodiments wherein a substrate is a foam structure, a divider can include a structure within the foam that partitions one section of the foam from an adjacent section. A divider can be fabricated, for example, from a thin plastic material, such as a thin plastic sheet. A divider can be fabricated, for example, from a thin polyester material, such as a thin PET sheet. A divider can be fabricated, for example, from a thermally reflective material, such as a metalized boPET sheet. In some embodiments, a divider is fabricated from the same material as the associated substrate. A divider is positioned to internally separate sections of the substrate, for example to minimize wound fluid wicking through the interior of the substrate. A divider material, depending on the embodiment, is selected to be non-porous to wound fluid within the substrate structure. A divider material, depending on the embodiment, is selected to be thermally reflective.

Figure 6B:
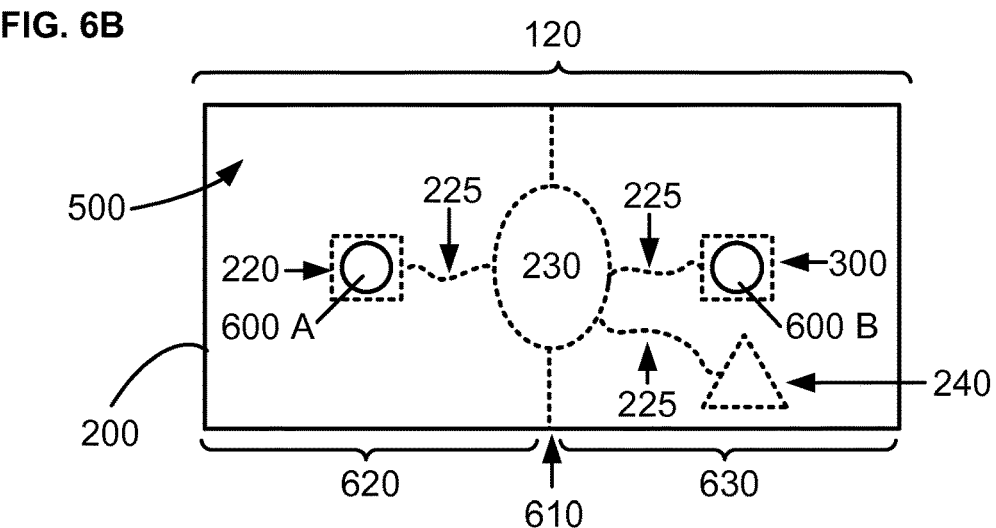
FIG. 6B is a schematic of an appurtenance to a wound dressing.
Figure 6C:
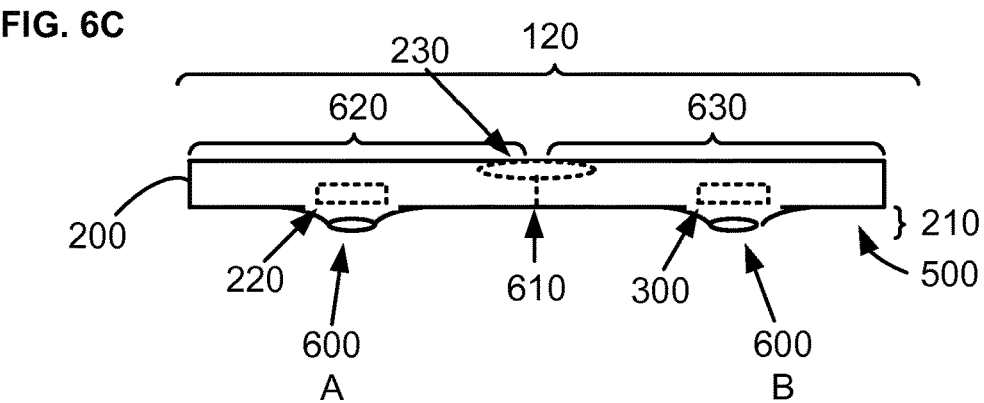
FIG. 6C is a schematic of an appurtenance to a wound dressing.

FIG. 6B illustrates aspects of an appurtenance 120. The view shown in FIG. 6B is a substantially "bottom up" view of the appurtenance, so that the surface 400 configured to reversibly mate with the surface of a wound dressing is visible. For purposes of illustration, internal structures are shown with dotted lines. The substrate 200 has two projections (see, e.g. as shown in FIG. 6C) at the surface 500 configured to reversibly mate with the surface of a wound dressing. Each of the two projections is positioned substantially in the center of a section 620, 630 of the substrate 200, with an internal divider 610 separating the substrate 200 into two approximately equally-sized sections. The substrate 200 includes two projections, each of which terminate with an aperture 600 A, 600 B. A first projection with an aperture 600 A is positioned approximately in the center of the first section 620. A first sensor unit 220 is positioned adjacent to the first projection and its aperture 600 A. The first sensor unit 220 is connected to a centrally-positioned transmission unit 230 with a wire connector 225. A second projection with an aperture 600 B is positioned approximately in the center of the second section 630. A second sensor unit 300 is positioned adjacent to the second projection and its aperture 600 B. The second sensor unit 300 is connected to the centrally-positioned transmission unit 230 with a wire connector 225. An electronic identifier 240 is affixed to the substrate 200 at a position within the second section 630. The electronic identifier 240 is operably attached to the transmission unit 230 with a wire connector 225.

FIG. 6C illustrates aspects of an embodiment of an appurtenance 120. The appurtenance 120 shown in FIG. 6C is a substantially planar appurtenance, shown at an edge view with some interior structures depicted with dotted lines for purposes of illustration. The embodiment includes a substrate 200 with walls surrounding an interior space. A divider 610 is positioned within the interior space, the divider 610 including a first end attached to a first wall and a second end attached to a second wall of the substrate 200. The divider 610 separates the interior of the substrate 200 into a first section 620 and a second section 630. A transmission unit 230 is centrally positioned within the interior space. The substrate includes projections 210 positioned on the surface 500 configured to reversibly mate with a surface of a wound dressing. Each of the projections 210 is positioned approximately at the center of a section 620, 630 of the substrate 200. Each of the projections 210 ends with a distal aperture 600 A, 600 B. A first sensor unit 220 is positioned within the first section 620 of the substrate 200, the first sensor unit 220 positioned adjacent to the aperture 600A of the projection 210. A second sensor unit 300 is positioned within the second section 620 of the substrate 200, the second sensor unit 300 positioned adjacent to the aperture 600B of the projection 210. The first sensor unit 220 is separated from the second sensor unit 300 by the divider 610. A connector, such as a wire connector, operably connects each of the sensor units to the transmission unit.

Some embodiments include an appurtenance to a wound dressing, including: an enclosure including at least one external surface of a size and shape to reversibly mate with a surface of a wound dressing; a sensor unit affixed to the enclosure; an electronic identifier affixed to the enclosure; and a transmitter unit operably attached to the sensor unit and to the electronic identifier.

Figure 7:
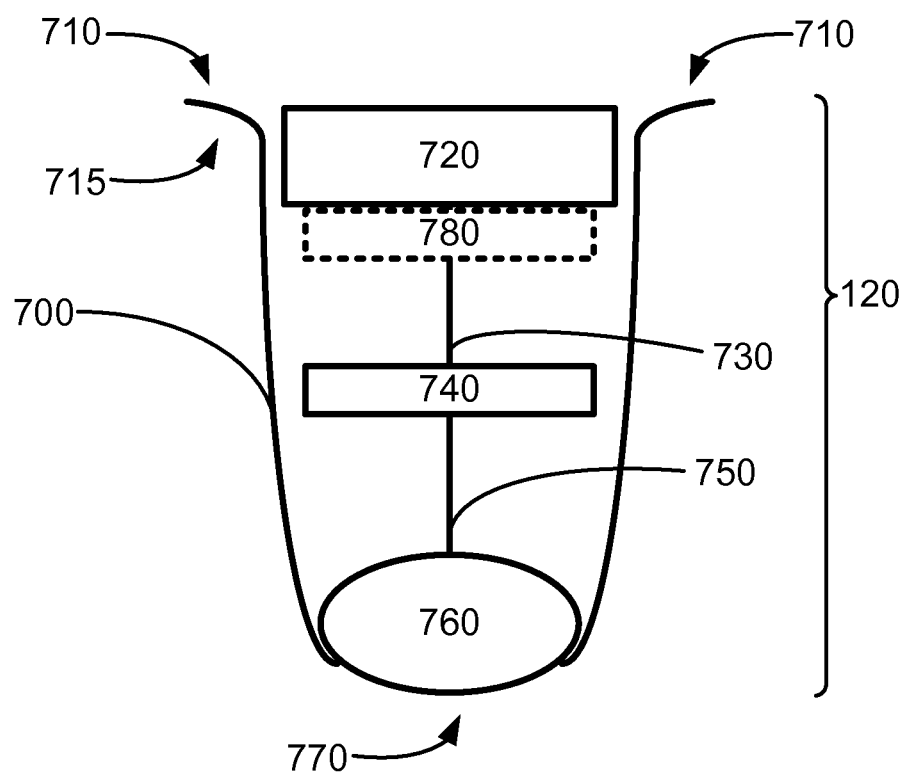
FIG. 7 is a schematic of an appurtenance to a wound dressing.

For example, FIG. 7 illustrates an appurtenance 120 including an enclosure 700. The view shown in FIG. 7 includes a substantially cross-section view of an appurtenance 120 to illustrate internal features of the appurtenance. The enclosure 700 substantially defines the exterior surface of the appurtenance 120. The enclosure 700 includes a flange 710 positioned at an edge of the enclosure. In some embodiments, a flange 710 includes a surface 715 positioned to contact a surface of a wound dressing when the appurtenance 120 is in use with a wound dressing. An aperture 770 is positioned within the enclosure 700. Some embodiments include a single aperture in the enclosure. For example, some embodiments include a single aperture at an end region of the appurtenance. Some embodiments include a plurality of apertures in the enclosure. For example, some embodiments include a plurality of apertures positioned at regular intervals around the surface of the enclosure.

Some embodiments are configured for a user to press into an aperture in a wound dressing. Some embodiments are configured for a user to press into a slit or channel in a wound dressing. Some embodiments include an appurtenance wherein the enclosure is a substantially cylindrical structure. Some embodiments include an appurtenance wherein the enclosure is a substantially conical structure. Some embodiments include an appurtenance wherein the enclosure is a substantially elliptical structure. Some embodiments include an appurtenance wherein the at least one external surface of a size and shape to reversibly mate with a surface of a wound dressing is substantially smooth. Some embodiments include an appurtenance wherein the enclosure includes at least one external surface of a size and shape to reversibly mate with the surface of an aperture within the wound dressing. Some embodiments include an appurtenance wherein the enclosure includes at least one external surface of a size and shape to reversibly mate with the surface of the wound dressing, wherein the surface is a curved surface. Some embodiments include an appurtenance wherein the enclosure includes at least one external surface of a size and shape to reversibly mate with the surface of the wound dressing, wherein the surface is a flexed surface. Some embodiments include an appurtenance wherein the enclosure includes at least one external surface of a size and shape to reversibly mate with the surface of the wound dressing, wherein the surface is a substantially non-planar surface. Some embodiments include an appurtenance wherein the enclosure includes at least one external surface including at least one chemical adherent positioned to affix the wound dressing to the enclosure. Some embodiments include an appurtenance wherein the enclosure is of a height and width to fit substantially through an aperture in the wound dressing, the enclosure including at least one surface configured to reversibly mate with a surface of the aperture within an interior region of the wound dressing. Some embodiments include an appurtenance wherein the enclosure includes one or more protuberances affixed to the at least one external surface. Some embodiments include an appurtenance wherein the enclosure includes one or more indentations in the at least one external surface. Some embodiments include an appurtenance wherein the enclosure includes one or more apertures in the at least one external surface. Some embodiments include an appurtenance wherein the enclosure includes a desiccant material within the enclosure.

An enclosure for an appurtenance can be fabricated from a variety of materials, depending on the embodiment. For example, in some embodiments an enclosure of an appurtenance is fabricated from a plastic material. For example, in some embodiments an enclosure of an appurtenance is fabricated from a metal. For example, in some embodiments an enclosure of an appurtenance is fabricated from a paper-based material of sufficient toughness for the required durability of an embodiment. Some embodiments include a fluid transport film affixed to the enclosure. For example, some embodiments include a fluid transport film affixed to an interior surface of the enclosure. For example, some embodiments include a fluid transport film affixed to an interior surface of the enclosure adjacent to one or more apertures, with the fluid transport film positioned to direct fluid into the interior of the enclosure through at least one aperture. Some embodiments include a fluid control film affixed to the enclosure. For example, some embodiments include a fluid control film affixed to an interior surface of the enclosure. For example, some embodiments include a fluid control film affixed to an interior surface of the enclosure through the interior surface, with apertures in the fluid control film corresponding to apertures in the enclosure of the appurtenance. For example, some embodiments include a fluid control film affixed to an interior surface of the enclosure adjacent to one or more sensor units, with the fluid control film positioned to isolate a surface of the one or more sensor units from a flow of wound fluid internal to the appurtenance.

FIG. 7 illustrates an embodiment with a sensor unit 760 positioned adjacent to the single aperture 770 in the enclosure. Some embodiments include a plurality of apertures in the enclosure. The sensor unit 760 is positioned and angled to detect properties of the wound dressing and/or wound fluid in the wound dressing. For example, the sensor unit can, in some embodiments, be positioned and/or angled to detect properties including at least one of: temperature, fluid pressure, moisture, or the presence of one or more specific proteins (e.g. MMPs). In some embodiments, a sensor unit includes a chemical sensor. In some embodiments, a sensor unit includes a resonance sensor. For example, a resonance sensor can be positioned to detect a change in the resonance of the wound dressing. In some embodiments, a sensor unit includes a pH sensor. In some embodiments, a sensor unit includes a pH sensor including a detector of a specific biological agent. In some embodiments, a sensor unit includes at least one antibody. In some embodiments, a sensor unit includes at least one aptimer. In some embodiments, a sensor unit includes a temperature sensor. In some embodiments, a sensor unit includes a plurality of sensors within each sensor unit. In some embodiments, a sensor unit includes at least two sensors of different types. In some embodiments, a sensor unit includes: a sensor; circuitry for accepting data from the sensor; and circuitry for sending the accepted data to the processor. In some embodiments, a sensor unit includes: a sensor; circuitry for accepting data from the sensor; circuitry for processing the accepted data; and circuitry for sending the processed data to the transmission unit. In some embodiments, a sensor unit includes: reversible fasteners of a size and shape for attachment to the substrate.

In some embodiments, a resonance sensor includes: a passive RFID unit including a cavity resonator. Some embodiments include wherein the resonance sensor includes a passive RFID unit including a cavity resonator of a size and shape to have dampened resonance within the cavity resonator when the wound dressing is substantially saturated with fluid, and further including a passive RFID including a unique identifier and a self-compensating antenna calibrated for use with the wound dressing. Since fluid from a wound, including blood and pus, is a dielectric material, a wound dressing full of fluid from a wound will have different dielectric properties when it is dry than it does when it is saturated with wound fluid. Some embodiments include at least a first RFID unit that includes a mechanism for compensating for resonance changes in connection with a dry wound dressing and also when the wound dressing is substantially saturated, and a second RFID unit with structure that will be functional in association with the dry wound dressing and dampened in connection when the wound dressing is substantially saturated with fluid from the wound. See, for example, U.S. Pat. No. 7,055,754 to Forster, titled "Self-Compensating Antennas for Substrates Having Differing Dielectric Constant Values," which is incorporated herein by reference.

Some embodiments include: an aperture in the enclosure; a channel including a first end affixed to the enclosure and a second end affixed to the sensor unit; one or more walls forming a gas-sealed chamber adjacent to the channel, the gas-sealed chamber with an internal gas pressure below atmospheric pressure; an aperture in the one or more walls of the gas-sealed chamber at a position adjacent to the channel; a breakable seal at the aperture in the one or more walls of the gas-sealed chamber; an aperture in the channel at a position corresponding to the aperture in the one or more walls of the gas-sealed chamber; and a seal between the aperture in the one or more walls of the gas-sealed chamber and the aperture in the channel. Some embodiments include at least one desiccant material. Some embodiments include at least one sorbent material.

FIG. 7 illustrates an embodiment including an electronic identifier 740. The electronic identifier 740 is positioned within the enclosure and is connected to the sensor unit 760 with a wire connector 750. The electronic identifier 740 is affixed to the enclosure. The embodiment shown in FIG. 7 includes a transmission unit 720. The transmission unit 720 is connected to the electronic identifier 740 with a wire connector. Some embodiments include a battery unit 780 operably connected to the electronic identifier 740. Some embodiments include a battery unit 780 operably connected to the transmission unit 720. For example, in some embodiments the transmission unit requires electrical power for full operation, which is supplied from an associated battery. Some embodiments include a processor. In some embodiments, a processor includes: circuitry configured to accept data from at least one of the one or more sensor units; circuitry configured to process the accepted data; and circuitry configured to send the processed data to the at least one transmission unit. In some embodiments, a processor includes: circuitry configured to accept data from an electronic identifier; circuitry configured to process the accepted data; and circuitry configured to send the processed data to the at least one transmission unit.

In some embodiments, an appurtenance including an enclosure includes at least two sensor units, the sensor units positioned on opposing ends of the enclosure. In some embodiments, an appurtenance including an enclosure includes at least two sensor units, the sensor units positioned on opposing ends of the enclosure and a divider positioned between each of the sensor units. In some embodiments, an electronic identifier includes an RFID unit. In some embodiments, an electronic identifier includes an electronic code. In some embodiments, an electronic identifier includes a passive device. In some embodiments, an electronic identifier includes an active device. In some embodiments, an electronic identifier includes a passive to active device.

Figure 8:
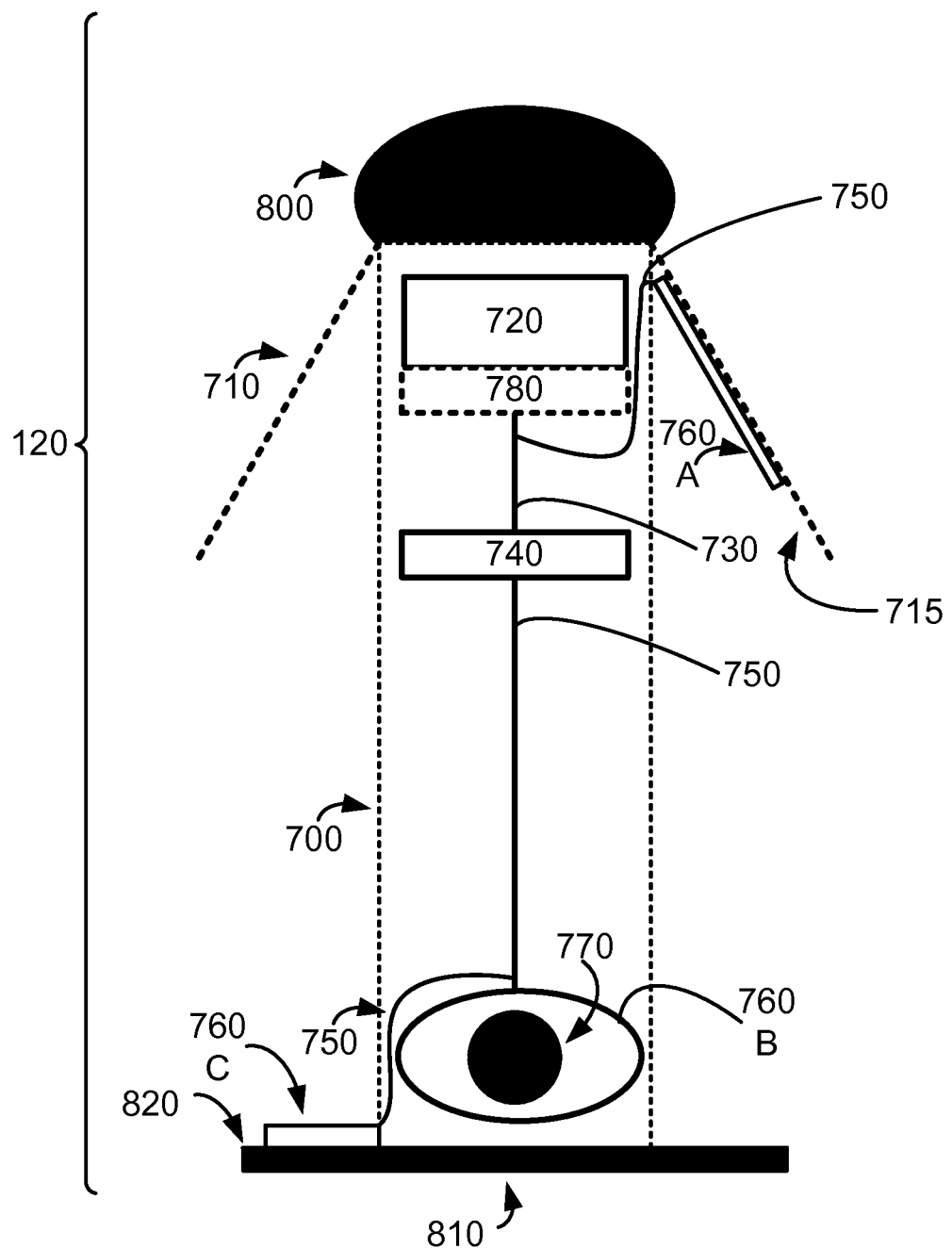
FIG. 8 is a schematic of an appurtenance to a wound dressing.

FIG. 8 illustrates aspects of an embodiment of an appurtenance 120. The appurtenance 120 is illustrated in an external side view. The appurtenance 120 includes an enclosure 700 that is a substantially cylindrical structure. In some embodiments, an enclosure is a substantially conical structure. In some embodiments, an enclosure is a substantially elliptical structure. The enclosure 700 includes an external surface of a size and shape to reversibly mate with a surface of a wound dressing. The external surface of a size and shape to reversibly mate with a surface of a wound dressing is substantially smooth. The enclosure 700 is of a height and width to fit substantially through an aperture in a wound dressing of a particular type (e.g. size and style). The enclosure 700 includes at least one surface configured to reversibly mate with a surface of the aperture within an interior region of the wound dressing. In some embodiments, an enclosure includes one or more apertures in the external surface. In the view shown in FIG. 8, the enclosure 700 includes one aperture 770.

The appurtenance 120 includes a flange 710 attached to a circumference of the external surface of the enclosure near a first end of the enclosure (e.g. the top in the view of FIG. 8). The flange 710 is a planar structure affixed to the exterior surface of the enclosure at a top edge of the enclosure structure. The view of FIG. 8 depicts the flange 710 structure as transparent for illustration purposes. In some embodiments, a flange is flexible. In some embodiments, a flange is fabricated from a flexible material, such as a flexible rubber or a flexible plastic material. In some embodiments, a flange is fabricated from a material with sufficient flexibility so that the surface 715 of the flange 710 can reversibly move between a position essentially adjacent to the exterior surface of the enclosure 700 to a position essentially at right angles to the exterior surface of the enclosure 700 without damage to the flange 710. Some embodiments include at least one sensor unit affixed to a surface of the flange adjacent to an expected position of the wound dressing (e.g. surface 715 in FIG. 8). Some embodiments include a positioning element 800 affixed to an end of the enclosure. For example, a positioning element can be of a size and shape to assist a user of the appurtenance to position the appurtenance relative to a wound dressing during use. For example, a positioning element can be of a size and shape for a human finger tips to grasp the appurtenance.

Some embodiments of an appurtenance include an end cap attached to the external surface of the enclosure at an end of the enclosure. For example, FIG. 8 illustrates an appurtenance 120 including an end cap 810 attached to the external surface of the enclosure 700 at a second end of the enclosure 700. Some embodiments include an end cap attached to a surface of the enclosure adjacent to an end distal to the attachment site of a flange. In the embodiment shown in FIG. 8, the end cap 810 is a substantially planar structure, affixed to the external surface of the enclosure 700 substantially perpendicularly to a long axis of the enclosure 700. The appurtenance 120 includes an end cap 810 affixed to a second end of the appurtenance 120, which is distal to the positioning element 800. In some embodiments, an end cap is substantially a disk structure. For example, the enclosure can be attached to the center region of an end cap that is a disk or disk-like structure. Depending on the embodiment, an end cap can be fabricated from the same material as the enclosure and fabricated as an integral structure with the enclosure. In some embodiments, an end cap is fabricated from a stiff material, such as a solid plastic or ceramic material. Some embodiments include a surface adjacent to an expected position of the wound dressing. For example, the embodiment of FIG. 8 includes a surface 820 adjacent to an expected position of the wound dressing. The surface 820 shown in FIG. 8 is a substantially planar surface of a size and shape to conform with a planar surface of a wound dressing. In some embodiments, a surface of an end cap adjacent to an expected position of a wound dressing includes one or more ridges, bumps, grooves or other structural features positioned to reversibly mate with a surface of a wound dressing. Some embodiments include at least one sensor unit affixed to a surface of the end cap adjacent to an expected position of the wound dressing.

The embodiment of an appurtenance 120 shown in FIG. 8 includes a first sensor unit 760 A affixed to a surface 715 of the flange 710 positioned to contact a surface of a wound dressing when the appurtenance 120 is in use with a wound dressing. For example, in some embodiments a first sensor unit affixed to the flange can include one or more of: a temperature sensor, or a pressure sensor. The first sensor unit 760 A is connected to a processor and a transmission unit 720 with wire connectors 750, 730. The appurtenance 120 includes a second sensor unit 760 B positioned within the enclosure at a location adjacent to the aperture 770. For example, some embodiments include a sensor unit positioned to detect characteristics of the wound fluid within a wound dressing. The second sensor unit 760 B is connected to an electronic identifier 740 and the transmission unit 720 with a wire connector 750. The embodiment illustrated in FIG. 8 includes a third sensor unit 760 C affixed to the end cap 810 on the surface adjacent to an expected position of the wound dressing. For example, in some embodiments a sensor unit affixed to the end cap can include one or more of: a pressure sensor, a sensor unit configured to detect components of wound fluid, and/or a temperature sensor. Some embodiments include a processor. Some embodiments include a battery 780 attached to the transmission unit 720 and/or a processor, for example with a wire connector.

Figure 9:
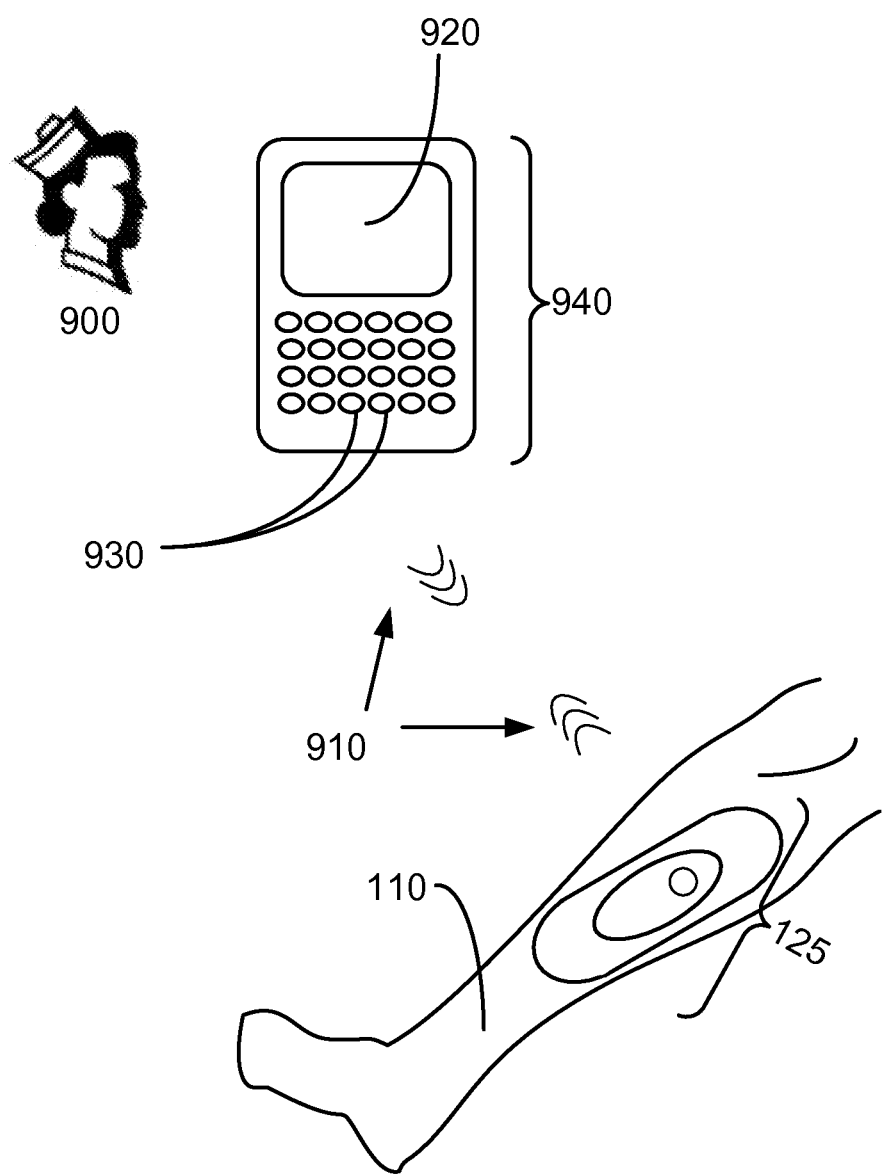
FIG. 9 is a schematic of an appurtenance to a wound dressing in communication with a local unit.

FIG. 9 illustrates aspects of a system including a wound dressing with an affixed appurtenance combination unit 125.

As shown in FIG. 9, a wound dressing with an affixed appurtenance combination unit 125 is placed over a wound on a body part 110 of a patient. For example, the body part 110 may have been subject to a surgery, and therefore to have an acute wound. For example, the body part 110 can include an ulcer, and therefore have a chronic wound. The wound dressing with an affixed appurtenance combination unit 125 receives signals 910 from a local unit 940 and transmits signals 910 to the local unit 940. For example, the wound dressing with an affixed appurtenance combination unit 125 can include a passive RFID configured to transmit signals 910 after receiving signals 910 from a proximal RFID reader device in the local unit 940. The appurtenance illustrated in FIG. 9 includes: a sensor unit, an electronic identifier, and a transmitter unit operably attached to the sensor unit and to the electronic identifier. In some embodiments, an appurtenance includes a substrate. In some embodiments, an appurtenance includes an enclosure. The local unit 940 includes: a receiver for the transmitter unit, a processor operably attached to the receiver, and a communication unit operably attached to the processor.

In some embodiments, a transmitter unit included in an appurtenance includes: a radio-frequency identification (RFID) transmitter. In some embodiments, a transmitter unit included in an appurtenance includes: a near field communication (NFC) device. In some embodiments, an appurtenance includes non-volatile memory. For example, an appurtenance can include a RFID transmitter and associated non-volatile memory. In some embodiments, an appurtenance includes a receiver. In some embodiments, an appurtenance includes at least one indicator. For example, in some embodiments an appurtenance can include a small LED light and circuitry to illuminate the light when a signal from a local unit is received by a receiver. For example, in some embodiments an appurtenance can include a small LED light and circuitry to illuminate the light when a signal from to local unit is sent by the transmission unit.

A local unit 940 can include a handheld device. For example, the local unit 940 can include a distinct handheld device. For example, the local unit 940 can be of a size, a shape and a configuration for portable handheld use. For example, the local unit 940 can be included as part of a larger handheld unit, for example a tablet, a laptop, a cell phone, a personal communication device, or similar types of devices. A local unit can be integrated with an institutional furnishing, such as a hospital bed, a medical stand, a bedside table or a surgical cart. A local unit can be of a size, a shape and a configuration for portable handheld use. A local unit can be configured to be attached to a mobile unit, such as the end of a hospital bed, a medical stand, a bedside table, a wheelchair, or similar device. For example, a local unit can be integrated with a medical cart, as described in U.S. Pat. No. 7,667,606 to Packert et al., titled "RF Enabled Surgical Cart and Use of Same in Operating Room Environment," which is incorporated herein by reference. A local unit can be configured as a wall- or ceiling-mounted unit. A local unit can be configured to plug into a wall socket, for example with the addition of utilizing the wall socket as a power source. A local unit can be configured to be part of a larger system, such as a facility-wide system in a medical facility. A local unit can be configured to be integrated into a furnishing. For example, a local unit can be integrated into a hospital bed, a bedside hospital monitor, a bedside table, a medical chair, a medical table, or similar furnishing. A local unit 940 can include a display unit 920. In some embodiments, there can be a secondary device configured to relay signals to the local unit, for example as described in U.S. Pat. No. 7,986,235 to Posamentier titled "RFID Receive-Only System," which is incorporated herein by reference. A local unit can include a communication unit configured to send signals to a central assembly. The communication unit of a local unit can include at least one of: a visual display, a sound generator, a vibrating unit, and one or more light displays. A local unit can include at least one user interface, such as a screen, monitor, touchscreen or voice recognition element. A local unit can include an auditory signal generator. A local unit 940 can include an input device 930, for example a keyboard. Although the local unit 940 illustrated in FIG. 9 includes a keyboard as an input device 930, in some embodiments the input device 930 can include other types of input devices, for example a touchscreen, stylus, keypad, or voice recognition system. A local unit can include a power source. For example, a local unit can include a solar cell, a battery or connect to a building power supply through a wire connection. A user 900, such as a medical caregiver, operates the local unit 940.

A user 900 can include a medical caregiver, such as a nurse or doctor, or a patient, patient family member or other individual monitoring the wound dressing. Although user 900 is shown/described herein as a single illustrated figure, those skilled in the art will appreciate that user 900 can be representative of a human user, a robotic user (e.g., computational entity), and/or substantially any combination thereof (e.g., a user can be assisted by one or more robotic agents) unless context dictates otherwise. Those skilled in the art will appreciate that, in general, the same can be said of "sender" and/or other entity-oriented terms as such terms are used herein unless context dictates otherwise. A user 900 may utilize a local unit 940 through a user interface, for example one or more buttons, a keyboard, a touchscreen, a voice recognition device, a stylus, or other means.

A local unit 940 can include a communication device including at least one transmitter. A local unit 940 can include a radio-frequency identification (RFID) receiver. A local unit 940 can include a near field communication (NFC) device. A local unit 940 can be configured to send and receive signals from a plurality of appurtenances. For example, a local unit 940 can be configured to send and receive signals from multiple appurtenances affixed to wound dressings on a single individual. For example, a local unit 940 can be configured to send and receive signals from multiple appurtenances affixed to wound dressings on multiple individuals in a defined area, such as a single room or region of a room. A local unit 940 can be configured to send signals to one or more wound dressings with attached appurtenances 125 automatically. For example, local unit 940 can be configured to send signals to one or more wound dressings with attached appurtenances 125 at least one of: every 30 minutes; every hour; every 2 hours; or every 3 hours. A local unit 940 can be configured to send signals to one or more wound dressings with attached appurtenances 125 on a schedule selected by the user 900. For example, local unit 940 can be configured to send signals to one or more wound dressings with attached appurtenances 125 on at least one of: an hourly schedule; a schedule of every 30 minutes for 4 hours, followed by hourly signals; or a schedule provided by the user through the user interface (e.g. the keyboard 930). A local unit 940 can be configured to send signals to one or more wound dressings with attached appurtenances 125 on a preset schedule which is selected by the user 900. For example, local unit 940 can be configured to send signals to one or more wound dressings with attached appurtenances 125 on at least one of: a schedule preset to monitor a wound after surgery; a schedule preset to monitor a chronic wound; an hourly schedule; a schedule of every 2 hours; a schedule of hourly during the day and every 2 hours at night; or other preset schedules.

The signals 910 sent from the local unit 940 to the wound dressing with attached appurtenance unit 125 can be radio frequency signals in a particular wavelength, or range of wavelengths. For example, the signals can be in the UHF range, such as a UHF sub-range commonly used in a particular geographic region. See, for example the "Worldwide RFID UHF Map" by Intelleflex Corporation (©2009), which is incorporated herein by reference. For example, the signals can be in a range of 902-928 MHz. For example, the signals can be in a range specified by an industry standard. For example, the signals can be in the approximately 13.56 megahertz (MHz) range, or within the ISO 14443 standard parameters. For example, the signals can be in the IEEE 802.11x standard or the Bluetooth standard range. See, for example, U.S. Pat. No. 7,215,976 to Brideglall, titled "RFID Device, System and Method of Operation Including a Hybrid Backscatter-based RFID Protocol Compatible with RFID, Bluetooth and/or IEEE 802.11x Infrastructure," which is incorporated herein by reference. For example, the signals can be in the approximately 131 kilohertz (KHz) range, for example as part of a RuBee™ (IEEE standard 1902.1) system (equipment sold, for example, by Visible Assets™, Inc.). See for example: the description of RuBee™ systems from the Visible Assets™ webpage; Stevens et al., "RuBee (IEEE 1902.1)—The Physics Behind, Real-Time, High Security Wireless Asset Visibility Networks in Harsh Environments," a white paper from Visible Assets™; and in US Patent Application No. 2007/0171076 to Stevens and Waterhouse, titled "Low-frequency Radio Tag Encapsulating System," each of which are incorporated herein by reference.

Similarly, the signals 910 sent from the wound dressing with attached appurtenance unit 125 to the local unit 940 can be one of the types described above in relation to signals 910 sent from the local unit 940. In some embodiments, the wound dressing with attached appurtenance unit 125 includes a backscatter or reflective transmission device, and so the signals 910 sent from the wound dressing with attached appurtenance unit 125 to the local unit 940 can be backscatter or reflective signals. For example, as described in "Fundamental Operating Principles," in Chapter 3 of the *RFID Handbook: Fundamentals and Applications in Contactless Smart Cards and Identification*, Klaus Finkenzeller, John Wiley & Sons, (2003), which is incorporated herein by reference herein.

The signals 910 transmitted from the local unit 940 or transmitted from the wound dressing with attached appurtenance unit 125 can be sent in a fixed direction from the signal source. The wound dressing with attached appurtenance unit 125 and the local unit 940 may each include markings or other visible aspects directing a user how as to orient the wound dressing with attached appurtenance unit 125 and the local unit 940 relative to each other for signal directionality.

In many embodiments, it is envisioned that the signal strength of a signal 910 transmitted from either the local unit 940 or transmitted from the wound dressing with attached appurtenance unit 125 will be such that the signal 910 will not travel a significant distance. The local unit 940 and the wound dressing with attached appurtenance unit 125 may, therefore, need to be placed in reasonably close proximity for signals 910 to travel between the devices. For example, the signal 910 transmitted from either the local unit 940 or transmitted from the wound dressing with attached appurtenance unit 125 can be such that the receiver of such signals should be within the same room. For example, the signal 910 transmitted from either the local unit 940 or transmitted from the wound dressing with attached appurtenance unit 125 can be such that the receiver of such signals should be within 10 feet. For example, the signal 910 transmitted from either the local unit 940 or transmitted from the wound dressing with attached appurtenance unit 125 can be such that the receiver of such signals should be within 3 feet.

Figure 10:
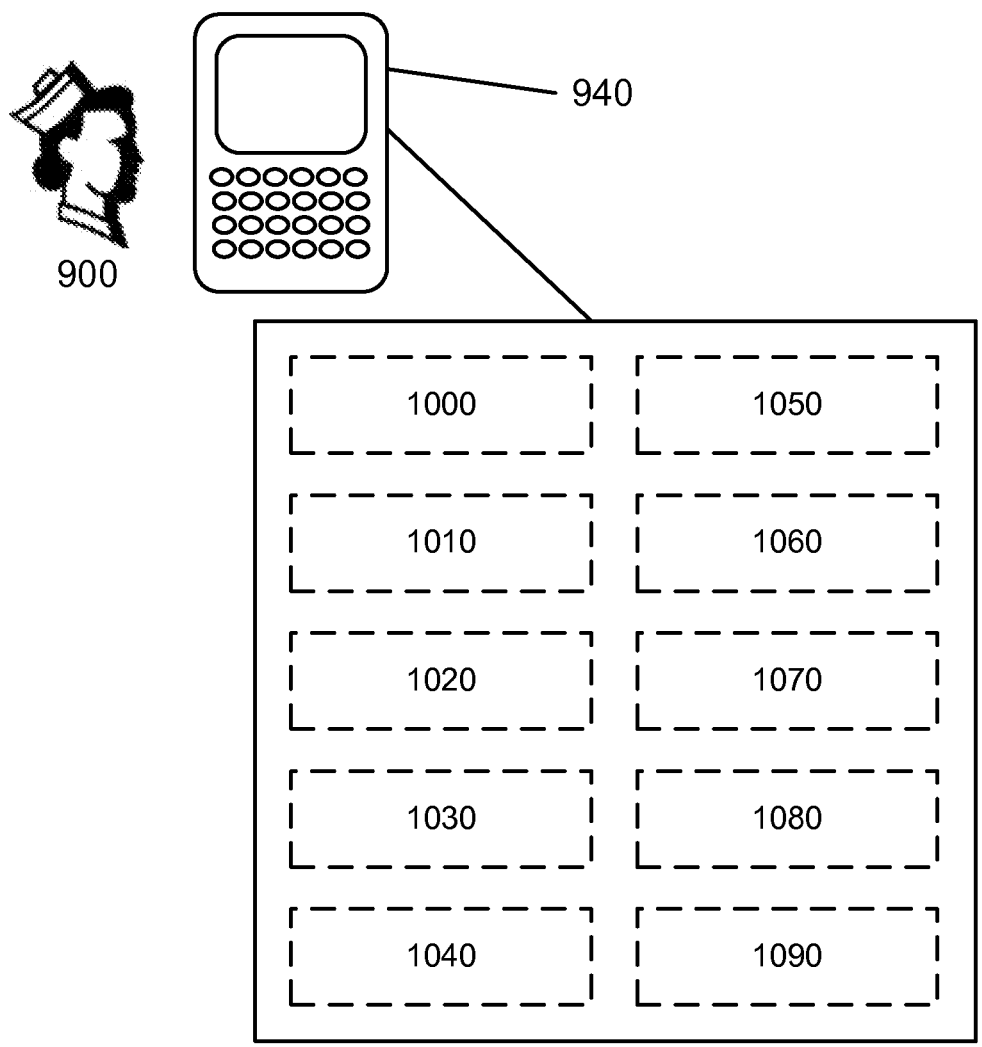
FIG. 10 is a schematic of an appurtenance to a wound dressing in communication with a local unit.
Figure 10:
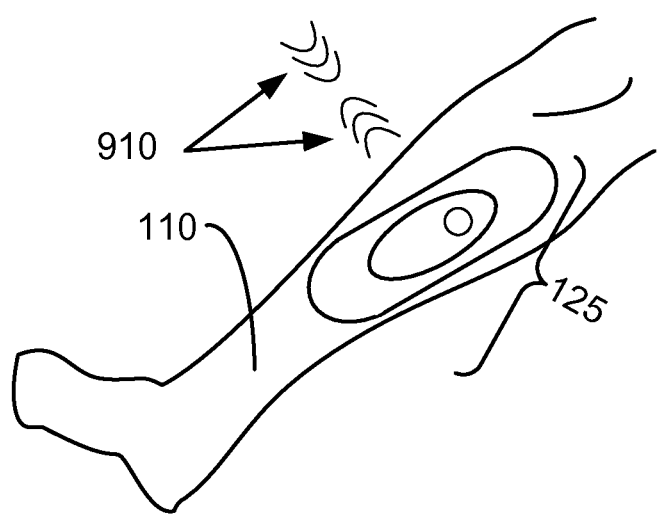

FIG. 10 illustrates aspects of a system including a wound dressing with an affixed appurtenance unit 125. As illustrated in FIG. 10, a wound dressing with an affixed appurtenance unit 125 is positioned over a wound on a body part 110 of a patient. The wound dressing with an affixed appurtenance unit 125 sends and receives signals 910 from a local unit 940. The local unit 940 can be utilized by a user 900.

FIG. 10 illustrates aspects of the local unit 940. The local unit 940 includes a housing, with connected user interface and input components (e.g. a display and keyboard). The local unit 940 can include a processor 1000. The local unit 940 can include memory 1010. The memory 1010 can include, for example, volatile and/or non-volatile memory. The local unit 940 can include at least one antenna 1020. The local unit 940 can include circuitry 1030, operably connected to the other components of the local unit. The local unit 940 can include one or more transmitters 1040. The local unit 940 can include one or more receivers 1050. The local unit 940 can include one or more power sources 1060, such as a battery, a solar cell, or a plug-in socket. The local unit 940 can include logic 1070. The local unit 940 can include other components 1080, 1090 as appropriate to a specific embodiment. The local unit 940 can include, for example, an application specific intelligent microsensor as described in U.S. Pat. No. 6,889,165 to Lind et al., titled "Application Specific Intelligent Microsensors," which is incorporated herein by reference herein.

In some embodiments, a processor of a local unit includes: circuitry configured to accept data received by the receiver from the transmitter unit of the appurtenance; circuitry configured to classify a subset of the received data as originating from the electronic identifier of the appurtenance; circuitry configured to classify a subset of the received data as originating from the sensor unit of the appurtenance; circuitry configured to compare the subset of the received data classified as originating from the sensor unit of the appurtenance with data in memory; and circuitry configured to initiate a signal to a system user in response to the comparison. For example, a local unit can include circuitry configured to identify a subset of the received data.

In some embodiments, a processor of a local unit includes: circuitry configured to accept data received by the receiver from the transmitter unit of the appurtenance; and circuitry configured to initiate a signal by the communication unit in response to the received data. For example, the circuitry can be configured to send a signal to a central assembly in response to the accepted data. For example, the circuitry can be configured to send a signal including at least a subset of the received data to a central assembly. In some embodiments, a processor of a local unit further includes: circuitry configured to initiate a signal to a user in response to the received data. For example, a local unit can include an indicator that is a LED light and include circuitry configured to illuminate the LED light in response to the received data.

In some embodiments, a processor of a local unit includes: circuitry configured to accept data received by the receiver from the transmitter unit of the appurtenance;

circuitry configured to classify at least one subset of the received data; circuitry configured to compare one or more classified subset of the received data with data in memory; and circuitry configured to initiate a signal to a user in response to the comparison. For example, a local unit can include a look-up table including data with identifiers for specific appurtenances, and include circuitry configured to initiate a message on a display in response to a comparison of received data with the data in the look-up table. For example, a look-up table can include specific patient names in association with unique electronic identifiers for specific appurtenances, and the local unit can include circuitry configured to indicate on a display a reading from the appurtenance associated with a patient. For example, a local unit can be configured to display a message such as "Signal from Mr. Jones' wound dressing-appurtenance combination unit received." For example, a local unit can be configured to display a message such as "Signal from appurtenance number 123 received."

In some embodiments, a processor of a local unit includes: circuitry configured to accept data received by the receiver from the transmitter unit of the appurtenance; circuitry configured to classify two or more subsets of the received data; circuitry configured to compare the two or more subsets of the received data with data in memory; circuitry configured to prioritize results from the comparisons; and circuitry configured to initiate a signal to a user in response to the prioritized results. For example, a local unit can include circuitry including a prioritization schedule for data from multiple sensors in one or more sensor units of a single appurtenance. A prioritization schedule can be designed, for example, to prioritize sensor data indicating medical priorities first. For example, a local unit can include circuitry configured to prioritize data indicating temperature of a wound dressing above 100 degrees F. as a higher priority than data indicating that the wound dressing is dry. For example, a local unit can include circuitry configured to prioritize data indicating presence of a specific bacterial protein as a higher priority than data indicating that the wound dressing is a temperature below 99 degrees F. A prioritization schedule can be designed, for example, to prioritize sensor data indicating user-defined priorities first. For example, local unit can include circuitry configured to prioritize data indicating the patient name associated with a specific electronic identifier of an appurtenance as a higher priority than sensor data from the appurtenance.

In some embodiments, a processor of a local unit includes: circuitry configured to add a time stamp to the accepted data received by the receiver from the transmitter unit of the appurtenance; circuitry configured to compare the time stamp with data in memory to generate an elapsed time value; circuitry configured to prioritize results from the comparisons and the elapsed time value; and circuitry configured to initiate a signal to a user in response to the prioritized results. For example, a local unit can include circuitry configured to calculate the elapsed time that an appurtenance has been in use, and compare the calculated elapsed time value with a preset value from a system user regarding a maximum elapsed time value between wound dressing changes for a particular patient, and display an alert message on a display of the local unit if the elapsed time value exceeds the preset maximum elapsed time value. In some embodiments, a processor of a local unit includes: circuitry configured to accept data received by the receiver from the transmitter unit of the appurtenance; circuitry configured to classify two or more subsets of the received data; circuitry configured to compare the two or more subsets of the received data with data in memory; circuitry configured to prioritize results from the comparisons into a binary output; and circuitry configured to initiate a signal to a user based on the binary output. For example, a local unit can include circuitry configured to display an alert message on a display of the local unit in response to one or more data values, such as a temperature value from a sensor above a maximum value, a positive indicator from a wetness sensor, or a detection of a specific bacterial protein. For example, a signal sent by a local unit to a user based on the binary output can include a display message such as "Dressing Change Indicated" or "No Dressing Change Indicated." For example, a signal sent by a local unit to a user based on the binary output can be a first message in response to a first binary output and a second message based on the second binary output.

A local unit can include a communications unit. For example, in some embodiments a communications unit of a local unit includes at least one of: a visual display, a sound generator, a vibrating unit, and one or more light displays. For example, in some embodiments a communications unit of a local unit includes at least one transmitter.

Figure 11:
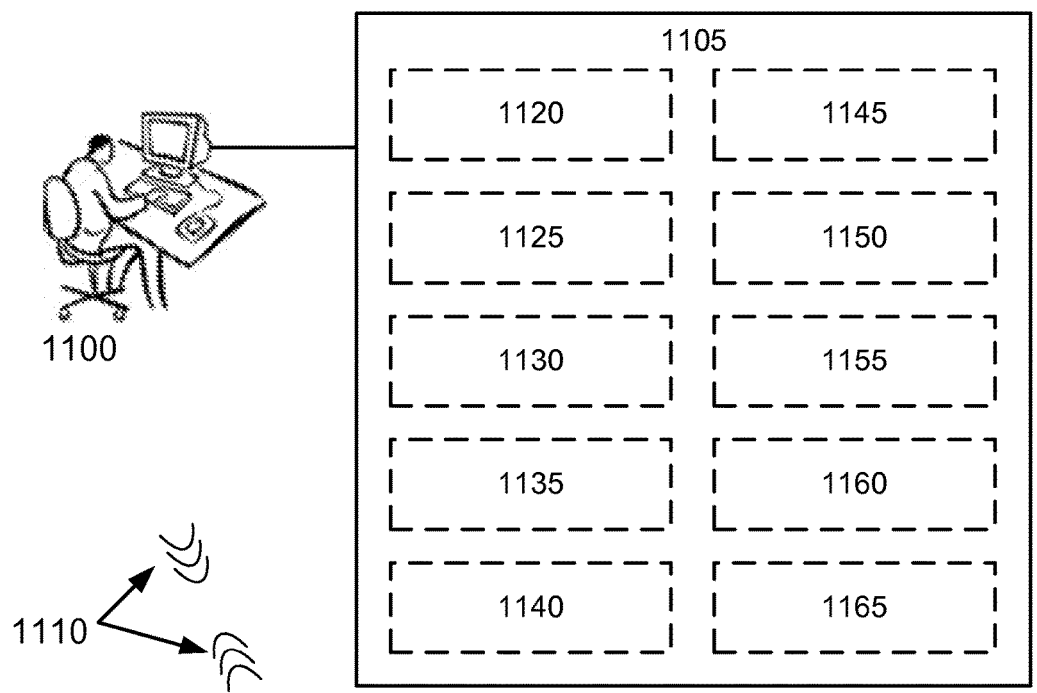
FIG. 11 is a schematic of an appurtenance to a wound dressing in communication with a local unit and a central assembly.
Figure 11:
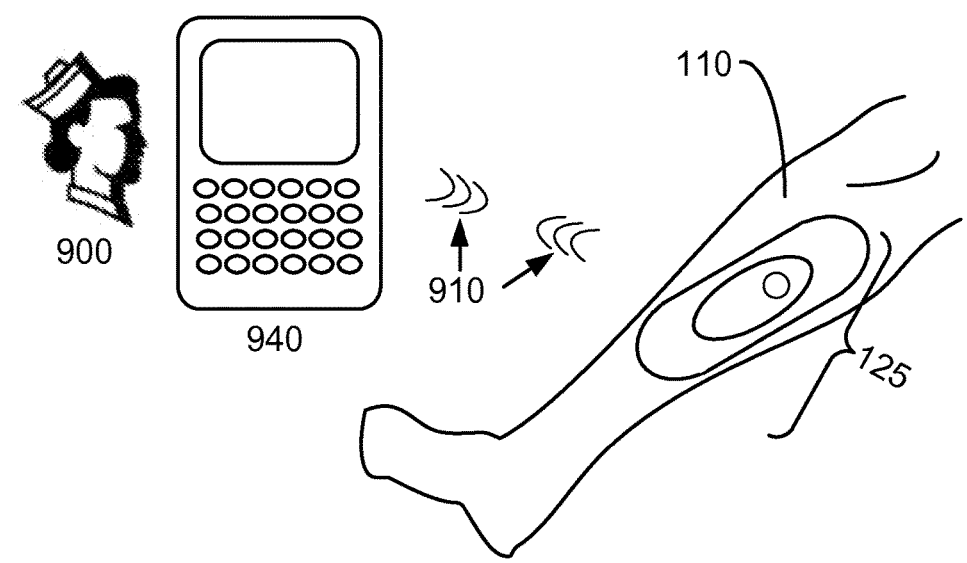

FIG. 11 shows aspects of a system including a wound dressing with an affixed appurtenance unit 125. As shown in FIG. 11, a wound dressing with an affixed appurtenance unit 125 is attached to a body part 110 of a patient over a wound. The wound dressing with an affixed appurtenance unit 125 sends and receives signals 910 from a local unit 940. The local unit 940 can be utilized by a user 900.

Also as shown in FIG. 11, the local unit 940 may send and receive signals 1110 from a central assembly 1105. The local unit 940 may send and receive signals 1110 with a wireless connection, as shown in FIG. 11, or the local unit 940 may send and receive signals 1110 through a wire connection. A central assembly 1105 includes at least one user interface device (e.g. a keyboard, touchscreen, display, etc.) which can be utilized by a system user 1100. A system user 1100 can include a medical caregiver, such as a nurse or doctor, or a patient caregiver, or other individual monitoring the wound dressing. Although system user 1100 is shown/described herein as a single illustrated figure, those skilled in the art will appreciate that system user 1100 can be representative of a human user, a robotic user (e.g., computational entity), and/or substantially any combination thereof (e.g., a user can be assisted by one or more robotic agents) unless context dictates otherwise. Those skilled in the art will appreciate that, in general, the same can be said of "sender" and/or other entity-oriented terms as such terms are used herein unless context dictates otherwise.

FIG. 11 illustrates aspects of some embodiments of a central assembly 1105. A central assembly 1105 can include a processor, a receiver configured to receive signals from the local unit 940, and at least one user interface. The central assembly 1105 can include, for example, at least one transmitter 1120. The central assembly 1105 can include a transmitter configured to send signals 1110 to the local unit 940. The central assembly 1105 can include a transmitter configured to send signals to one or more mobile devices. For example, the central assembly 1105 can include a transmitter configured to send signals to one or more cell phones, pagers, PDA devices, or mobile computing devices. For example, the central assembly 1105 can include a transmitter configured to send signals of a type received by the communication unit of the local unit. For example, the central assembly 1105 can include a transmitter configured to send signals of a type received by one or more mobile devices. The central assembly 1105 can include, for example, at least one receiver 1125. In some embodiments, the receiver of a central assembly is configured to interact with a computer system. The central assembly 1105 can include, for example, at least one antenna 1130. The central assembly 1105 can be configured to receive signals from a plurality of local units 940. For example, a central assembly 1105 can be configured to receive signals 1110 from all of the local units in a hospital, nursing home, care facility, or a section thereof. The central assembly 1105 can be configured to send signals to a plurality of local units. For example, a central assembly 1105 can be configured to send signals 1110 to all of the local units in a hospital, nursing home, care facility, or a section thereof. The central assembly 1105 can include memory 1135. The central assembly 1105 can include, for example, volatile and/or non-volatile memory. The central assembly 1105 can include, for example, circuitry 1140. The circuitry 1140 can be operably connected to other components of the central assembly 1105. The central assembly 1105 can include, for example, a power source 1145. A power source 1145 can include, for example, at least one battery, a plug-in connection, a wireless power source, or a solar cell. The central assembly 1105 can include, for example, a processor 1150. The central assembly 1105 can include, for example, logic 1155. The central assembly 1105 can include, for example, additional components 1160, 1165. The central assembly 1105 can include at least one display. The central assembly 1105 can include at least one indicator, such as a visible or auditory indicator. The central assembly 1105 can, for example, be coupled to one or more user display units. The central assembly 1105 can, for example, be coupled to one or more light indicators.

A central assembly 1105 can be located primarily or mainly in one or a limited number of machines, for example one or more computer servers. A central assembly 1105 can be configured to interact with a computer system. A central assembly 1105 may interface with, or include, a 2G-RFID-Based E-Healthcare system. See, for example, Chen et al., "A 2G-RFID-Based E-Healthcare System," IEEE Wireless Communications, February 2010, pages 37-43, which is incorporated herein by reference. A central assembly 1105 may interface with, or include, a digital management system, for example as discussed in: Fisher, "Indoor Positioning and Digital Management Emerging Surveillance Regimes in Hospitals" in T. Monahan (Ed), Surveillance and Security: Technological Politics and Power in Everyday Life (pp. 77-88), New York: Routledge (2006); and Fisher and Monahan, "Tracking the Social Dimensions of RFID Systems in Hospitals," *International Journal of Medical Informatics* 77 (2008) 176-183, which are each incorporated herein by reference. A central assembly 1105 may interface with, or include, a drug tracking system, as described, for example, in "RFID Systems for Pharmaceutical Distributors to Meet the New FDA Regulations on Drugs," white paper from Abhisam Software, (2006), which is incorporated herein by reference.

Figure 12:
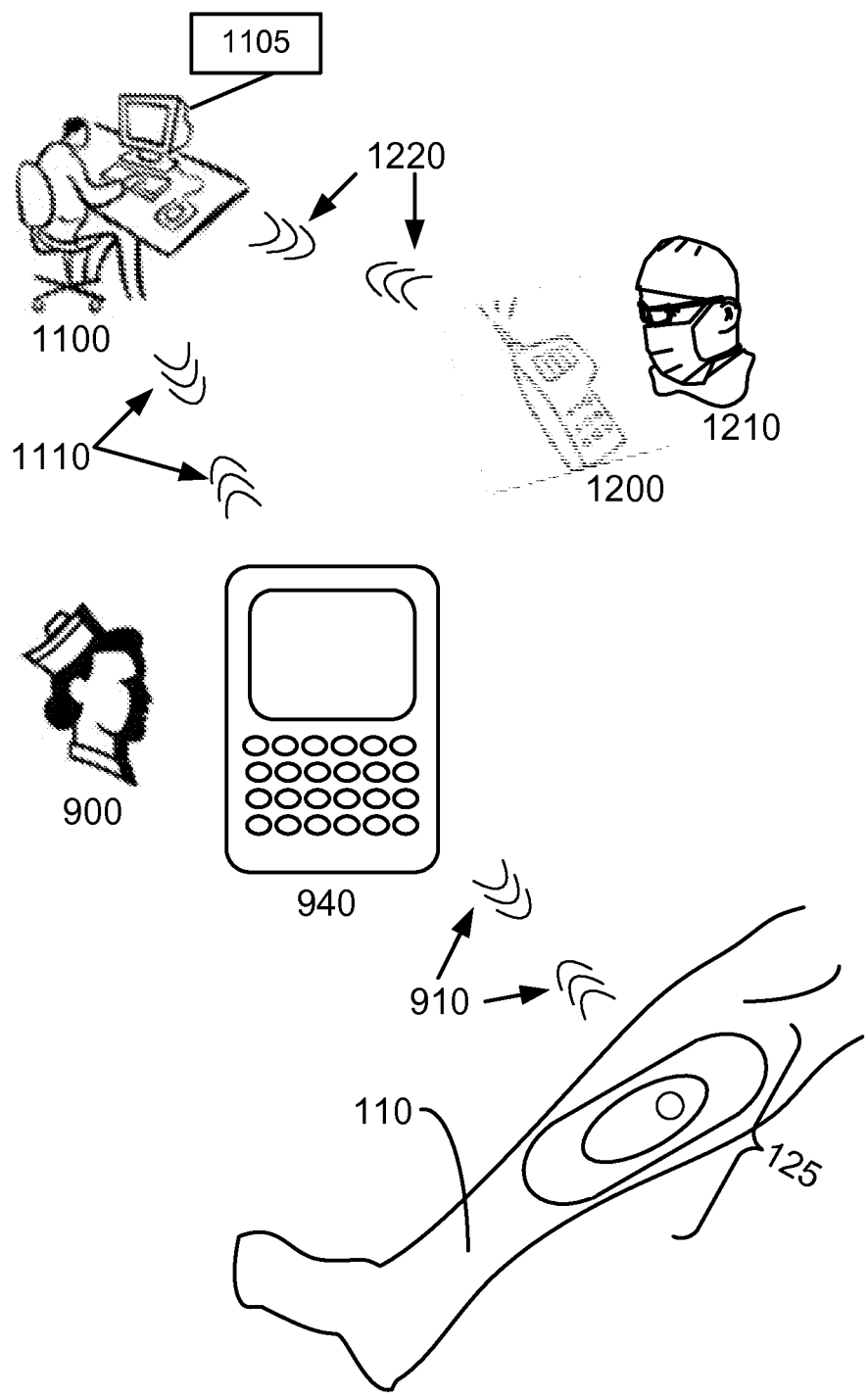
FIG. 12 is a schematic of an appurtenance to a wound dressing in communication with a local unit, a central assembly and a remote device.

FIG. 12 illustrates aspects of a system including a wound dressing with an affixed appurtenance unit 125. As shown in FIG. 12, a wound dressing with an affixed appurtenance unit 125 is placed over a wound on a body part 110 of a patient. The wound dressing with an affixed appurtenance unit 125 receives signals 910 from a local unit 940 and transmits signals 910 to the local unit 940. The local unit 940 can be utilized by a user 900.

Also as shown in FIG. 12, the local unit 940 may send and receive signals 1110 from a central assembly 1105. A system user 1100 interacts with a user interface device operably attached to the central assembly 1105. The central assembly 1105 sends signals 1220 to and receives signals 1220 from a remote device 1200. Although the signals 1220 illustrated in FIG. 12 are wireless signals 1220, in some embodiments the signals 1220 can be transmitted through a wire connection. The remote device 1200 can be, for example, a dedicated remote device 1200. The remote device 1200 can be, for example, integrated with another device, such as a laptop, cell phone, tablet computing device, pager, PDA, or personal computing device. The remote device can include specialized programming and/or circuitry to process the signal received from the central assembly. The remote device 1200 can be configured to initiate a warning indicator when it receives a signal 1220 from the central assembly 1105 regarding the wound dressing with an affixed appurtenance unit 125. For example, the remote device 1200 can be configured to initiate a warning light, display, auditory message, auditory tone, or vibration when it receives a signal 1220 from the central assembly 1105 regarding the wound dressing with an affixed appurtenance unit 125.

The remote device 1200 is configured for use by a remote user 1210. A remote user 1210 can include a medical caregiver, such as a nurse or doctor, or a patient caregiver, or other individual monitoring the wound dressing. Although remote user 1210 is shown/described herein as a single illustrated figure, those skilled in the art will appreciate that remote user 1210 can be representative of a human user, a robotic user (e.g., computational entity), and/or substantially any combination thereof (e.g., a user can be assisted by one or more robotic agents) unless context dictates otherwise. Those skilled in the art will appreciate that, in general, the same can be said of "sender" and/or other entity-oriented terms as such terms are used herein unless context dictates otherwise. The remote user 1210 may initiate the remote device 1200 to transmit a signal 1220 to the central assembly 1105, for example a signal 1220 indicating that a message has been received regarding the wound dressing with an affixed appurtenance unit 125.

Figure 13:
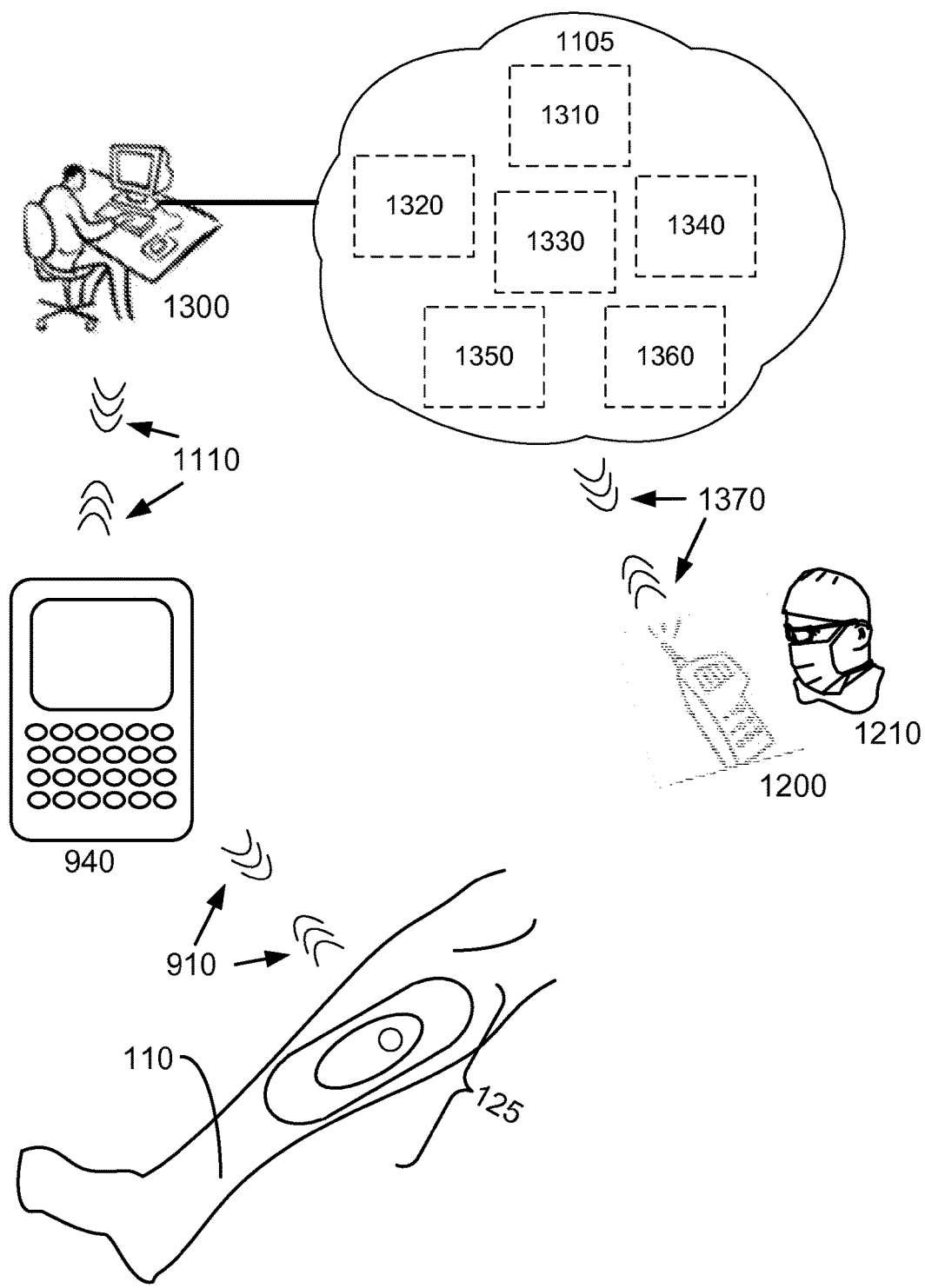
FIG. 13 is a schematic of an appurtenance to a wound dressing in communication with a local unit, a central assembly and a remote device.

FIG. 13 illustrates aspects of a system including a wound dressing with an affixed appurtenance unit 125. As illustrated in FIG. 13, a wound dressing with an affixed appurtenance unit 125 is placed over a wound on a body part 110 of a patient. The wound dressing with an affixed appurtenance unit 125 sends and receives signals 910 from a local unit 940. The local unit 940 sends and receives signals 1110 from a central assembly 1105. The central assembly 1105 illustrated in FIG. 13 is in a "cloud" format, with a significant portion of its components distributed on a computer network. The central assembly 1105 is configured to communicate with one or more interface devices 1300, for example an individual computer.

Depending on the embodiment, a cloud-based central assembly 1105 can include a plurality of components as illustrated in FIG. 13. For example, a central assembly 1105 can include logic 1310. For example, a central assembly 1105 can include circuitry 1320. The circuitry 1320 can be operably connected to other components of the central assembly 1105. For example, a central assembly 1105 can include memory 1330. For example, a central assembly 1105 can include one or more power sources 1340. For example, a central assembly 1105 can include at least one processor 1350. For example, a central assembly 1105 can include other components 1360.

Also as illustrated in FIG. 13, a central assembly 1105 may communicate with a remote device 1200 through signals 1370. Signals 1370 can be sent and received by an aspect of the central assembly 1105. Signals 1370 can be sent and received by the remote device 1200. Although the signals 1370 illustrated in FIG. 13 are wireless signals, in some embodiments the central assembly 1105 and a remote device 1200 may communicate through a wired connection. The remote device 1200 can be, for example, a pager, cell phone, laptop, PDA, tablet, smart phone or other device. The remote device 1200 can be operated by a remote system user 1210. Some embodiments include a plurality of remote devices 1200, which can be operated by a plurality of remote system users 1210.

In some embodiments, a wound dressing monitoring system includes: an appurtenance to a wound dressing, wherein the appurtenance includes a sensor unit including a resonance sensor, an electronic identifier, and a transmitter unit operably attached to the sensor unit and to the electronic identifier; and a local unit including a receiver for the transmitter unit, a processor operably attached to the receiver, and a communication unit operably attached to the processor. In some embodiments, the resonance sensor includes a passive RFID unit including a cavity resonator of a size and shape to be dampened when the wound dressing is substantially saturated with fluid, and further includes: a passive RFID including a unique identifier and a self-compensating antenna calibrated for use with the wound dressing.

Figure 14:
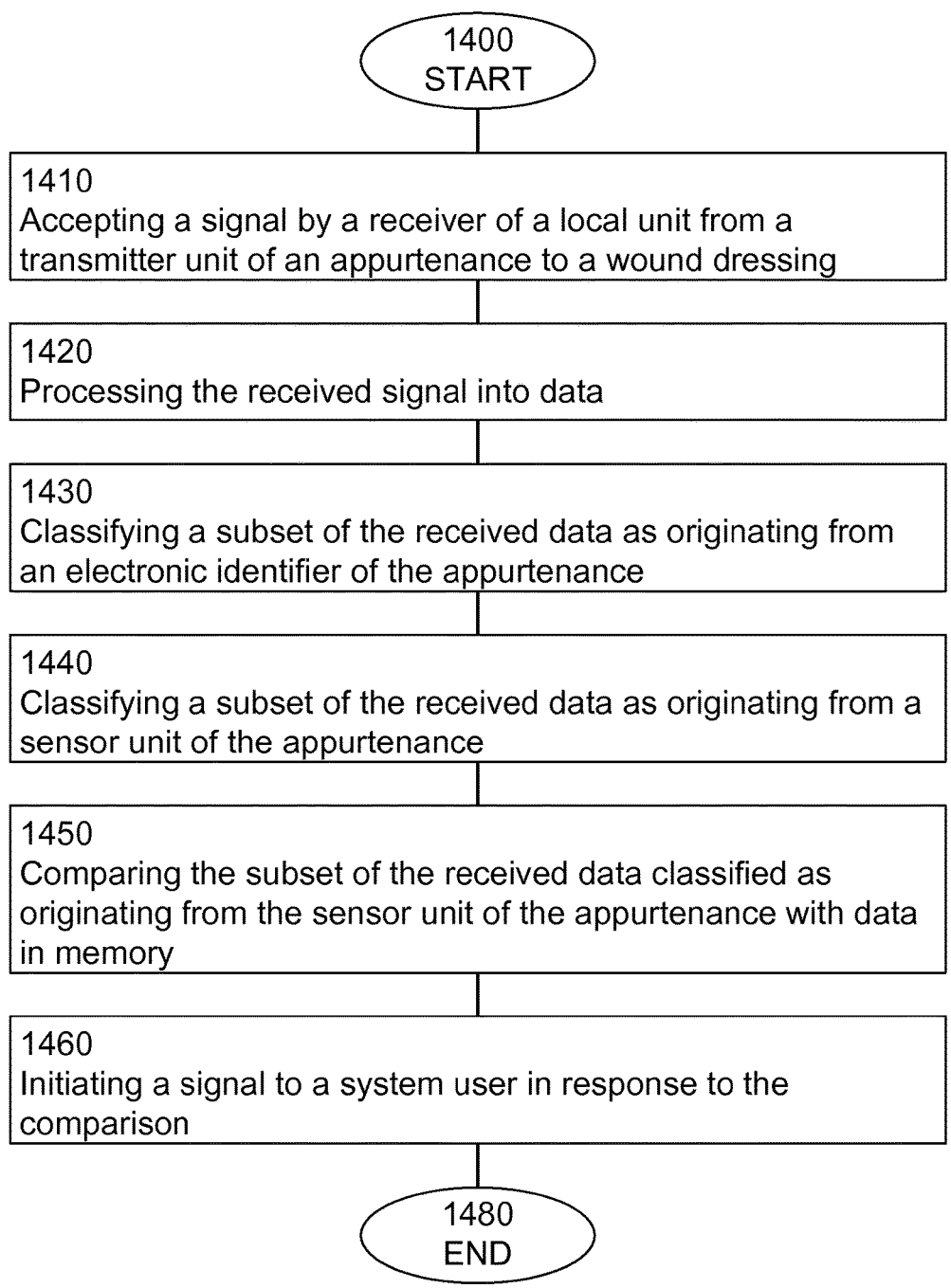
FIG. 14 is a flowchart of a method.

FIG. 14 illustrates aspects of a method utilizing the appurtenances described herein. As shown in FIG. 14, a method of monitoring an appurtenance attached to a wound dressing includes steps. Block 1400 illustrates the start of the method. Block 1410 shows accepting a signal by a receiver of a local unit from a transmitter unit of an appurtenance to a wound dressing. Block 1420 depicts processing the received signal into data. Block 1430 illustrates classifying a subset of the received data as originating from an electronic identifier of the appurtenance. Block 1440 shows classifying a subset of the received data as originating from a sensor unit of the appurtenance. Block 1450 depicts comparing the subset of the received data classified as originating from the sensor unit of the appurtenance with data in memory. Block 1460 illustrates initiating a signal to a system user in response to the comparison.

Some embodiments include additional aspects of the method illustrated in FIG. 14. In some embodiments the method step of accepting a signal by a receiver of a local unit from a transmitter unit of an appurtenance to a wound dressing includes receiving a RFID signal. In some embodiments the method step of accepting a signal by a receiver of a local unit from a transmitter unit of an appurtenance to a wound dressing includes receiving a near field communication signal. For example, a RFID signal and/or a near field communication signal can be sent by a transmitter unit of the appurtenance affixed to the wound dressing, and the signal received by the local unit.

In some embodiments, the method step of processing the received signal into data includes identifying subgroups of signals within the received signal. For example, processing the received signal into data can include the processor of a local unit identifying parts of the signal with identifying features of a subgroup, such as specific signal components or repeated signal components.

In some embodiments, the method step of classifying a subset of the received data as originating from an electronic identifier of the appurtenance includes: identifying a subset of the data as including an identifier of an appurtenance; and denoting the subset of data including an identifier of an appurtenance in stored memory. For example, a local unit can identify data as originating from an electronic identifier as beginning with a specific code or repeated pattern, such as, for example, "1234." For example, a local unit can identify data as originating from an electronic identifier as including an identifier number of a specific length, such as, for example, 15 numerals long, 20 numerals long, 25 numerals long, or 30 numerals long. In some embodiments, the method step of classifying a subset of the received data as originating from an electronic identifier of the appurtenance includes: identifying a subset of the data as including an identifier of a sensor; and denoting the subset of data including an identifier of a sensor in stored memory. For example, data from a sensor type can include an identifying code. For example, data from a specific sensor unit can include an identifying code. In some embodiments, the method step of classifying a subset of the received data as originating from an electronic identifier of the appurtenance includes: identifying a subset of the data as including an identifier of a sensor unit; identifying the type of sensor included in the sensor unit from stored memory; and denoting the subset of data including an identifier of a sensor unit in stored memory. For example, an identifier of a sensor unit in a subset of data can include a starting and ending code within the data surrounding the identifier. For example, identifying the type of sensor included in the sensor unit from stored memory can include looking up a code denoting a type of sensor unit in a look-up table. For example, denoting the subset of data including an identifier of a sensor unit in stored memory can include bracketing the subset of data including an identifier of a sensor unit with a machine-readable code. For example, denoting the subset of data including an identifier of a sensor unit in stored memory can include storing the subset of data including an identifier of a sensor unit in a specific location in stored memory.

In some embodiments, the method step of initiating a signal to a system user in response to the comparison includes: identifying the comparison result; identifying a signal type associated with the identified comparison result in stored memory; and initiating the local unit to begin the identified signal type. For example, identifying the comparison result can include identifying a positive result. For example, identifying the comparison result can include identifying a negative result. For example, identifying a signal type associated with the identified comparison result in stored memory can include looking up a comparison result in a look-up table in stored memory. For example, initiating the local unit to begin the identified signal type can include initiating display of a specific message on a display unit of the local unit. For example, a specific message can include "Dressing Change Indicated." For example, a specific message can include "Dressing Change Not Indicated." A specific message can include, for example, color and/or graphics.

In some embodiments, the method steps of a method of monitoring a wound dressing, as diagrammed in FIG. 14, can include additional steps. In some embodiments, the method steps of a method of monitoring a wound dressing can include initiating a signal by the local unit in response to the received data. For example, the method can include initiating a signal by a communication unit of the local unit in response to the received data. For example, in response to the received data a signal including the received data can be initiated from the communication unit of the local unit to a central assembly. For example, in response to the received data a signal including the received data can be initiated from the communication unit of the local unit to a repeater unit. For example, in response to the received data a signal including the received data can be initiated from the communication unit of the local unit to a logging unit including memory.

In some embodiments, the method steps of a method of monitoring a wound dressing can include: classifying at least one subset of the received data; comparing one or more classified subsets of the received data with data in memory in the local unit; and initiating a signal from the local unit in response to the comparison. For example, at least one subset of the received data can include an identifier of a patient, and be classified as such. This data can then be compared to a look-up table in memory including patients' names associated with identification codes. A method can include initiating a signal to a display of the local unit in response to the comparison, for example "Reading Mrs. Smith's wound dressing monitor." In a situation wherein a comparison finds no associated data in memory, a method can include initiating a signal to a display of the local unit in response to the comparison, for example "no patient identification available."

In some embodiments, the method steps of a method of monitoring a wound dressing can include: classifying two or more subsets of the received data; comparing the two or more subsets of the received data with data in memory in the local unit; prioritizing results from the comparisons; and initiating a signal from the local unit in response to the prioritized results. For example, a look-up table for data from a sensor unit of an appurtenance can include parameters or standards for data that will lead to a "check dressing" or "dressing change required" graphic to be initiated on the local unit display. For example, if a comparison indicates that some data from a sensor unit is over a maximum value, then a corresponding message can be initiated on a display of the local unit. For example, a method and system can be calibrated to automatically display a "check dressing" or "dressing change required" graphic if the temperature reading from a sensor unit of an appurtenance is over 100 degrees F. For example, a method and system can be calibrated to automatically display a "check dressing" or "dressing change required" graphic if a fluid sensor indicates saturation of the wound dressing. For example, a method and system can be calibrated to automatically display a "check dressing" or "dressing change required" graphic if a sensor unit from the appurtenance indicates the presence of a specific bacterial protein.

In some embodiments, the method steps of a method of monitoring a wound dressing can include: adding a time stamp to the received data; comparing the time stamp with data in memory in the local unit to generate an elapsed time value; prioritizing results from the comparisons and the elapsed time value; and initiating a signal from the local unit in response to the prioritized results. For example, a wound dressing can be preset by a healthcare provider as requiring change after a specific time has elapsed for use of the wound dressing. For example, a healthcare provider can preset a system for monitoring a wound dressing to send an alert after the dressing has been in place for 6 hours, 12 hours, 24 hours, 36 hours, 48 hours, 72 hours, 4 days, 5 days, 6 days or 7 days. For example, a wound dressing can be preset by a healthcare provider as requiring change a specific point after a medical intervention. For example, a healthcare provider can preset a system for monitoring a wound dressing to send an alert after a surgery has been finished for 3 hours, 6 hours, 12 hours, 24 hours, 36 hours, 48 hours, or 72 hours.

In some embodiments, the method steps of a method of monitoring a wound dressing can include: classifying two or more subsets of the received data; comparing the two or more subsets of the received data with data in memory; prioritizing results from the comparisons into a binary output; and initiating a signal by the local unit based on the binary output. For example, in some embodiments an appurtenance to a wound dressing includes a plurality of sensors in one or more sensor units. In addition, a system can monitor the length of time that an appurtenance has been in place on a wound dressing over a wound. In response to multiple types of data coming into a wound monitoring system, a method can prioritize the data into a binary output (e.g. change dressing/dressing change not needed) and then initiate the display of an appropriate message on the local unit. For example, in some embodiments, data from the sensors can be prioritized by giving relative scores to the data based on a look-up table including relative scores for various data values (see, e.g. Table 1), followed by a calculation of a total score based on the entirety of the data. A binary output can be calculated based on the total score, such as being above or below a threshold value for the total score, and a corresponding signal displayed.

EXAMPLES

Example 1

An Appurtenance Including a Resonance Sensor

An appurtenance to a wound dressing is fabricated to include a resonance sensor positioned for detection of substantial saturation of a wound dressing with wound fluid. The appurtenance includes a substrate with a surface of a size and shape to reversibly mate with a substantially planar surface of a wound dressing. The substrate is fabricated from a polypropylene sheet of approximately 0.5 mm in thickness. The appurtenance includes an attachment unit of a size and shape to affix the substrate to the wound dressing, with the surface of the substrate in direct contact with the surface of the wound dressing. The attachment unit of the appurtenance includes a projection of a size and shape to be affixed to an aperture of a corresponding size and shape in the wound dressing. The projection of the attachment unit is positioned at substantially right angles to the surface of the substrate of a size and shape to reversibly mate with a surface of a wound dressing. The attachment unit is fabricated from a firm PET plastic. The attachment unit includes a ring of a size and shape to mate with the end of the projection and clamp on, thereby securing the projection within the aperture in the wound dressing.

A resonance sensor is affixed to the substrate. The resonance sensor includes a passive RFID unit with a cavity resonator of a size and shape to come into contact at a surface with the wound dressing when the appurtenance is in place. The cavity resonator is of a sufficient size for adjacent fluid in the wound dressing to dampen the cavity resonance during use. For a wound dressing that includes a gauze sponge that is a four inch square (i.e. a "4×4") on its largest surface and 12-ply thickness, a passive RFID unit is selected that includes a cavity resonator that is one inch square.

Prior to use, a 4×4, 12-ply gauze sponge wound dressing is selected with a precut aperture of a size and shape to mate with the exterior surface of the projection. The projection is pushed through the aperture and the appurtenance secured in place with the attachment of the ring. The resonance sensor, including the passive RFID with the cavity resonator, is positioned against the surface of the wound dressing away from the surface intended for use with a wound.

Example 2

Test Use of an Appurtenance Including a Resonance Sensor

A test device for an appurtenance including a resonance sensor was constructed including a plastic block with a substantially planar top surface approximately 4.5 inches square. A substantially horizontal channel was cut in the side of the block, and connected to an external section of tubing. Multiple vertical channels were cut into the block from the top surface to the substantially horizontal channel internal to the block. During use, fluid from a syringe attached to the external tubing was pushed into the block where it flowed through the internal channels and out of the vertical channels connecting to the top surface of the block. The fluid flow was used to mimic fluid of a wound under a wound dressing for testing purposes.

A metal frame was constructed of aluminum. The metal frame was fabricated to be a size and shape to reversibly mate with the external edge of the top surface of the block. The metal frame was approximately one half inch wide and of sufficient thickness and mass to hold the edges of a wound dressing in position against the top surface of the block during testing, while leaving the center of the wound dressing uncovered.

A 4×4, 12-ply gauze sponge wound dressing with an attached appurtenance including a resonance sensor as described in Example 1 was selected for testing. The wound dressing-appurtenance combination unit was positioned on the top of the block. The metal frame was placed over the wound dressing edges, securing the lower surface of the wound dressing against the top surface of the block.

A handheld RFID reader was used to scan the dry wound dressing-appurtenance combination unit on the test block from a distance of approximately 6 inches. The handheld reader was able to detect the passive RFID within the resonance sensor affixed to the dry wound dressing. Software within the reader was configured to indicate the detection on a screen with the text "dressing OK." Fluid was then pushed into the block from an attached syringe, and the wound dressing became visibly wet within 30 seconds. After the wound dressing was visibly wet, the handheld reader was used to scan the wet wound dressing-appurtenance combination unit on the test block from a distance of approximately 6 inches. The handheld reader was not able to detect the passive RFID within the resonance sensor affixed to the wet wound dressing. Software within the reader was configured to indicate the lack of detection on a screen with the text "check dressing."

Example 3

Hypothetical Evaluation of Data from an Appurtenance

An appurtenance to a wound dressing is applied to a wound dressing and then used to cover a patient's wound. Directly after application of the wound dressing, a healthcare provider uses a local unit that is a handheld device to scan the appurtenance, and then to enter the patient's identification into the system in relation to the appurtenance. Periodically, a healthcare provider returns to re-scan the wound dressing with the attached appurtenance using a local unit.

Data from the appurtenance is transmitted to the local unit, which receives the transmitted signal and then processes the signal to generate data from the appurtenance. The local unit also adds a time value to the processed data to indicate the time that the data was received. The local unit classifies the received data into subsets, including subsets of data from: an identifier, data from a temperature sensor, data from a first sensor including an aptimer that specifically recognizes a unique bacterial protein, and data from a second sensor including the aptimer that specifically recognizes the unique bacterial protein. The data from the temperature sensor is processed into a received temperature value. The data from the time associated with the initial scan of the appurtenance and the time the data was received is used to calculate an elapsed time, which is compared with a preset maximum use time. The data from each of the bacterial sensors is processed into a numerical value, which is expected to be between 1 and 100. Each of the processed data values is saved in memory in the local unit, and is accessible as part of the patient's record.

The local unit then scores the data values for each of the subsets using a look-up table, reproduced in a readable form as Table 1.

TABLE 1

A Data Scoring Table

| Data Source | Received Data Value | Score |
| --- | --- | --- |
| Temperature sensor | 100 degrees F. or above | 1 |
| Temperature sensor | Below 100 degrees F. | 0 |
| Elapsed time in use | Less than 80% of preset maximum time | 0 |
| Elapsed time in use | Between 80% to 100% of preset maximum time | 0.5 |
| Elapsed time in use | 100% of preset maximum time or above | 1 |
| Sensor 1 (bacteria protein) | X | .005X |
| Sensor 2 (bacteria protein) | X | .005X |

After the data from each subset is given a score based on the look-up table, the total score for the combined subsets of data is calculated by adding the total scores. If the total score has a value of 1 or above, the local unit initiates a "check dressing" message to a user via the display. If the total score has a value of less than 1, the local unit initiates a "dressing acceptable" message to a user via the display. The system generates a simple, binary response (e.g. yes check/no check) for convenience of a direct healthcare provider, while retaining the more complex data values for later evaluation as needed.

The herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some implementations described herein, logic and similar implementations may include computer programs or other control structures. Electronic circuitry, for example, may have one or more paths of electrical current constructed and arranged to implement various functions as described herein. In some implementations, one or more media may be configured to bear a device-detectable implementation when such media hold or transmit device detectable instructions operable to perform as described herein. In some variants, for example, implementations may include an update or modification of existing software (e.g., a high-level computer program serving as a hardware specification) or firmware, or of gate arrays or programmable hardware, such as by performing a reception of or a transmission of one or more instructions in relation to one or more operations described herein. Alternatively or additionally, in some variants, an implementation may include special-purpose hardware, software (e.g., a high-level computer program serving as a hardware specification), firmware components, and/or general-purpose components executing or otherwise invoking special-purpose components. Specifications or other implementations may be transmitted by one or more instances of tangible transmission media as described herein, optionally by packet transmission or otherwise by passing through distributed media at various times.

Alternatively or additionally, implementations may include executing a special-purpose instruction sequence or invoking circuitry for enabling, triggering, coordinating, requesting, or otherwise causing one or more occurrences of virtually any functional operation described herein. In some variants, operational or other logical descriptions herein may be expressed as source code and compiled or otherwise invoked as an executable instruction sequence. In some contexts, for example, implementations may be provided, in whole or in part, by source code, such as C++, or other code sequences. In other implementations, source or other code implementation, using commercially available and/or techniques in the art, may be compiled/implemented/translated/converted into a high-level descriptor language (e.g., initially implementing described technologies in C or C++ programming language and thereafter converting the programming language implementation into a logic-synthesizable language implementation, a hardware description language implementation, a hardware design simulation implementation, and/or other such similar mode(s) of expression). For example, some or all of a logical expression (e.g., computer programming language implementation) may be manifested as a Verilog-type hardware description (e.g., via Hardware Description Language (HDL) and/or Very High Speed Integrated Circuit Hardware Descriptor Language (VHDL)) or other circuitry model which may then be used to create a physical implementation having hardware (e.g., an Application Specific Integrated Circuit). Those skilled in the art will recognize how to obtain, configure, and optimize suitable transmission or computational elements, material supplies, actuators, or other structures in light of these teachings.

In an embodiment, several portions of the subject matter described herein may be implemented via Application Specific Integrated Circuits (ASICs), Field Programmable Gate Arrays (FPGAs), digital signal processors (DSPs), or other integrated formats. However, some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software (e.g., a high-level computer program serving as a hardware specification) and or firmware would be well within the skill of one of skill in the art in light of this disclosure.

In a general sense, the various embodiments described herein can be implemented, individually and/or collectively, by various types of electro-mechanical systems having a wide range of electrical components such as hardware, software (e.g., a high-level computer program serving as a hardware specification), firmware, and/or virtually any combination thereof, and a wide range of components that may impart mechanical force or motion such as rigid bodies, spring or torsional bodies, hydraulics, electro-magnetically actuated devices, and/or virtually any combination thereof. Consequently, as used herein "electro-mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs (e.g., graphene based circuitry). Examples of electro-mechanical systems include but are not limited to a variety of consumer electronics systems, medical devices, as well as other systems such as motorized transport systems, factory automation systems, security systems, and/or communication/computing systems. "Electro-mechanical," as used herein, is not necessarily limited to a system that has both electrical and mechanical actuation except as context may dictate otherwise.

In a general sense, the various aspects described herein which can be implemented, individually and/or collectively, by a wide range of hardware, software (e.g., a high-level computer program serving as a hardware specification), firmware, and/or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). The subject matter described herein may be implemented in an analog or digital fashion or some combination thereof.

All of the above U.S. patents, U.S. patent application publications, U.S. patent applications, foreign patents, foreign patent applications and non-patent publications referred to in this specification and/or listed in any Application Data Sheet, are incorporated herein by reference, to the extent not inconsistent herewith.

While various aspects and embodiments have been disclosed herein, other aspects and embodiments will be apparent. The various aspects and embodiments disclosed herein are for purposes of illustration and are not intended to be limiting, with the true scope and spirit being indicated by the following claims.

What is claimed is:

1. An appurtenance to a wound dressing, comprising:
a substrate including a bottom wall, the bottom wall including a surface of a size and shape to mate with a surface of the wound dressing, the substrate defining an interior space and including a flexible divider disposed in the interior space, the flexible divider extending upwardly from the bottom wall, the flexible divider separating the substrate into a first lateral section and a second lateral section, the first lateral section and the second lateral section extending upwardly from at least a portion of the bottom wall, the flexible divider configured to minimize fluid flow between the first lateral section and the second lateral section, wherein each of the first lateral section and the second lateral section includes an at least partially enclosed compartment;
a plurality of projections that project from the substrate, the plurality of projections are configured to pierce the wound dressing, at least one of the plurality of projections exhibiting a shape that generally tapers from a proximal end thereof to a distal end thereof, wherein the proximal end is adjacent to the substrate and the distal end is spaced from the substrate;
a sensor unit affixed to the substrate;
an electronic identifier affixed to the substrate; and
a transmitter unit operably attached to the sensor unit and to the electronic identifier, the transmission unit including circuitry configured to transmit information associated with the sensor unit and the transmitter unit.

2. The appurtenance of claim 1, wherein the sensor unit comprise: a chemical sensor.

3. The appurtenance of claim 1, wherein the sensor unit comprises:
a resonance sensor.

4. The appurtenance of claim 1, wherein the sensor unit comprises:
a plurality of sensors within the sensor unit.

5. The appurtenance of claim 1, wherein the electronic identifier comprises:
an RFID unit.

6. The appurtenance of claim 1, wherein the electronic identifier comprises:
an electronic code.

7. The appurtenance of claim 1, comprising:
at least two sensor units, the sensor units positioned on opposing ends of the substrate.

8. The appurtenance of claim 7, wherein the flexible divider is positioned between at least two of the sensor units.

9. The appurtenance of claim 1, further comprising:
a desiccant material in fluid communication with the wound dressing.

10. The appurtenance of claim 1, further comprising: a channel internal to at least one of the plurality of projections, the channel attached to a first aperture at a distal end of the projection, the channel attached to a second aperture positioned adjacent to the substrate; and an enclosed tubular structure attached to the substrate, the enclosed tubular structure affixed to the second aperture at a first end, the tubular structure affixed to the sensor unit at a second end.

11. The appurtenance of claim 10, further comprising:
one or more walls forming a gas-sealed chamber attached to the enclosed tubular structure, the gas-sealed chamber including an internal gas pressure below atmospheric pressure; and
a breakable seal between the gas-sealed chamber and the enclosed tubular structure.

12. The appurtenance of claim 1, wherein the plurality of projections are configured to reversibly mate with the surface of the wound dressing.

13. The appurtenance of claim 1, wherein:
the plurality of projections includes at least one first projection that fluidly couples the first lateral section to the wound dressing and at least one second projection that fluidly couples the second lateral section to the wound dressing; and
the sensor unit includes a first sensor unit disposed in the first lateral section and a second sensor unit disposed in the second lateral section.

14. The appurtenance of claim 1, wherein the flexible divider includes a thin plastic sheet.

15. The appurtenance of claim 1, further comprising a first section of a desiccant or sorbent material disposed in the first section and a second section of the desiccant or sorbent material disposed in the second section.

16. The appurtenance of claim 1, wherein the sensor unit is deposed in a portion of at least one of the plurality of projections that is configured to pierce the wound dressing, wherein the sensor unit is configured to detect one or more characteristics of the wound dressing or an individual using the wound dressing.

17. The appurtenance of claim 1, wherein:
the substrate includes a first edge and a second edge, the surface extending between the first edge and the second edge; and
the plurality of projections includes at least one first projection attached to the first edge and at least one second projection attached to the second edge.

18. The appurtenance of claim 1, wherein at least two of the plurality of projects extend outward in substantially same place as the surface of the substrate.

19. A wound dressing monitoring system, comprising:
an appurtenance to a wound dressing, wherein the appurtenance includes
a substrate including a bottom wall, the bottom wall including a surface configured to mate with a surface of the wound dressing, the substrate defining an interior space and including a flexible divider disposed in the interior space, the flexible divider extending upwardly from the bottom wall, the flexible divider separating the interior space of the substrate into a first lateral section and a second lateral section, the first lateral section and the second lateral section extending upwardly from at least a portion of the bottom wall, the flexible divider configured to minimize fluid flow between the first lateral section and the second lateral section, wherein each of the first lateral section and the second lateral section includes an at least partially enclosed compartment;
a plurality of projections that project from the substrate, the plurality of projections are configured to pierce the wound dressing, at least one of the plurality of projections exhibiting a shape that generally tapers from a proximal end thereof to a distal end thereof, wherein the proximal end is adjacent to the substrate and the distal end is spaced from the substrate;
a sensor unit;
an electronic identifier; and
a transmitter unit operably attached to the sensor unit and to the electronic identifier; and
a local unit including a receiver for the transmitter unit, a processor operably attached to the receiver, and a communication unit operably attached to the processor.

20. The system of claim 19, wherein the transmitter unit included in the appurtenance comprises:
a radio-frequency identification (RFID) transmitter.

21. The system of claim 19, wherein the transmitter unit included in the appurtenance comprises:
a near field communication (NFC) device.

22. The system of claim 19, wherein the processor comprises:
first circuitry configured to accept data received by the receiver from the transmitter unit of the appurtenance;
second circuitry configured to classify a subset of the received data as originating from the electronic identifier of the appurtenance;
third circuitry configured to classify a subset of the received data as originating from the sensor unit of the appurtenance;
fourth circuitry configured to compare the subset of the received data classified as originating from the sensor unit of the appurtenance with data in memory; and
fifth circuitry configured to initiate a signal to a system user in response to the comparison;
wherein the first circuitry, the second circuitry, the third circuitry, the fourth circuitry, and the fifth circuitry form at least one circuitry.

23. The system of claim 19, wherein the processor comprises:
first circuitry configured to accept data received by the receiver from the transmitter unit of the appurtenance; and
second circuitry configured to initiate a signal by the communication unit in response to the received data;
wherein the first circuitry and the second circuitry form at least one circuitry.

24. The system of claim 23, wherein the processor comprises:
third circuitry configured to initiate a signal to a user in response to the received data;
wherein the first circuitry, second circuitry, and the third circuitry form at least one circuitry.

25. The system of claim 19, wherein the processor comprises:
first circuitry configured to accept data received by the receiver from the transmitter unit of the appurtenance;
second circuitry configured to classify two or more subsets of the received data;
third circuitry configured to compare the two or more subsets of the received data with data in memory;
fourth circuitry configured to prioritize results from the comparisons; and
fifth circuitry configured to initiate a signal to a user in response to the prioritized results;
wherein the first circuitry, the second circuitry, the third circuitry, the fourth circuitry, and the fifth circuitry form at least one circuitry.

26. The system of claim 25, wherein the processor comprises:
sixth circuitry configured to add a time stamp to the accepted data received by the receiver from the transmitter unit of the appurtenance;
seventh circuitry configured to compare the time stamp with data in memory to generate an elapsed time value;
eighth circuitry configured to prioritize results from the comparisons and the elapsed time value; and
ninth circuitry configured to initiate a signal to a user in response to the prioritized results;
wherein the first circuitry, the second circuitry, the third circuitry, the fourth circuitry, the fifth circuitry, the sixth circuitry, the seventh circuitry, the eighth circuitry, and the ninth circuitry form at least one circuitry.

27. The system of claim 19, wherein the processor comprises:
first circuitry configured to accept data received by the receiver from the transmitter unit of the appurtenance;
second circuitry configured to classify two or more subsets of the received data;
third circuitry configured to compare the two or more subsets of the received data with data in memory;
fourth circuitry configured to prioritize results from the comparisons into a binary output; and
fifth circuitry configured to initiate a signal to a user based on the binary output;
wherein the first circuitry, the second circuitry, the third circuitry, the fourth circuitry, and the fifth circuitry form at least one circuitry.

28. The system of claim 19, comprising:
a central assembly, including a central assembly processor, a central assembly receiver configured to receive signals from the communication unit, and a user interface.

* * * * *

UNITED STATES PATENT AND TRADEMARK OFFICE
CERTIFICATE OF CORRECTION

PATENT NO. : 10,265,219 B2
APPLICATION NO. : 14/252136
DATED : April 23, 2019
INVENTOR(S) : Paul Duesterhoft et al.

Page 1 of 1

It is certified that error appears in the above-identified patent and that said Letters Patent is hereby corrected as shown below:

In the Claims

Column 48, Lines 66-67, Claim 18, delete "the plurality of projects extend outward in substantially same place as the surface of the substrate" and insert -- the plurality of projections extend outward in substantially the same place as the surface of the substrate -- therefor.

Signed and Sealed this
Thirteenth Day of August, 2019

Andrei Iancu
*Director of the United States Patent and Trademark Office*